US011091800B2

(12) United States Patent
Underhill

(10) Patent No.: US 11,091,800 B2
(45) Date of Patent: Aug. 17, 2021

(54) SIZE-SELECTION OF CELL-FREE DNA FOR INCREASING FAMILY SIZE DURING NEXT-GENERATION SEQUENCING

(71) Applicant: University of Utah Research Foundation, Salt Lake City, UT (US)

(72) Inventor: Hunter R. Underhill, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 104 days.

(21) Appl. No.: 16/137,432

(22) Filed: Sep. 20, 2018

(65) Prior Publication Data
US 2019/0106737 A1 Apr. 11, 2019

Related U.S. Application Data

(60) Provisional application No. 62/561,149, filed on Sep. 20, 2017.

(51) Int. Cl.
*C12Q 1/6848* (2018.01)
*C12Q 1/6855* (2018.01)
*C12Q 1/6874* (2018.01)
*C12Q 1/6806* (2018.01)

(52) U.S. Cl.
CPC ......... *C12Q 1/6848* (2013.01); *C12Q 1/6806* (2013.01); *C12Q 1/6855* (2013.01); *C12Q 1/6874* (2013.01)

(58) Field of Classification Search
None
See application file for complete search history.

(56) References Cited

PUBLICATIONS

Phallen et al., "Direct detection of early-stage cancers using circulating tumor DNA," Sci. Transl. Med. 2017, 9(403):eaan2415, published Aug. 16, 2017. (Year: 2017).*
Underhill et al., "Fragment Length of Circulating Tumor DNA," PLoS Genet. 2016, 12(7):e1006162, published Jul. 18, 2016. (Year: 2016).*
Uyaguari-Diaz et al., "Automated Gel Size Selection to Improve the Quality of Next-generation Sequencing Libraries Prepared from Environmental Water Samples," J. Vis. Exp. 2015, 98:e52685. (Year: 2015).*
Abbosh et al.; Phylogenetic ctDNA Analysis Depicts Early Stage Lung Cancer Evolution; Nature; (Apr. 26, 2017); pp. 446-451; vol. 545, No. 7655; <doi: 10.1038/nature22364 >.
Bettegowda et al.; "Detection of Circulating Tumor DNA in Early- and Late-Stage Human Malignancies;" Science Translational Medicine; (Feb. 19, 2014); 25 pages; vol. 6, Issue 224: 224ra24; <doi: 10.1126/scitranslmed.3007094 >.
Chan et al.; "Second Generation Noninvasive Fetal Genome Analysis Reveals De Novo Mutations, Single-Base Parental Inheritance, and Preferred DNA Ends;" Proceedings of the National Academy of Sciences of the United States of America; (Oct. 31, 2016); pp. E8159-E8168; vol. 113, No. 50;<doi: 10.1073/pnas.1615800113.
Chan et al.; "Size Distributions of Maternal and Fetal DNA in Maternal Plasma;" Clinical Chemistry; (2004); pp. 88-92; vol. 50, No. 1; <doi: 10.1373/clinchem.2003.024893 >.
Donaldson et al.; "Circulating Tumor DNA: Measurement and Clinical Utility;" Annual Review of Medicine; (Aug. 28, 2017); pp. 223-234; vol. 69; <doi: 10.1146/annurev-med-041316-085721 >.
Fan et al.; "Analysis of the Size Distributions of Fetal and Maternal Cell-Free DNA by Paired-End Sequencing;" Clinical Chemistry; (2010); pp. 1279-1286; vol. 56, No. 8; <doi: 10.1373/clinchem. 2010.144188 >.
Garrigou et al.; "A Study of Hypermethylated Circulating Tumor DNA as a Universal Colorectal Cancer Biomarker;" Clinical Chemistry; (Jun. 3, 2016); pp. 1129-1139; vol. 62, No. 8; <doi: 10.1373/clinchem.2015.253609 >.
Hahn et al.; "Microsystem for Isolation of Fetal DNA from Maternal Plasma b y Preparative Size Separation;" Clinical Chemistry; (Oct. 1, 2009); 8 pages; vol. 55, No. 12; <doi: 10.1373/clinchem.2009. 127480 >.
Huggett et al.; "The Digital MIQE Guidelines: Minimum Information for Publication of Quantitative Digital PCR Experiments;" Clinical Chemistry; (2013); pp. 892-902; vol. 59, No. 6; <doi: 10.1373/clinchem.2013.206375 >.
Jiang et al.; "The Long and Short of Circulating Cell-Free DNA and the Ins and Outs of Molecular Diagnostics;" Trends in Genetics; (Jun. 1, 2016); pp. 360-371; vol. 32, Issue 6; <doi: 10.1016/j.tig. 2016.03.009 >.
Jorgez et al.; "Improving Enrichment of Circulating Fetal DNA for Genetic Testing: Size Fractionation Followed by Whole Gene Amplification;" Fetal Diagnosis and Therapy; (Sep. 22, 2009); pp. 314-319; vol. 25, No. 3; <doi: 10.1159/000235877 >.
Kennedy et al.; "Detecting Ultralow-Frequency Mutations by Duplex Sequencing;" Nature Protocols; (Oct. 9, 2014); pp. 2586-2606; vol. 9, No. 11; <doi: 10.1038/nprot.2014.170 >.
Kou et al.; "Benefits and Challenges with Applying Unique Molecular Identifiers in Next Generation Sequencing to Detect Low Frequency Mutations;" PLoS One; (Jan. 11, 2016); 15 pages; vol. 11, No. 1: e0146638; <doi: 10.1371/journal.pone.0146638 >.

(Continued)

*Primary Examiner* — Kaijiang Zhang
(74) *Attorney, Agent, or Firm* — Todd Alder

(57) ABSTRACT

A method of increasing detection of low-abundant fragments of cell-free DNA (ccfDNA) in a biological sample is disclosed and discussed. Such a method can include isolating an initial fraction of ccfDNA fragments from a biological sample, ligating a unique molecular identifier (UMI) to each of the ccfDNA fragments in the initial fraction, amplifying the plurality of ccfDNA fragments to generate a ccfDNA library, isolating a short fraction of ccfDNA fragments from the ccfDNA library, where the ccfDNA fragments in the short fraction are limited to a size of less than or equal to 160 base pairs (bp), amplifying the ccfDNA fragments in the short fraction, and sequencing the ccfDNA fragments in the short fraction to generate sequenced ccfDNA fragments.

16 Claims, 34 Drawing Sheets
Specification includes a Sequence Listing.

(56) References Cited

PUBLICATIONS

Lanman et al.; "Analytical and Clinical Validation of a Digital Sequencing Panel for Quantitative, Highly Accurate Evaluation of Cell-Free Circulating Tumor DNA;" PLoS One; (2015); vol. 10, No. 10: e0140712; <doi: 10.1371/journal.pone.0140712 >.

Leary et al.; "Development of Personalized Tumor biomarkers using Massively Parallel Sequencing;" Science Translational Medicine; (Feb. 24, 2010); 15 pages; vol. 2, No. 20: 20ra14; <doi:10.1126/scitranslmed.30000702 >.

Li et al.; "Size Separation of Circulatory DNA in Maternal Plasma Permits Ready Detection of Fetal DNA Polymorphisms;" Clinical Chemistry; (2004); pp. 1002-1011; vol. 50, No. 6; <doi: 10.1373/clinchem.2003.029835 >.

Lo et al.; "Maternal Plasma DNA Sequencing Reveals the Genome-Wide Genetic Mutational Profile of the Fetus;" Science Translational Medicine; (Dec. 2010); 13 pages; vol. 2, Issue 61: 61ra91; <doi: 10.1126/scitranslmed.3001720 >.

Lui et al.; "Predominant Hematopoietic Origin of Cell-Free DNA in Plasma and Serum after Sex-Mismatched Bone Marrow Transplantation;" Clinical Chemistry; (2002); pp. 421-427; vol. 48, No. 3.

Manley et al.; "Monitoring Error Rates in Illumina Sequencing;" Journal of Biomolecular Techniques; (2016); pp. 125-128; vol. 27; <doi: 10.7171/jbt.16-2704-002 >.

McGranahan et al.; "Clonal Heterogeneity and Tumor Evolution: Past, Present, and the Future;" Cell; (Feb. 9, 2017); pp. 613-628; vol. 168; <doi: 10.1016/j.cell.2017.01.018 >.

Milbury et al.; "Determining Lower Limits of Detection of Digital PCR Assays for Cancer-Related Gene Mutations;" Biomolecular Detection and Quantification; (2014); pp. 8-22; vol. 1, No. 1; <doi: 10.1016/j.bdq.2014.08.001 >.

Murtaza et al.; "Multifocal Clonal Evolution Characterized using Circulating Tumour DNA in a Case of Metastatic Breast Cancer;" Nature Communications; (Nov. 4, 2015); 6 pages; vol. 6, No. 8760; <doi: 10.1038/ncomms9760 >.

Nagata; "Apoptotic DNA Fragmentation;" Experimental Cell Research; (Apr. 10, 2000); pp. 12-18; vol. 256, Issue 1; <doi: 10.1006/excr.2000.4834 >.

Newman et al.; "Integrated Digital Error Suppression for Improved Detection of Circulating Tumor DNA;" Nature Biotechnology; (May 2016); pp. 547-555; vol. 34, No. 5; <doi: 10.1038/nbt.3520 >.

Paweletz et al.; "Bias-Corrected Targeted Next-Generation Sequencing for Rapid, Multiplexed Detection of Actionable Alterations in Cell-Free DNA from Advanced Lung Cancer Patients;" Clinical Cancer Research; (Feb. 15, 2016); pp. 915-922; vol. 22, No. 4; <doi: 10.1158/1078-0432.CCR-15-1627-T >.

Phallen et al.; "Direct Detection of Early-Stage Cancers using Circulating Tumor DNA;" Science Translational Medicine; (Aug. 16, 2017); 12 pages; vol. 9: eaan2415.

Scmitt et al.; "Detection of Ultra-Rare Mutations by Next-Generation Sequencing;" Proceedings of the National Academy of Sciences of the United States of America; (Sep. 4, 2012); pp. 14508-14513; vol. 109, No. 36; <doi: 10.1073/pnas.1208715109 >.

Snyder et al.; "Cell-Free DNA Comprises an in vivo Nucleosome Footprint that Informs its Tissues-of-Origin;" Cell; (Jan. 14, 2016); pp. 57-68; vol. 164, No. 1-2; <doi: 10.1016/j.cell.2015.11.050 >.

Taly et al.; "Multiplex Picodroplet Digital PCR to Detect KRAS Mutations in Circulating DNA from the Plasma of Colorectal Cancer Patients;" Clinical Chemistry; (2013); pp. 1722-1731; vol. 59, No. 12; <doi: 10.1373/clinchem.2013.206359 >.

Tie et al.; "Circulating Tumor DNA Analysis Detects Minimal Residual Disease and Predicts Recurrence in Patients with Stage II Colon Cancer;" Science Translational Medicine; (Jul. 6, 2016); 21 pages; vol. 8, No. 346: 346ra92; <doi: 10.1126/scitranslmed.aaf6219 >.

Underhill et al.; "Fragment Length of Circulating Tumor DNA;" PLoS Genetics; (Jul. 18, 2016); 24 pages; vol. 12, No. 7; <doi: 10.1371/journal.pgen.1006162 >.

Uyaguari et al.; "Automated Gel Size Selection to Improve the Quality of Next-Generation Sequencing Libraries Prepared from Environmental Water Samples;" Journal of Visualized Experiments; (Apr. 17, 2015); 6 pages; vol. 98; <doi: 10.3791/52685 >.

Yu et al.; "Size-Based Molecular Diagnostics using Plasma DNA for Noninvasive Prenatal Testing;" Proceedings of the National Academy of Sciences of the United States of America; (Jun. 10, 2014); pp. 8583-8588; vol. 111, No. 23; <doi: 10.1073/pnas.1406103111 >.

* cited by examiner

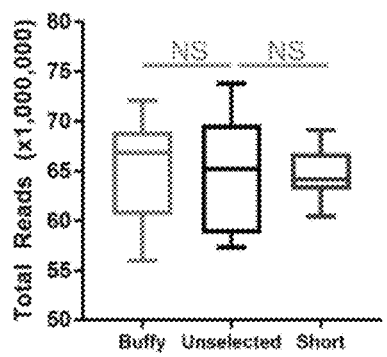
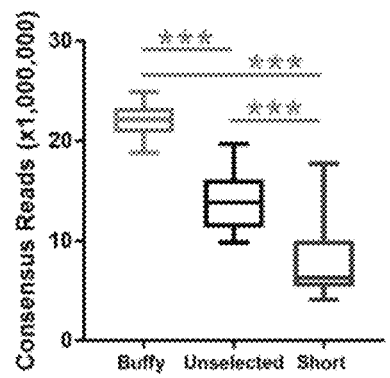
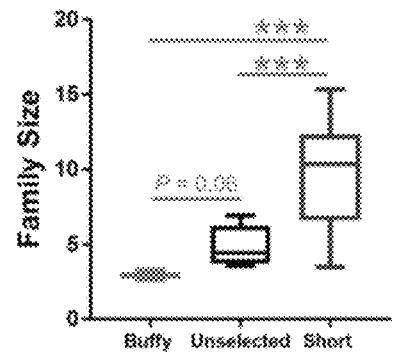
FIG. 4A          FIG. 4B          FIG. 4C
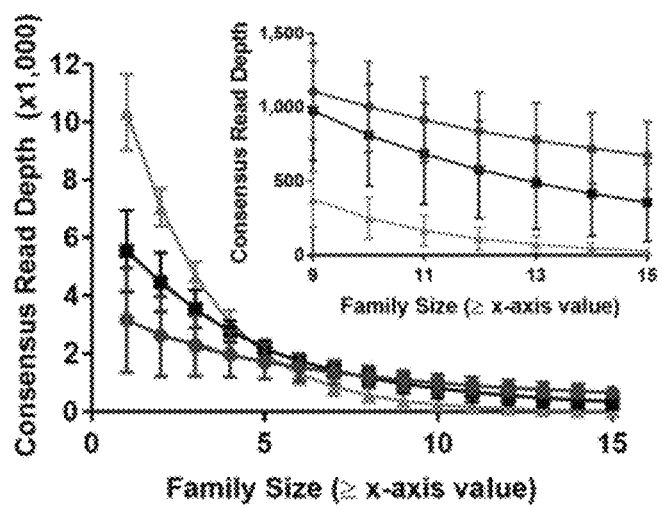
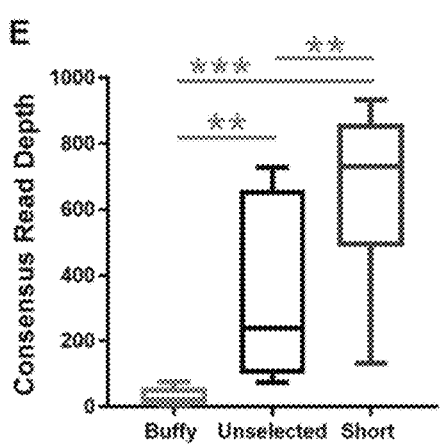
FIG. 4D          FIG. 4E

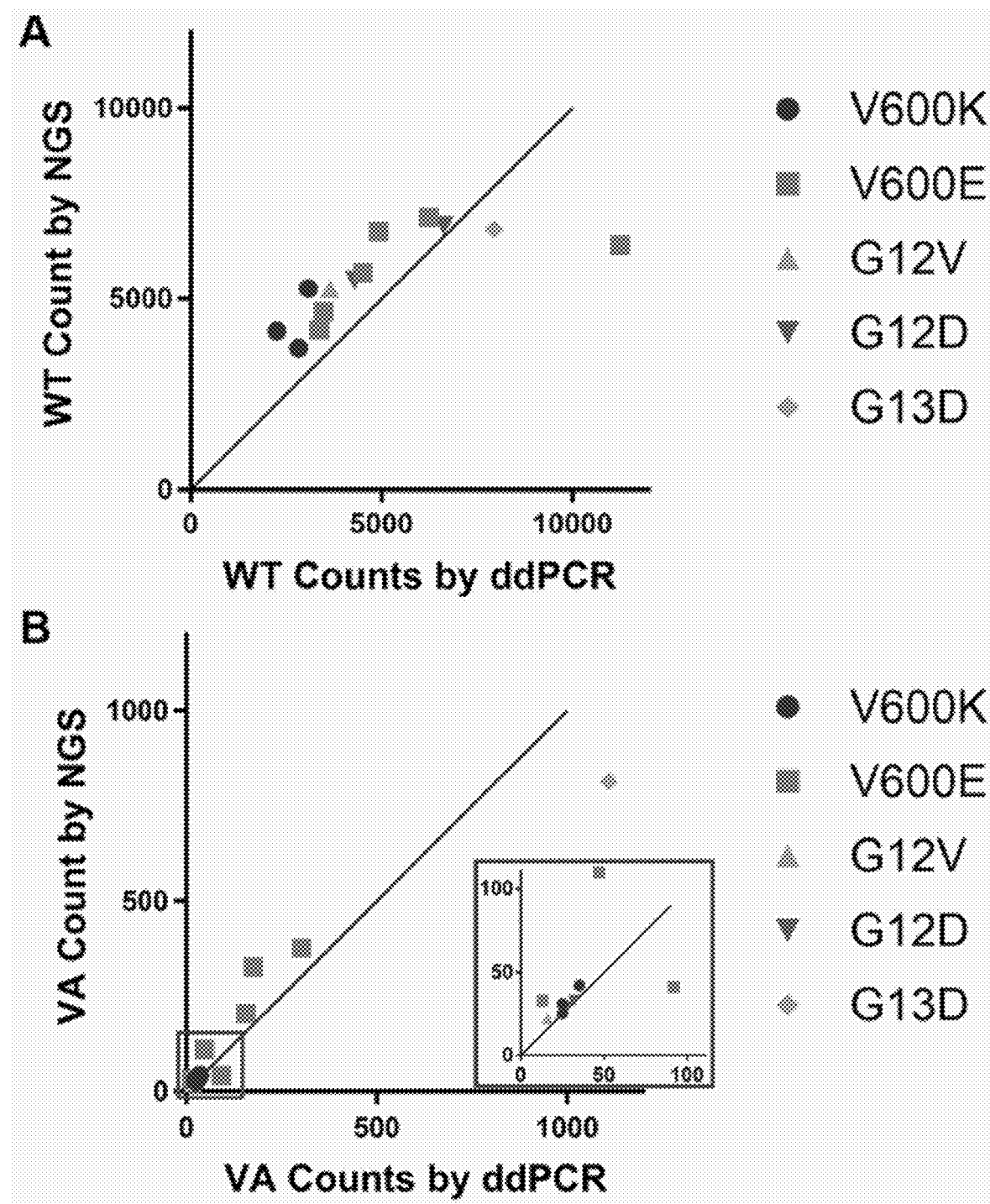
FIG. 8A-B

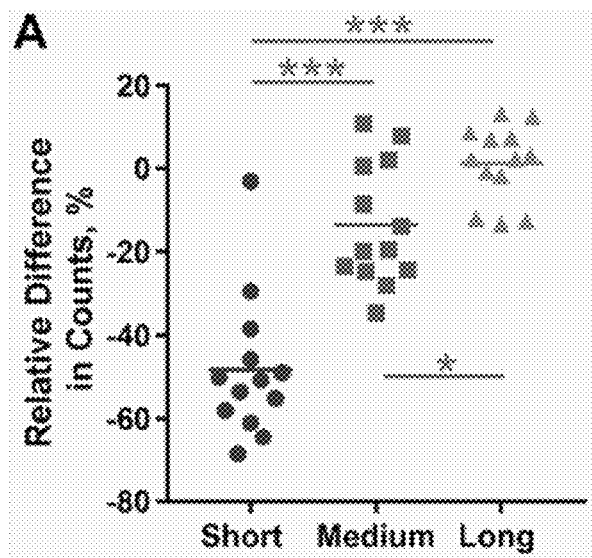
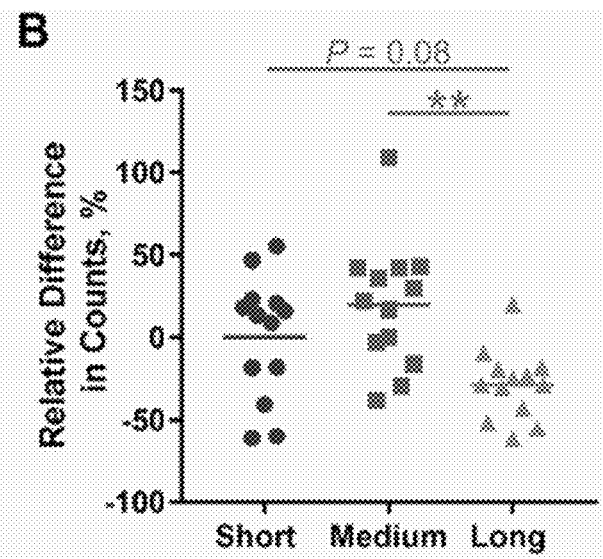
FIG. 15A  FIG. 15B
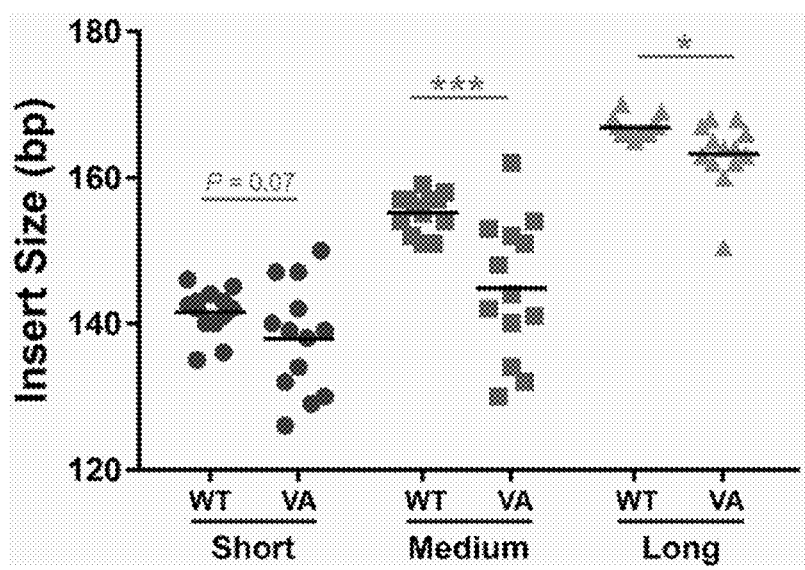
FIG. 16

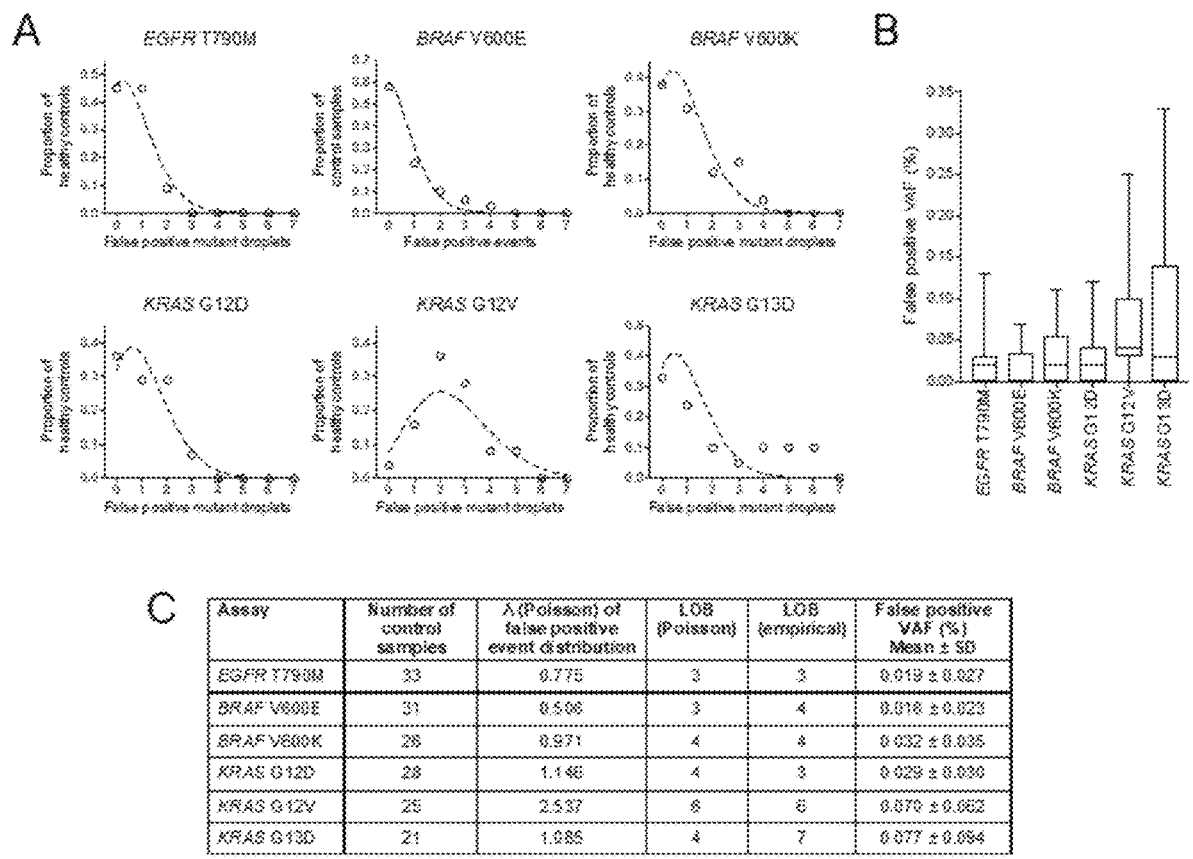
FIG. 25A-C

SEQUENCE LISTING

<160> NUMBER OF SEQ ID NOS: 8

<210> SEQ ID NO 1
<211> LENGTH: 20
<212> TYPE: DNA
<213> ORGANISM: Homo sapiens

<400> SEQUENCE: 1
gatgcgatgt tatcggtgcg                                               20

<210> SEQ ID NO 2
<211> LENGTH: 20
<212> TYPE: DNA
<213> ORGANISM: Homo sapiens

<400> SEQUENCE: 2
cacaggtgag ccgtgtagtt                                               20

<210> SEQ ID NO 3
<211> LENGTH: 20
<212> TYPE: DNA
<213> ORGANISM: Homo sapiens

<400> SEQUENCE: 3
tggaacccac cgagtgaaag                                               20

<210> SEQ ID NO 4
<211> LENGTH: 20
<212> TYPE: DNA
<213> ORGANISM: Homo sapiens

<400> SEQUENCE: 4
caatgcagca gcagtcatcc                                               20

<210> SEQ ID NO 5
<211> LENGTH: 20
<212> TYPE: DNA
<213> ORGANISM: Homo sapiens

<400> SEQUENCE: 5
cggcacgatc tcgtcaaaac                                               20

<210> SEQ ID NO 6
<211> LENGTH: 20
<212> TYPE: DNA
<213> ORGANISM: Homo sapiens

<400> SEQUENCE: 6
gccttgaact gaaatgcccg                                               20

<210> SEQ ID NO 7
<211> LENGTH: 20
<212> TYPE: DNA
<213> ORGANISM: Homo sapiens

<400> SEQUENCE: 7
ggaagctgca tgatgcgatg                                               20

<210> SEQ ID NO 8
<211> LENGTH: 20

```
<212> TYPE: DNA
<213> ORGANISM: Homo sapiens

<400> SEQUENCE: 8
ctggtgcgtt tcgttggaag                                               20
```

SIZE-SELECTION OF CELL-FREE DNA FOR INCREASING FAMILY SIZE DURING NEXT-GENERATION SEQUENCING

CROSS-REFERENCE TO RELATED APPLICATIONS

This application claims the benefit of U.S. Provisional Patent Application No. 62/561,149, filed on Sep. 20, 2017, which is incorporated herein by reference in its entirety.

BACKGROUND

A portion of the DNA from healthy cells undergoing apoptosis enters the circulation and is known as circulating cell-free DNA as it is not contained within a cellular membrane. Tumor cells similarly deposit DNA into the circulation, which is referred to as circulating tumor DNA (ctDNA). Use of ctDNA is becoming increasingly recognized as a non-invasive means to diagnose and detect tumor recurrence (i.e., the liquid biopsy).

BRIEF DESCRIPTION OF THE DRAWINGS

FIG. 4A illustrates data showing a relationship between size-based selection of cell-free DNA and increasing family size in accordance with an example embodiment;

FIG. 4B illustrates data showing a relationship between size-based selection of cell-free DNA and increasing family size in accordance with an example embodiment;

FIG. 4C illustrates data showing a relationship between size-based selection of cell-free DNA and increasing family size in accordance with an example embodiment;

FIG. 4DA illustrates data showing a relationship between size-based selection of cell-free DNA and increasing family size in accordance with an example embodiment;

FIG. 4E illustrates data showing a relationship between size-based selection of cell-free DNA and increasing family size in accordance with an example embodiment;

FIG. 8A illustrates data for wild type (WT) and variant allele (VA) counts by ddPCR and NGS in accordance with an example embodiment;

FIG. 8B illustrates data for wild type (WT) and variant allele (VA) counts by ddPCR and NGS in accordance with an example embodiment;

FIG. 15A illustrates data showing the percent difference in wild type (WT) and variant counts for each ccfDNA fraction relative to unselected ccfDNA counts in accordance with an example embodiment;

FIG. 15B illustrates data showing the percent difference in wild type (WT) and variant counts for each ccfDNA fraction relative to unselected ccfDNA counts in accordance with an example embodiment;

FIG. 16 illustrates data showing median insert size for the wild type (WT) and variant allele (VA) for each ccfDNA fraction in accordance with an example embodiment;

FIG. 25A illustrates data showing false positive droplet events in control samples in accordance with an example embodiment;

FIG. 25B illustrates data showing false positive droplet events in control samples in accordance with an example embodiment;

FIG. 25C illustrates data showing false positive droplet events in control samples in accordance with an example embodiment;

DESCRIPTION OF EMBODIMENTS

Figure 1:
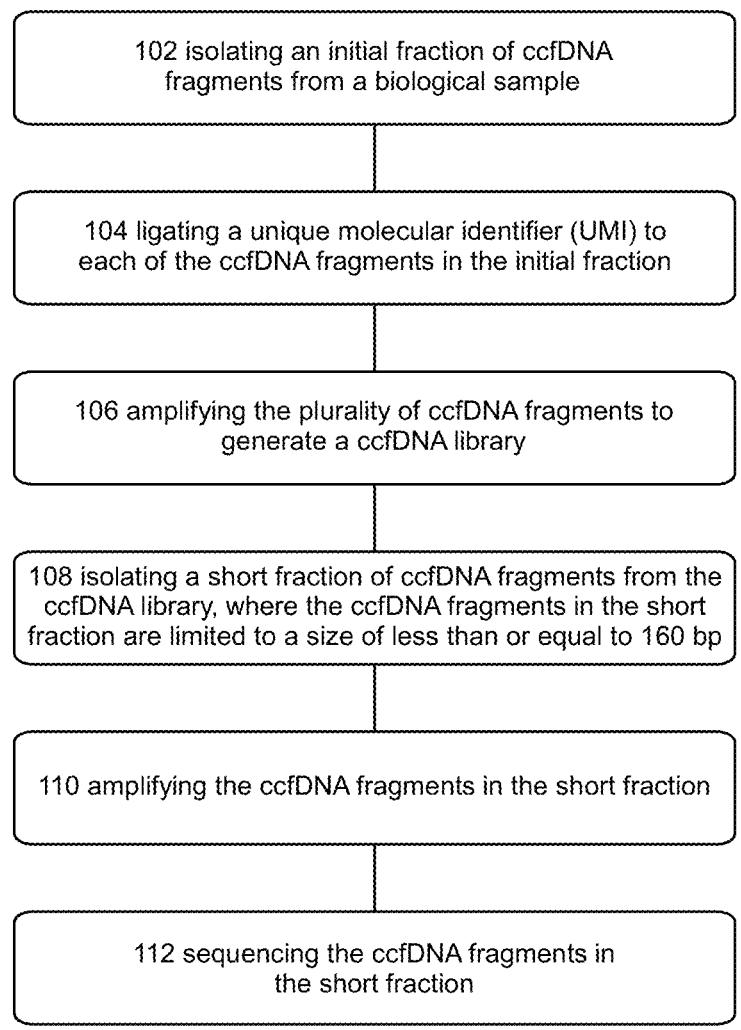
FIG. 1 illustrates steps performed in a method for increasing detection of low-abundant fragments of cell-free DNA (ccfDNA) in a biological sample from a subject in accordance with an example embodiment.

Although the following detailed description contains many specifics for the purpose of illustration, one of ordinary skill in the art will appreciate that many variations and alterations to the following details can be made and are considered included herein. Accordingly, the following embodiments are set forth without any loss of generality to, and without imposing limitations upon, any claims set forth. It is also to be understood that the terminology used herein is for describing particular embodiments only, and is not intended to be limiting. Unless defined otherwise, all technical and scientific terms used herein have the same meaning as commonly understood by one of ordinary skill in the art to which this disclosure belongs. Also, the same reference numerals in appearing in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are described to provide a thorough understanding of various embodiments. One of ordinary skill in the relevant art will recognize, however, that such detailed embodiments do not limit the overall concepts articulated herein, but are merely representative thereof, and will also recognize that the technology can be practiced without one or more of the specific details, or with other methods, components, layouts, etc. In other instances, well-known structures, materials, techniques, or the like may not be shown or described in detail to avoid obscuring aspects of the disclosure.

As used herein, the terms "comprises," "comprising," "containing," "having," and the like, all have the meaning ascribed to them according to U.S. Patent law, and can mean "includes," "including," and the like, which are open-ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning ascribed to them according to U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition that do not affect the composition's nature or characteristics would be permissible if present under the "consisting essentially of" language, even though not expressly recited in a list of items following such terminology. When using an open-ended term in this written description, such as "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total to completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of phrases including "an example" or "an embodiment" in various places throughout this specification are not necessarily all referring to the same example or embodiment.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As, used herein, the term "biological sample" refers to a complex mixture of biological origin, such as that obtained from a biological subject, which in many cases can be a human subject.

An initial overview of embodiments is provided below, and specific embodiments are then described in further detail. This initial summary is intended to aid readers in understanding the disclosure more quickly, and is not intended to identify key or essential technological features, nor is it intended to limit the scope of the claimed subject matter.

Circulating cell-free DNA (ccfDNA) refers to fragments of DNA that are no longer within a cell and are present in the circulatory system. The term ccfDNA can also be used to describe these DNA fragments following extraction and subsequent processing. ccfDNA can be released from a cell as a result of various processes, including both normal and abnormal apoptotic events, cellular excretions, necrosis, and the like. Specific forms of ccfDNA may be present in the circulatory system as a result of various medical conditions, disease states, pregnancy, and the like. The accessibility of these genomic fragments in the circulatory system through a simple blood sample provides a low-risk opportunity to screen for various phenotypes, conditions, and the like. As a result, ccfDNA testing is an emerging diagnostic approach that allows for noninvasive, rapid, and real-time testing in research and clinical settings.

For example, during pregnancy, placental cells release fetal DNA into the mother's circulatory system, which is referred to herein as circulating fetal-derived cell-free DNA (cfDNA). cfDNA thus provides the opportunity to perform fetal genetic screening from samples of the mother's blood, thus avoiding more invasive and potentially risky amniocentesis and chorionic villus sampling (CVS) procedures. cfDNA can be used to screen for any genetic phenotype or condition detectable in the fetal genome, nonlimiting examples of which can include fetal sex, fetal rhesus (Rh) blood type, chromosomal disorders such as trisomy 22, trisomy 21 (down syndrome), trisomy 18, trisomy 16, trisomy 13, triploidy, sex chromosome aneuploidy, and the like, chromosomal deletion disorders (microdeletion syndrome) such as Prader-Willi syndrome, and disorders associated with bone or anatomical abnormalities, to name a few.

As another example, solid tissues, including cancers, also contribute to the plasma ccfDNA pool. Such circulating tumor-derived DNA fragments, referred to herein as circulating tumor DNA (ctDNA), is a type of cell-free DNA that can originate directly from a cancer, tumor, or from circulating tumor cells that have been shed from primary tumors and have entered the bloodstream or lymphatic system. ctDNA bear the molecular signatures of the neoplastic cell genome. Relative to microdissection of tumor tissue, which interrogates a minute and focal fraction of intratumor genetic diversity, ctDNA can be used to sample clonal varieties of both primary and metastatic sites through perfusion sampling. However, ctDNA is typically present at very low allele frequencies (e.g., median of ~0.5% in some cases) due to dilution by the abundant normal ccfDNA. As total ctDNA content is correlated with advancing disease stage, application of ccfDNA diagnostics for early disease detection will likely need reliable identification of very-low variant allele frequencies (VAFs), which can in many cases be less than 1%. In addition, intratumoral genetic heterogeneity is common and is a key challenge in cancer medicine. Identification of minor subclonal populations is important for detection of emerging chemoresistance, minimal residual disease, and disease progression.

Broad clinical applications based on various forms of ccfDNA have been limited by challenges associated with detecting such ccfDNA forms amongst the more abundant normal ccfDNA. This can be particularly true in ccfDNA forms such as non-metastatic solid tumors, for example, where ctDNA variants may be present at a very low frequency (e.g., <1%). It is illuminating to note that the sequencing error rate for standard next-generation sequencing (NGS) protocols is ~1%. Therefore, to detect variants with a frequency <1% an ultra-high read depth, a reduced error rate, an improved sensitivity, or some combination thereof is likely needed. Thus, accurate detection of variant alleles, particularly when using untargeted searches, remains an obstacle to widespread application of cell-free DNA in screening for clinical use, and particularly for oncology.

NGS enables a broad search for both known and unknown tumor-associated variants including single nucleotide variants, copy number variations, and chromosomal rearrangements. However, even the highest fidelity sequencing platforms introduce errors at ≥0.1%. Additional nucleotide changes may be introduced in the PCR amplification steps of sequencing library preparations. Such accumulation of potential false positive errors by sequencing and PCR limits reliable identification of true variants that occur with <1% frequency. Several approaches have been taken to improve very low variant calling by NGS. Ultra-deep sequencing (e.g., >30,000× read depth) improves detection of low frequency variants in ccfDNA, but may not be cost-effective for routine diagnostic testing.

The present disclosure demonstrates techniques that overcome these obstacles and provide high accuracy screening of ccfDNA for fragments of interest that are present at very low frequencies in a biological sample. In one such technique, sample complexity can be reduced to increase the signal-to-noise ratio of a fragment of interest prior to sequencing. Reducing sample complexity facilitates an increase in sequencing read depth for ccfDNA fragments, thus greatly increasing the signal-to-noise ratio of variant alleles in the ccfDNA sample. While any technique for reducing sample complexity is considered to be within the present scope, in one example embodiment this can be accomplished through a size-based selection of ccfDNA fragments prior to sequencing. Such enrichment can be accomplished by selecting for shorter ccfDNA fragments, an approach that is feasible as ccfDNA does not require shearing prior to library preparation, as is common with buffy-coat DNA techniques or tumor DNA that is genomic in length (>1 kb). As has been described, ccfDNA is already in a fragmented state due to the apoptotic process and subsequent degradation by nucleases. The most common fragment length for ccfDNA is about 170 bp, which corresponds to the length of a mononucleosome. A distribution of fragment sizes is present around this principal peak. Additional peaks generally occur at ~340 bp (dinucleosome) and ~510 bp (trinucleosome). The principal fragment length of many ccfDNA fragments of interest is shorter. For example, many ctDNA fragments most commonly occurs at about 120-150 bp. Furthermore, selection of shorter fragments sizes from an original cell-free DNA sample can increase VAF, thus improving sensitivity.

As is shown in FIG. 1, one example method of increasing detection of low-abundance target fragments of ccfDNA in a biological sample from a subject can include 102 isolating an initial fraction of ccfDNA fragments from a biological sample, 104 ligating a unique molecular identifier (UMI) to each of the ccfDNA fragments in the initial fraction, 106 amplifying the plurality of ccfDNA fragments to generate a ccfDNA library, 108 isolating a short fraction of ccfDNA fragments from the ccfDNA library, where the ccfDNA fragments in the short fraction are limited to a size of less than or equal to 160 bp, 110 amplifying the ccfDNA fragments in the short fraction, and 112 sequencing the ccfDNA fragments in the short fraction. The process of isolating shorter fragments from the ccfDNA library prior to sequencing increases the VAF to improve sensitivity, thus allowing low concentration target fragments, such as ctDNA, cfDNA, and the like, to be enriched.

A biological sample can include any sample taken from a subject that can include ccfDNA. One common biological sample is blood, including components of blood such as serum or plasma. In some examples, the biological sample is taken from the subject being screened, while in other examples the subject being screened can be different from the subject from which the sample was taken, such as would be the case for a pregnant mother providing a biological sample for screening a fetus. Thus, the extraction of the biological sample can vary depending on the nature of the sample itself and the particular screening assay being performed. In one example, a blood sample can be centrifuged to separate into the well-known blood cell, buffy-coat, and plasma layers. ccfDNA is generally present in the plasma layer following centrifugation, and can be isolated therefrom (i.e., the initial fraction of ccfDNA). Once isolated, a UMI can be ligated to each ccfDNA fragment in the initial fraction. It should be noted that the ligation reaction may not ligate a UMI to all ccfDNA fragments present in the sample. It is thus intended that the phrase "ligated to each ccfDNA fragment in the initial fraction" define the initial fraction as including only those ccfDNA fragments that were successfully ligated.

The UMI can include any type of molecular identifier, including molecular barcodes for example, that are capable of uniquely identifying each ccfDNA fragment and being amplified with the associated ccfDNA fragment. UMIs can include external adapters, internal adapters, or combination thereof. Such adapters can be custom adapters, standard adapters, or standard adapters with custom modifications. The UMIs thus enable tracking of each ccfDNA fragment duplicate during the PCR amplification process.

Once the ccfDNA library has been constructed following the amplification of the ccfDNA fragments from the initial fraction, the short fraction of ccfDNA fragments can be isolated for further amplification and sequencing. The isolation of the short fraction can be accomplished by any technique capable of extracting ccfDNA fragments based on size (i.e., length), which is not to be seen as limiting. In one example, the extraction technique can utilize an electrophoretic gel-based process, including polyacrylamide and agarose gels. Such gel-based extractions can include manual techniques (e.g., gel cutouts), fully automated techniques, and semi-automated techniques. One nonlimiting example of a non-gel extraction technique includes liquid chromatography extractions.

As one example of a gel-base extraction technique, ccfDNA fragments from the ccfDNA library are electrophoretically migrated through an electrophoretic gel to separate the ccfDNA fragments based on size. A target portion of the electrophoretic gel is then selected that corresponds to the ccfDNA fragment size of the short fraction, and the target portion is extracted from gel to isolate the short fraction of ccfDNA fragments. As has been described, this process can be a manual extraction, where the target portion is manually cut from the gel. As has also been described, the electrophoresis and subsequent extraction can be accomplished in an automated or semi-automated fashion, which in some cases can result in increased migration and/or extraction accuracy.

Once isolated from the longer ccfDNA fragments of the ccfDNA library, the ccfDNA fragments of the short fraction can be PCR or otherwise amplified. Thus, by first reducing the number of unique ccfDNA fragments in a sample (e.g., to shorter ccfDNA fragments), followed by PCR amplification of the size-reduced fraction of ccfDNA, the PCR enzymatic chemistry becomes focused on fewer ccfDNA fragments, which generates more amplicons of the same DNA molecule to effectively increase family size.

As has been described, in many examples the size of ccfDNA fragments in the selected short fraction is less than the peak of the mononucleosome, which is about 170 bp. The specific fragment size cutoff for the short fraction can vary, depending on the size of the fragment of interest, the screening design, and the like. In one example, the size cutoff for the short fraction can be less than or equal to 160 bp. In another example, the size cutoff for the short fraction can be less than or equal to 155 bp. In yet another example, the size cutoff for the short fraction can be less than or equal to 150 bp. In a further example, the size cutoff for the short fraction can be less than or equal to 145 bp. In another example, the size cutoff for the short fraction can be less than or equal to 130 bp.

In another example, isolating the short fraction of ccfDNA fragments from the ccfDNA library can include separating ccfDNA fragments from the ccfDNA library by liquid chromatography into fractions according to ccfDNA fragment size. Either during the separation process, or using isolated fractions following separation, a target fraction is selected that corresponds to the short fraction based on ccfDNA fragment size, which is extracted or otherwise utilized as the short fraction for subsequent amplification and sequencing.

Regardless of the specific techniques utilized, once amplified the ccfDNA fragments in the extracted short fraction are sequenced using any know and useful sequencing technique. In one example, the short fraction can be sequenced by any form of NGS procedure. The size-based extraction of the short fraction from the fragment library, combined with the subsequent amplification of the ccfDNA fragments from that fraction, allows NGS with sequencing error rates well below the ~1% standard error rate for such protocols, which in many cases can be ~0.05%, ~0.01%, or lower.

Following sequencing, ccfDNA fragment sequences can be grouped according to each UMI. DNA amplicons having the same UMI are considered to be a family, as each was derived from the same initial ccfDNA fragment. As such, DNA amplicons can be grouped according to the same UMI. In some examples, DNA amplicons having largely similar UMIs (e.g., >0.875) can also be grouped together, either with the group of DNA amplicons having the same UMI or as a separate group. Following grouping, a single consensus sequence is built for each UMI group. The technique for building the consensus sequence is not limiting. As one example, however, all of the sequences in a given UMI group are aligned and each base position in the consensus sequence is represented with the most common base in the family for that position.

Subsequent use of consensus sequences can vary depending on the intention of the screen. In many cases, consensus sequences can be compared against a sequence library of target sequences associated with genetic conditions and matching the consensus sequence to a target sequence in the sequence library. If, for example, the genetic condition is a medical condition, the specific medical condition associated with the matched target sequence can be identified. Once identified, the medical condition can be diagnosed in the subject, and an appropriate medical treatment can be prescribed or performed on the subject in order to treat the medical condition. In one example, such a medical condition can include a solid tumor, and thus the consensus sequence is from ctDNA. Treatment for such can vary depending on the specific type of tumor.

In another example, the genetic condition can be a genetic phenotype, which can include a normal genetic phenotype or an abnormal genetic phenotype. Examples include those listed above in the description of cfDNA. In such cases, it is noted that the subject providing the biological sample is a pregnant mother and the genetic phenotype is a fetal genetic phenotype.

Example Study 1

Size-Selection of Cell-Free DNA Increases Variant Allele Frequency ccfDNA from N=13 patients with solid tumors and known BRAF or KRAS tumor-derived variants present in ccfDNA underwent adapter ligation and UMI assignment. Samples were subsequently PCR amplified to generate libraries. Two specific size-range fractions were targeted for extraction from the ccfDNA library (1 µg) using an automated process (Ranger Technology, CoastalGenomics, Burnaby, Calif.) during a single run. An intermediate third size range was targeted for extraction on a second independent run from the ccfDNA library (1 µg) using the same automated process. The extracted fractions were amplified and then sequenced using a 128-gene panel (128 kb) on a HiSeq 2500 125 cycle paired end reads. Sequencing data was aligned, consensus sequences identified, and family size information for each consensus sequence denoted.

Figure 2A:
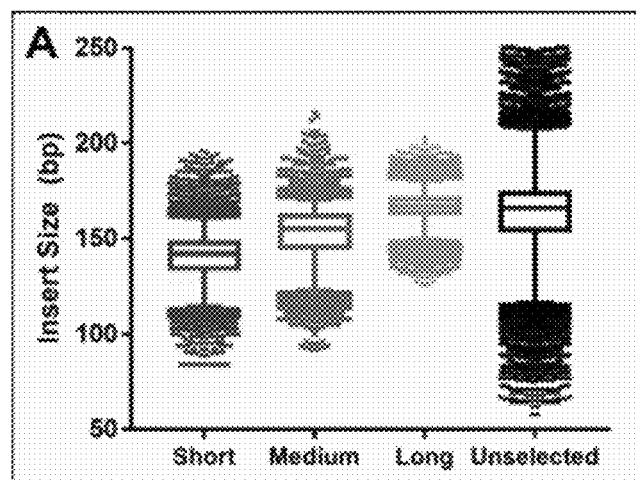
FIG. 2A illustrates data related to insert sizes from three fractions isolated from cell-free DNA using size-based criteria in accordance with an example embodiment.
Figure 2B:
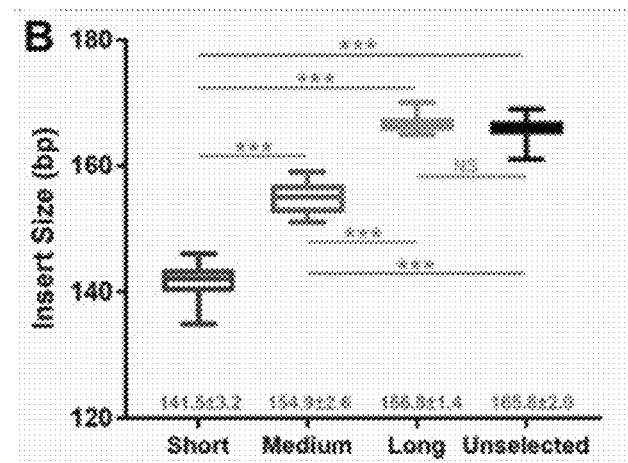
FIG. 2B illustrates data related to insert sizes from three fractions isolated from cell-free DNA using size-based criteria in accordance with an example embodiment.
Figure 2C:
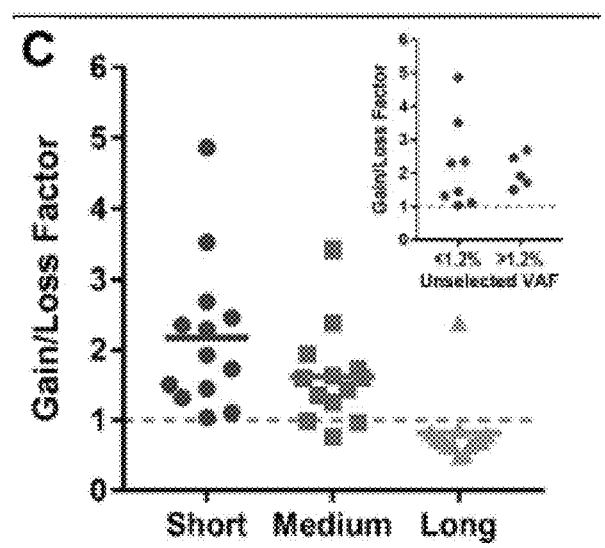
FIG. 2C illustrates data related to insert sizes from three fractions isolated from cell-free DNA using size-based criteria in accordance with an example embodiment.

The insert sizes from each fraction were overlapping (FIG. 2A), however the median insert size from each size-selection yielded discrete fractions (FIG. 2B). Variant allele frequency increased the most in the 'short' fraction (FIG. 2C). FIG. 2A specifically shows insert sizes from each of the three fractions ('short', 'medium', 'long') isolated from cell-free DNA using size-based criteria. The distribution of insert sizes prior to isolation of specific size-based fractions is labeled as 'unselected.' Note that there is overlap in insert sizes between fractions. However, the median insert size from each fraction is significantly different between fractions, as is shown in FIG. 2B. The variant allele frequency increased the most in the 'short' fraction, while the variant allele frequency decreased the most in the 'long' fraction, as is shown in FIG. 2C. The largest gain in variant allele frequency occurred in samples that began with the lowest variant allele frequency, as is shown in the insert in FIG. 2C. ***=P<0.001, NS=not significant.

Size Selection does not Adversely Affect Variant Allele Frequency

Figure 3A:
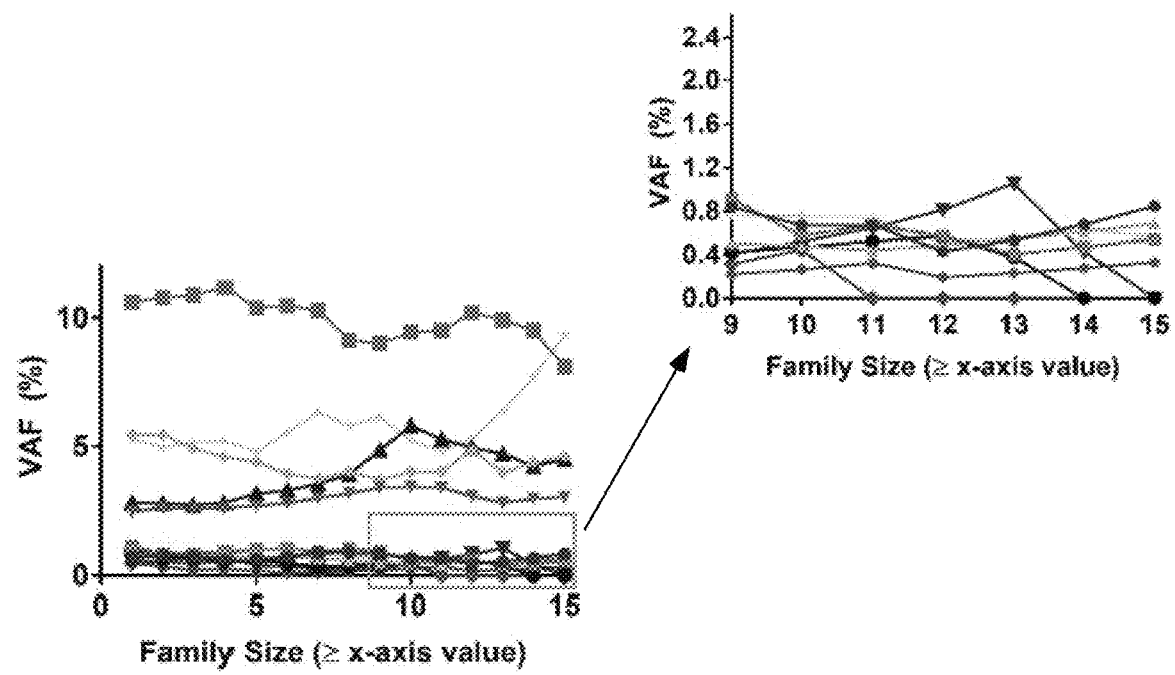
FIG. 3A illustrates data showing variant allele frequency related to increasingly larger family size in accordance with an example embodiment.
Figure 3B:
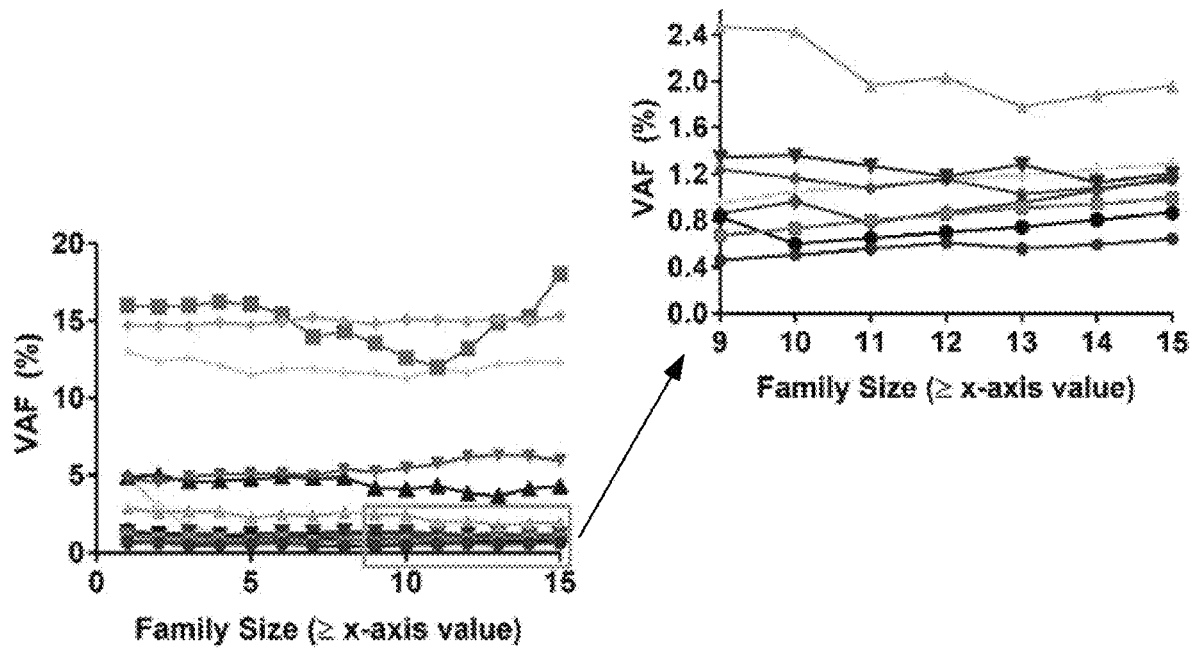
FIG. 3B illustrates data showing variant allele frequency related to increasingly larger family size in accordance with an example embodiment.

Change in variant allele frequency related to increasingly larger family size was then evaluated. In the 'unselected' cell-free DNA, variant allele frequency was relatively constant up to a family size of ≥10; however, subsequent incremental increases in family size caused loss of variant alleles (FIG. 3A). In contrast, variant allele frequency was relatively constant in the 'short' fraction isolated from cell-free DNA over as similar family size range (FIG. 3B). FIGS. 3A & 3B shows variant allele frequency (VAF) as a function of family size for the 'unselected' (FIG. 3A) cell-free DNA and the 'short' fraction of cell-free DNA (FIG. 3B). In the 'unselected' cell-free DNA, the VAF reduced to zero in some of the samples when family size became >10 (FIG. 3A inset). In the 'short' fraction of cell-free DNA (FIG. 3B), the VAF remained relatively constant up to a family size of 15 (FIG. 3B inset).

Size-Based Selection of Cell-Free DNA Increases Family Size

In addition to the 'unselected' cell-free DNA and 'short' cell-free DNA, libraries of buffy-coat DNA from the patients were similarly made using UMIs. In contrast to the cell-free DNA process, buffy-coat DNA was sheared and underwent only a single round of PCR amplification prior to capture enrichment for sequencing. The shearing of buffy-coat DNA is necessary due to the genomic size length of buffy-coat DNA that is not amenable to next-generation sequencing. The shearing of buffy-coat DNA generates an abundance of unique DNA molecules as the shearing process is random. In contrast, cell-free DNA is NOT sheared during the library formation process as the length of cell-free DNA is compatible with next-generation sequencers.

For a similar number of total reads (FIG. 4A), the average number of consensus aligned reads was greatest in the buffy coat DNA, followed by the 'unselected' cell-free DNA, and then the 'short' cell-free DNA (FIG. 4B). The consequent effect was larger family sizes in the 'short' cell-free DNA as there were fewer unique DNA molecules, which allotted more reads to PCR replicates (FIG. 4C). Thus, consensus read depth changed less in the 'short' cell-free DNA at the locations for the variants of interest (FIG. 4D) and read depth was greatest in the 'short' cell-free DNA at larger family sizes (FIG. 4E). In very-low frequency variants, there was a loss of variant allele frequency at larger family sizes in the 'unselected' cell-free DNA (FIG. 3A inset). This is explained by the reduced read depth. The relatively persistent variant allele frequencies seen in the 'short' cell-free DNA at larger family sizes (FIG. 3B inset) is attributable to the greater read depth at larger family sizes and the increased variant allele frequency that size-based selection of cell-free DNA affords. Total reads were similar for buffy coat DNA ('Buffy'), the 'unselected' cell-free DNA, and the 'short' cell-free DNA (FIG. 4A). Aligned consensus read depth (i.e., family size ≥1) was greatest for the buffy coat DNA (FIG. 4B). Family size was statistically largest in the 'short' cell-free DNA due to reduction of unique DNA molecules compared to both the buffy coat DNA and the 'unselected' cell-free DNA (FIG. 4C). At locations associated with variants of interest, the read depth was the most consistent regardless of family size for the 'short' cell-free DNA (FIG. 4D, circles). At a family size of ≥15, consensus read depth was greatest for the 'short' cell-free DNA (FIG. 4E). * P<0.001,  P=0.001, NS=not significant.

Larger Family Sizes Reduce False Positives

Figure 5A:
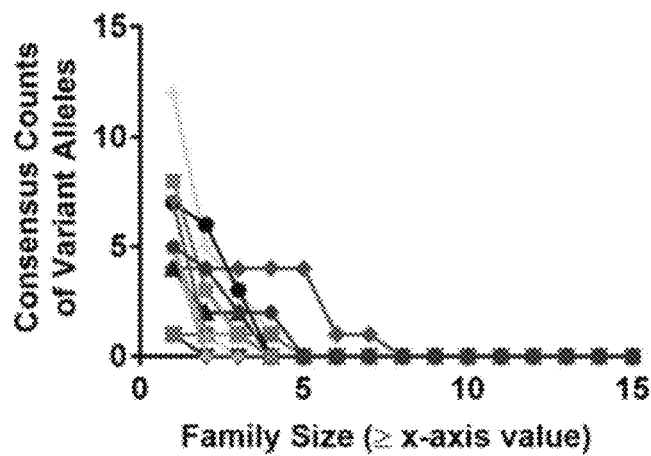
FIG. 5A illustrates data evaluating false positives for the variant alleles in association with family size in accordance with an example embodiment.
Figure 5B:
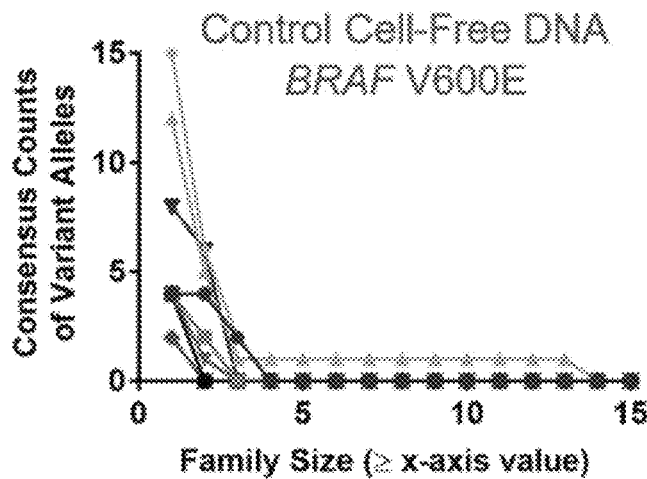
FIG. 5B illustrates data evaluating false positives for the variant alleles in association with family size in accordance with an example embodiment.
Figure 5C:
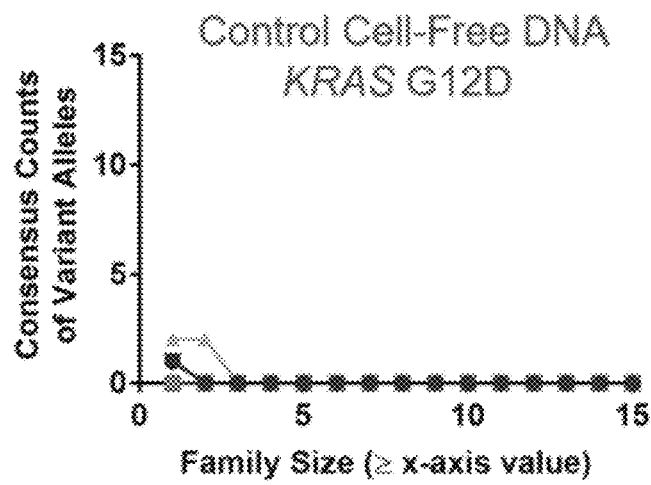
FIG. 5C illustrates data evaluating false positives for the variant alleles in association with family size in accordance with an example embodiment.

False positives for the variant alleles were then evaluated in association with family size. In the buffy coat DNA, false positives reduced with larger family sizes (FIG. 5A). In cell-free DNA from healthy controls, false positives similarly reduced with larger family sizes (FIG. 5B). Of note, different variants were associated with different levels of false positives (FIG. 5C), which suggests that false positives may be larger or smaller at different locations as compared to that presented herein. As such, the largest family sizes as possible are necessary to minimize false positives. Counts of corresponding variant alleles (false positives) in the buffy coat from the N=13 cancer patients are shown in FIG. 5A. In FIG. 5B, cell-free DNA from healthy controls is probed for the BRAF V600E variant. Note that all participants had at least one variant allele present at family size ≥1, and one participant had a variant allele up to a family size ≥13. In FIG. 5C, the KRAS G12D variant was probed in healthy controls and few variant alleles were identified.

Collectively, these findings demonstrate the true impact of size-based reduction of sample complexity to generate larger family sizes and improvement in both sensitivity through ctDNA enrichment and specificity through reduction in false positives. Such size-based selection of cell-free DNA generates larger family sizes during NGS applications. Data was shown that supports the impact of the methodology through reduction of false positives while maintaining and/or improving sensitivity. This technology is particularly useful in detecting very-low frequency (<1%) variants in cell-free DNA where false positives directly affect confidence of differentiating true variants from PCR and sequencing errors. Moreover, this technology has implications that extend beyond oncology. In particular, this methodology may have utility in non-invasive prenatal screening to improve detection and genotyping of fetal DNA, which has been shown to have a similar association with shorter cell-free DNA fragment sizes as described herein.

Example Study 2

In this study, a high-throughput-capable automated gel-extraction platform was optimized and implemented to isolate subfractions of the mononucleosomal peak in sequencing libraries of ccfDNA from patients with melanoma, colorectal adenocarcinoma, and pancreatic ductal adenocarcinoma with confirmed somatic BRAF or KRAS variants. The study sought to determine if selection of shorter ccfDNA fragments increased VAF of tumor-associated variants as detected by ddPCR and NGS. Also studied were the NGS data to identify the potential effects of size selection to reduce ccfDNA sample complexity for generating more PCR duplicates (i.e., larger family sizes). The effects of incrementally larger family sizes on the occurrence of false positives in the sequencing libraries from healthy controls was also investigated. Additionally, the patient-derived NGS libraries were analyzed to determine whether true VAF remained constant over a wide range of family sizes. In so doing, this study characterizes the potential of automated size-based selection of ccfDNA fractions to improve detection of ctDNA during NGS applications by simultaneously enriching for ctDNA and reducing false positives associated with PCR and sequencing errors.

The results of Study 2 support the automated selection of shorter ccfDNA fragments as a multifactorial approach to improve very low frequency ctDNA detection using NGS. Building upon the findings from lung cancer in Study 1, Study 2 used both ddPCR and NGS to extend to melanoma, colorectal adenocarcinoma, and pancreatic ductal adenocarcinoma the strengths of size selecting for short ccfDNA fragments to enrich for ctDNA. Furthermore, a high-throughput capable automated size selection technology was implemented that substantially improves the potential to translate these findings to broader research and clinical applications. Evidence was found that selection of short ccfDNA fragments enriches for ctDNA through isolation of fragment sizes containing a greater proportion of variant alleles, while concomitantly reducing wild type alleles that are more abundant at longer fragment lengths. Thus, for a given read depth the detection of ctDNA is more likely in the short ccfDNA fraction where the VAF is greatest. Finally, reduction of sample complexity through a priori size-based selection of ccfDNA generated larger family sizes for the subsequent in silico suppression of PCR and sequencing errors occurring at very low frequency. Size selection improved error correction through generation of larger family sizes without adversely affecting variant detection in the short ccfDNA fraction. Collectively, these findings identify the isolation of shorter ccfDNA fragments as a methodology to simultaneously improve both sensitivity and specificity of very low frequency ctDNA detection via NGS.

Investigation of ccfDNA size distribution originated in studies of maternal and fetal DNA in the plasma of pregnant women. As later confirmed for ctDNA, fetus-derived ccfDNA showed an increased occurrence of short fragments when compared to maternal ccfDNA with the predominant peak fraction at ~143-146 bp and a noted absence of dinucleosomal units. With a goal of increasing sensitivity of non-invasive prenatal testing, several studies were successful in moderately enriching for the fetal fraction of circulating DNA through preparative size separation by gel-electrophoresis or microsystem. However, the latter methodologies limited size selection to fragments <300 bp, effectively eliminating dinucleosomal and larger plasma DNA without achieving enrichment for the 143 bp fetal peak fraction over the 166 bp maternal component. For enrichment of ctDNA, we have previously used polyacrylamide gel electrophoresis to provide high-resolution manual extraction of targeted ccfDNA fractions. Although this approach enriched for ctDNA in a small cohort of patients with lung cancer, the methodology was cumbersome which limited scalability and broader use. In Study 2, it is demonstrated that high-resolution size-based fractionation to isolate sub-nucleosomal populations is technically feasible using a high-throughput-capable automated gel-extraction platform. Doing so extended the previous observations that selection of short ccfDNA fragments enriches for ctDNA in a broader array of cancer types, including at least melanoma, colorectal adenocarcinoma, and pancreatic ductal adenocarcinoma. Thus, a priori size selection of specific ccfDNA fractions may have greater translational clinical implications for fully harnessing the informational power of ccfDNA size differences in prenatal and cancer diagnostics.

In silico analysis is an alternative strategy to the a priori physical selection of shorter ccfDNA fragments. The incorporation of in silico size analyses of maternal plasma DNA content has facilitated identification of fetal content and diagnosis of fetal aneuploidies. More recently, ccfDNA fragment size has been integrated into in silico filtering algorithms to significantly improve the positive predictive value of second-generation prenatal fetal whole genome analysis. However, in silico size selection may not enable the potentially advantageous variant allele enrichment afforded by a priori physical ccfDNA fragment size selection. In accord, the approach described herein for enrichment may have the greatest use in the search for non-metastatic solid-tumors where ctDNA frequency is commonly <2%. Alternatively, use of in silico size selection in combination with physical size selection may further improve ctDNA detection through elimination of the longer fragments observed to migrate with the shorter targeted range. Isolation of short ccfDNA fractions did not adversely affect VAF by NGS. Although a greater variance in the calculated gain/loss factor was observed when VAF was determined by ddPCR, this finding was most pronounced for low VAF samples and may be attributable to the amount of library sampled. The ddPCR input of 50 ng comprises only ~1.5-2.5% of the total amount of library. Sampling errors can lead to exaggerated gain/loss results, particularly in low VAF samples where small numbers of under- or over-sampled copies can have dramatic effects on VAF. In contrast, 500 ng (15-25% of total library) were used for hybrid capture and subsequent NGS, likely leading to a more robust estimation of VAF gain/loss factor achieved in each size fraction.

The use of unique molecular identifiers improve ctDNA specificity. Although duplex molecular barcoding (the assignment of unique molecular identifiers to both strands of DNA) has a very high theoretical potential to reduce sequencing and PCR errors, the associated low ligation efficiency (10-20%) has limited applications seeking to detect very low frequency ctDNA variants due to sample loss. As an alternative, unique molecular identifier performance has been enhanced with error modeling derived from healthy control data substantially reducing false positives, particularly during searches of known variants. Error modeling achieves comparable error reduction as using a barcoded family size ≥5 alone. Error modeling may be advantageous as generation of large family sizes has been previously described to lead to a similar loss in sample as duplex molecular barcoding. It is shown in Study 2 that a priori physical size selection of ccfDNA generated larger family sizes and selection for the short ccfDNA fraction enabled continued successful detection of known variants with a VAF ≥0.39% at a family size ≥20 and an average read depth of ~516×. However, using the same sequencing parameters in future investigations may not allow detection at lower VAFs due to the progressive reduction in read depth associated with increments in family size. This was evident in the unselected ccfDNA where the lower VAF, increased sample complexity, and reduced read depth at larger family sizes led to loss of variant detection. Thus, selecting a sufficient read depth for a targeted VAF within the context of using family size data for in silico error correction can overcome this potential issue. It is noteworthy that the analysis in Study 2 found persistence of stochastic errors even at the largest family sizes with a frequency in the range consistent with very low frequency ctDNA variants (0.1%<VAF<1%). As such, error modeling alone may not completely eliminate false positives during untargeted searches of ctDNA. Collectively, these observations support the conjecture that unique molecular identifiers, a priori physical size selection of short ccfDNA fragments, and sufficient read depth will improve variant detection in early-stage non-metastatic solid tumors or low-frequency aggressive clones in advanced cancers not only through ctDNA enrichment, but also by improving in silico error correction through production of larger family sizes.

In addition to size selection of ccfDNA, alternative methods may also improve sensitivity and specificity of ctDNA detection at various steps in the process of generating NGS data. Using a reduced amount of input ccfDNA at library preparation potentially reduces sample complexity and improves generation of larger family sizes. The range of input ccfDNA from patients in this study was 10-56.6 ng (mean: 20.1±14.5 ng) derived from the greater of 10 ng or 1 mL of plasma ccfDNA equivalent. Although variants down to a VAF of 0.39% at a mean read depth of ~5,500× at FS≥1 were identified, using less input material may adversely affect sensitivity, particularly for detection of variants with an even lower VAF where using more starting material may be advantageous to minimize type II error due to sampling. Increasing the read depth has the potential to achieve both larger family sizes and greater sensitivity. In this study, a similar number of total reads was used across all samples to evaluate the effects of selecting for subfractions of ccfDNA. Using a larger number of total reads may not achieve a uniform increase in sensitivity and family size between samples as the effect would be less in samples of greater complexity. Thus, evaluating sensitivity and family size within the context of varying sample complexity can be used to determine optimal read depth for a desired VAF. In silico analysis using more stringent criteria (i.e., fraction of bases supporting the consensus call, higher quality scores, etc.) may also be an effective approach to reduce false positives. For example, in the present study an alignment score of MQ≥20 and base score Q≥20 with >0.66 concordance between bases was used during consensus identification. Increasing these values may improve specificity, but at the risk of adverse effects on sensitivity. Additionally, PCR-based methods using molecular barcodes represent an alternative approach to the capture-based NGS methods used in this stud. While amplicon-based sequencing panels can be useful for querying a small number of mutational hotspots, they rely on consistent amplification of all target sequences in a multiplex PCR step. Therefore, the ability to customize or expand panels by addition of primer pairs is limited. In addition, due to the highly fragmented nature of ccfDNA, amplicon-based approaches can only account for ccfDNA molecules containing intact amplicons, while hybridization probes potentially capture additional unique ccfDNA molecules. Also, hybridization capture sequencing panels can range from small, targeted panels to whole exome or whole genome coverage and size selection has the potential to benefit ctDNA detection using any size panel. Overall, each approach has strengths and weaknesses. A balance between cost, sensitivity, and specificity needs strong consideration when designing a study and determining utility of each method or combination of methods. In this study, automated size-based selection of ccfDNA was found to support both sensitivity and specificity. However, costs associated with labor, equipment, and reagents merit strong consideration prior to integration of size selection for ccfDNA subfractions into a research and clinical laboratory workflow.

Preparation of libraries for physical size selection and NGS is accomplished using a multi-step process with multiple rounds of PCR amplification. A direct comparison of ctDNA VAFs determined by ddPCR in ccfDNA and by multi-step NGS in captured ccfDNA libraries indicated that detectable VAFs were not adversely affected by the NGS methodology used in this study. Although a reduced association for VAF <1.5% by ddPCR was not observed, this may be attributable to sample size as both the highest (1.31%) and lowest (0.39%) VAF by ddPCR within this subset were increased in the NGS data (2.3% and 0.78%, respectively). A similar comparison of VAFs by sequencing of ccfDNA libraries and by direct ddPCR of the corresponding plasma DNA has been reported. While such also demonstrated a high correlation of NGS and ddPCR, VAFs in NGS were generally lower (~2×) than those detected directly by ddPCR. A similar drift was not observed in VAF. This suggests that conversion of ctDNA and non-tumor ccfDNA fragments into NGS libraries may be biased against ctDNA in certain methods of library preparation. Evidence that such bias could at least in part be accounted for by the size difference in non-tumor versus tumor-derived fragments is provided by a previous study which demonstrated that the choice of library preparation method directly influences representation of shorter or damaged ccfDNA molecules. In the present study, however, evidence of bias against ctDNA during NGS library preparation was not observed. Rather, it was found that both WT and variant counts observed by NGS were similar to expected NGS counts using ddPCR data as a reference. The similarities in count number between ddPCR and NGS suggests losses are associated with both approaches. Thus, methods that reduce loss with either technique may further improve overall sensitivity.

Example of Size Selection for Short ccfDNA Fragments Enriches for ctDNA

VAFs in ccfDNA Determined by ddPCR and NGS are Strongly Correlated

Figure 6A:
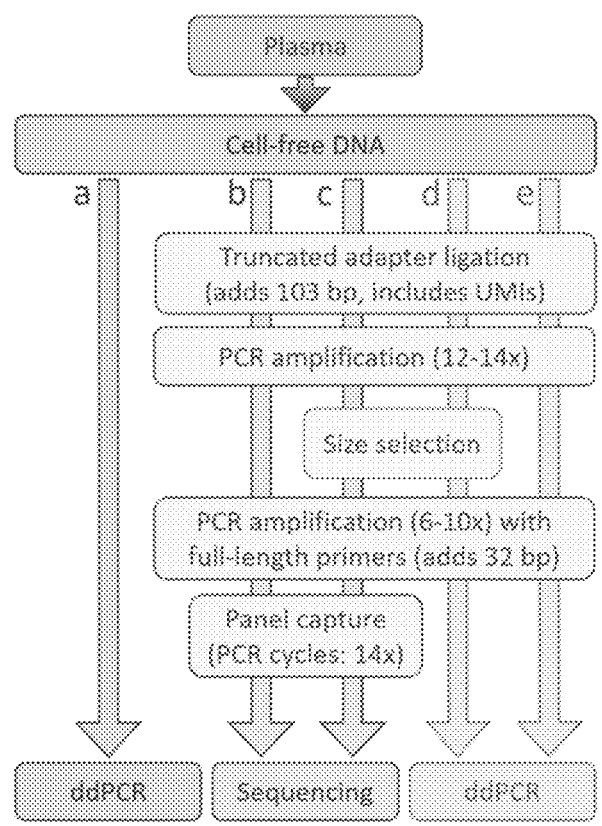
FIG. 6A illustrates steps in process flows prior to determination of variant allele frequency in accordance with an example embodiment.
Figure 6B:
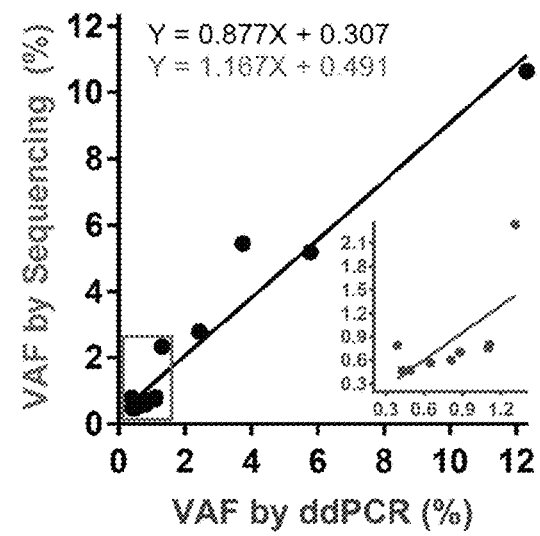
FIG. 6B provides data showing a correlation between direct measurement of variant allele frequency in ccfDNA by ddPCR (flow a) and by the multi-step sequencing process (flow b) in accordance with an example embodiment.

High-resolution size selection of ccfDNA libraries prior to sequencing involves multiple PCR amplification steps, as is shown in the example of FIG. 6A. It was initially determined whether the library preparation process or subsequent PCR amplification steps result in drift of the detectable VAF. Samples from 13 patients with a BRAF or KRAS variant present in solid tumor tissue from melanoma (N=8), colorectal adenocarcinoma (N=3), or pancreatic ductal adenocarcinoma (N=2) and a corresponding quantifiable variant present in ccfDNA by droplet digital PCR (ddPCR) were analyzed (Table 1). ddPCR performed on ccfDNA prior to ligation of adapters and library formation determined VAF (FIG. 6A) and facilitated direct molecular counting of amplifiable unique wild type (WT) and variant counts (FIGS. 7A-E). After addition of truncated adapters with unique molecular identifiers, subsequent extension to full-length adapters, panel capture, and multiple PCR amplification steps, WT counts, variant counts, and VAF were determined by NGS (FIG. 6A). Each NGS count (either WT or variant) for all reported results hereafter is an aligned consensus read derived from PCR duplicates with the same unique molecular identifier. Thus, each count represents a single unique molecule from the original ccfDNA sample prior to library PCR amplification. To evaluate for losses associated with NGS, WT and variant counts obtained from ddPCR were extrapolated to determine the expected number of WT and variant counts from NGS assuming a lossless system for a given amount of ccfDNA library input. There was a significant correlation between the extrapolated ddPCR counts and NGS counts for WT alleles (Pearson's r=0.72, P=0.005) and variant alleles (r=0.96, P<0.001). For both WT and variant counts an increased number of counts was detected by NGS over ddPCR for most of the samples. That difference was statistically significant for the WT alleles (57.5±86.7%, P=0.034; FIG. 8A), but not variant alleles (77.1±162.9%, P=0.11; FIG. 8B). Undercalling of ddPCR is likely a reflection of the requirement of detectable DNA fragments to contain intact amplicon regions. Such non-amplifiable alleles may be detectable by NGS after hybrid capture. Conversely, loss of allele counts detectable by NGS could be a consequence of inefficient adapter ligation, post ligation cleanup, or non-uniform hybrid capture. While both methods may be subject to losses and regardless of absolute count differences, the VAF was strongly correlated between ddPCR and NGS (r=0.97, P<0.001; FIG. 6B). In the subset of samples with VAF <1.5% by ddPCR the association persisted (r=0.68, P=0.046; FIG. 6B, inset). Thus, sample preparation and analysis by NGS used in this study did not adversely affect VAF in ccfDNA as corroborated by ddPCR.

TABLE 1

Demographics and variant allele frequency (VAF).

| ID | Cancer Type | Age, yrs | Gender | Stage | Allele | VAF by ddPCR, % |
|---|---|---|---|---|---|---|
| C1 | Colorectal | 69 | M | IV | KRAS G13D | 12.26 |
| C2 | Colorectal | 78 | F | III | BRAF V600E | 2.43 |
| C3 | Colorectal | 63 | M | IV | KRAS G12D | 0.65 |
| M1 | Melanoma | 49 | F | IIIC | BRAF V600E | 0.81 |
| M2 | Melanoma | 80 | F | IIIC | BRAF V600K | 1.11 |
| M3 | Melanoma | 53 | F | IV | BRAF V600E | 0.39 |
| M4 | Melanoma | 45 | M | III | BRAF V600E | 1.31 |
| M5 | Melanoma | 67 | F | IV | BRAF V600E | 3.74 |
| M6 | Melanoma | 67 | M | IV | BRAF V600K | 0.88 |
| M7 | Melanoma | 39 | M | IV | BRAF V600E | 5.78 |
| M8 | Melanoma | 50 | M | IV | BRAF V600K | 1.10 |
| P1 | Pancreatic | 63 | M | IV | KRAS G12D | 0.48 |
| P2 | Pancreatic | 54 | F | IV | KRAS G12V | 0.43 |

FIG. 6A shows a process flow depicting steps prior to determination of variant allele frequency (VAF). With known variants, VAF can be determined directly from ccfDNA with ddPCR (flow a), while sequencing requires a multi-step process (flow b). The addition of truncated adapters followed by extension to full-length in separate steps (flows b-e) is done to improve resolution during size selection (flows c, d) of desired subfractions of ccfDNA. There was a strong association (FIG. 6B) between direct measurement of VAF in ccfDNA by ddPCR (FIG. 6A, flow a) and by the multi-step sequencing process (FIG. 6A, flow b). This association was present even at VAFs <1.5% (FIG. 6B inset). The equations for each colored regression line are shown in a corresponding color. In (FIG. 6C), boxplots of wild type alleles and variant alleles by NGS are shown for each cancer patient (C=colorectal adenocarcinoma; M=melanoma; P=pancreatic ductal adenocarcinoma). In (FIG. 6C), data are only shown for insert sizes ≤250 to focus results on the mononucleosome as that length approximates the midpoint between the mononucleosome and dinucleosome lengths associated with ccfDNA. The horizontal line identifies the median insert size (167 bp) from all patients. In the majority of patients, the median insert size of the tumor-associated variant allele was shorter than the corresponding wild type allele.

FIGS. 7A-E show detection of variant alleles by ddPCR in ccfDNA. Plasma ccfDNA was isolated from 13 cancer patients with confirmed solid tumor variants in BRAF or KRAS (Table 1). Between 7 and 46 ng of ccfDNA was analyzed, depending on the concentration of cell-free DNA in the plasma. Positive control samples were generated from commercial standards (Horizon Discovery; HD701: BRAF V600E, KRAS G13D; HD239: BRAF V600K; HD272: KRAS G12D; HD289: KRAS G12V) and sheared to mimic cell-free DNA size distribution. Cell-free DNA extracted from the plasma of healthy controls and water were included as wildtype-only and no-template assay controls, respectively. Primary ddPCR data plots and gated areas generated by the RD Analyst software are shown. Gates for wildtype and variant droplet clusters were set using positive control samples and subsequently applied to negative controls and patient samples. The shown variant allele frequency was calculated from the observed droplet counts. Variant copy number per milliliter plasma was extrapolated based on effective analyzed reaction volume, DNA input volume, total extract volume and total plasma volume extracted.

FIGS. 8A-B show wild type (WT) and variant allele (VA) counts by ddPCR and NGS. The ddPCR WT (FIG. 8A, x-axis) and VA (FIG. 8B, x-axis) counts were derived from ddPCR data and represent the extrapolated number of counts expected to be seen by NGS assuming a lossless system for a given amount of ccfDNA library input. In both FIGS. 8A and 8B, the solid line is the line of unity. In FIG. 8B, the inset is a magnification identified by the box. The legend identifies counts associated with each variant.

Automated Size Selection Reproducibly Isolated ccfDNA Subfractions

Figure 6C:
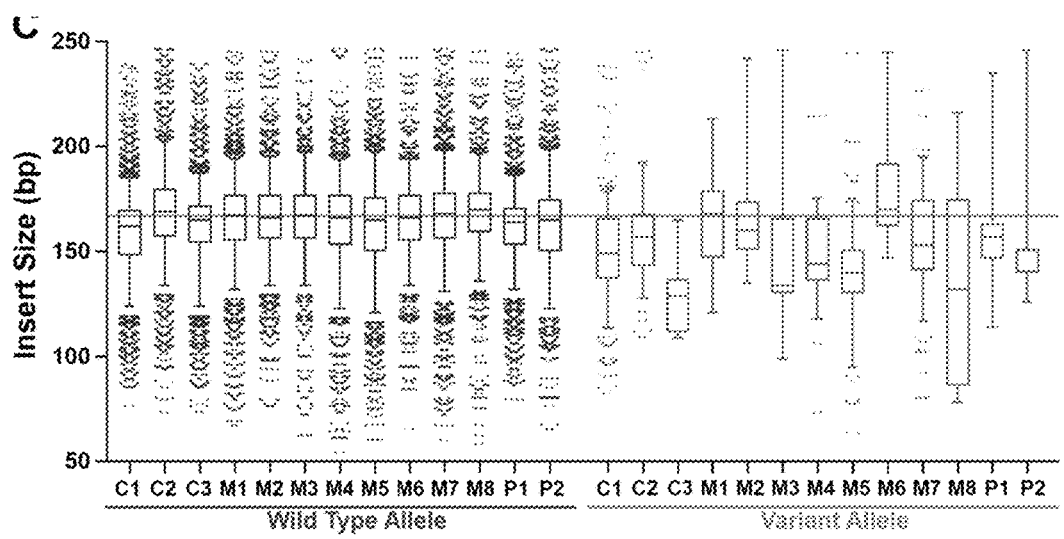
FIG. 6C illustrates data in boxplots of wild type alleles and variant alleles by NGS for each cancer patient (C=colorectal adenocarcinoma; M=melanoma; P=pancreatic ductal adenocarcinoma) in accordance with an example embodiment.
Figure 7A:
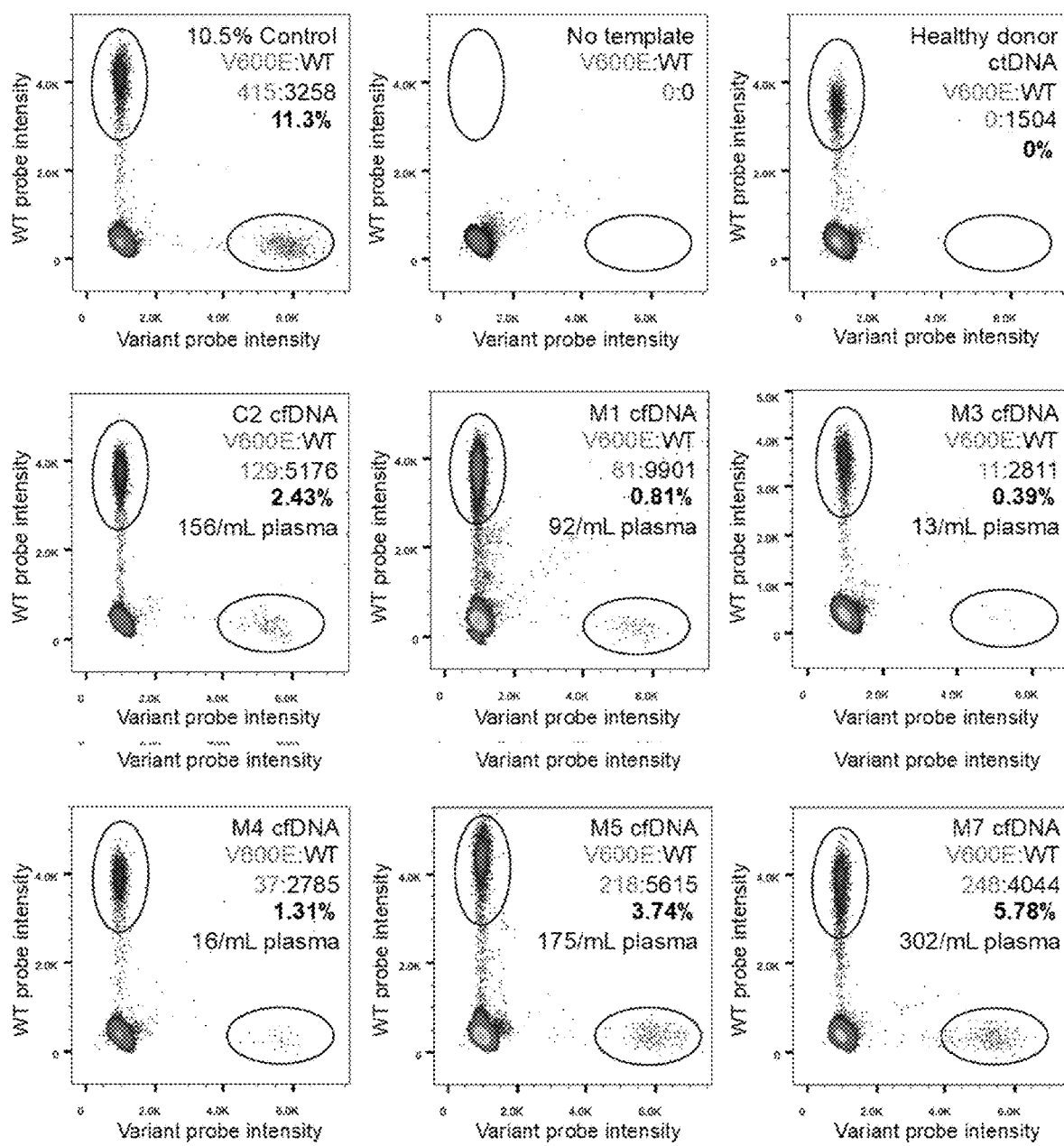
FIG. 7A illustrates data relating to the detection of variant alleles by ddPCR in ccfDNA in accordance with an example embodiment.
Figure 7B:
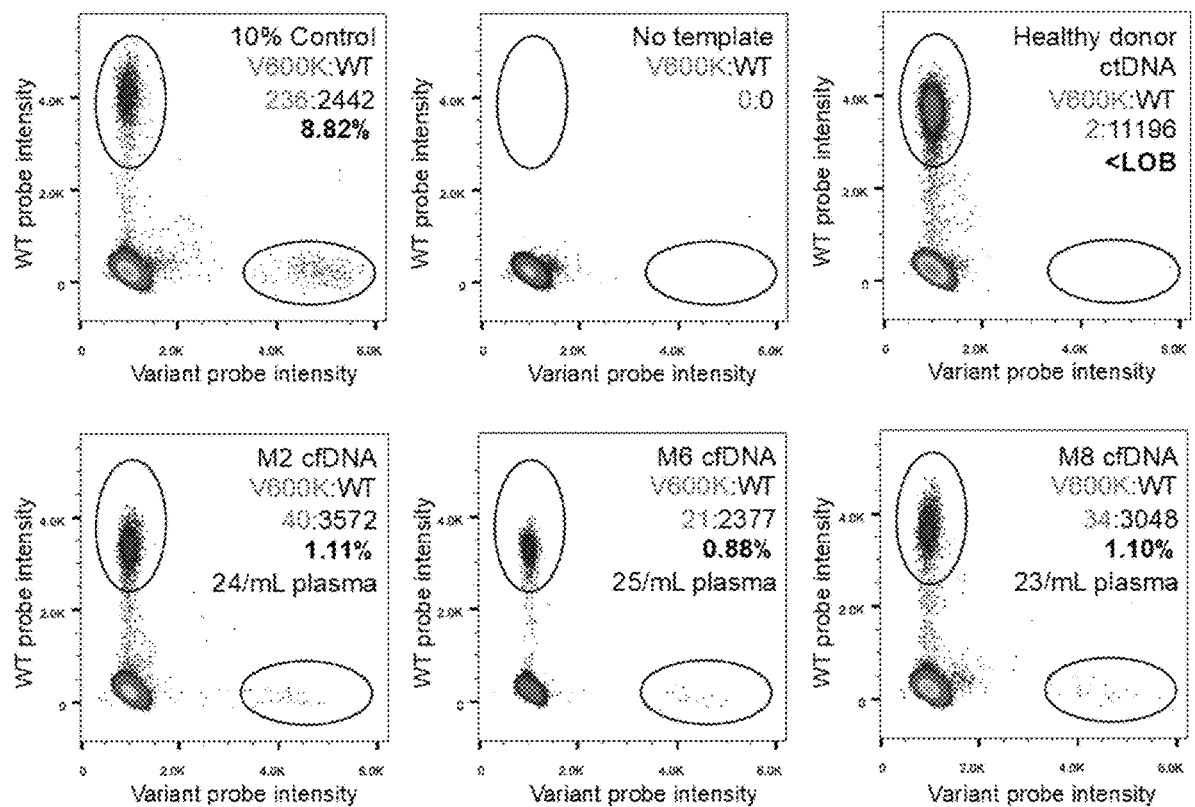
FIG. 7B illustrates data relating to the detection of variant alleles by ddPCR in ccfDNA in accordance with an example embodiment.
Figure 7C:
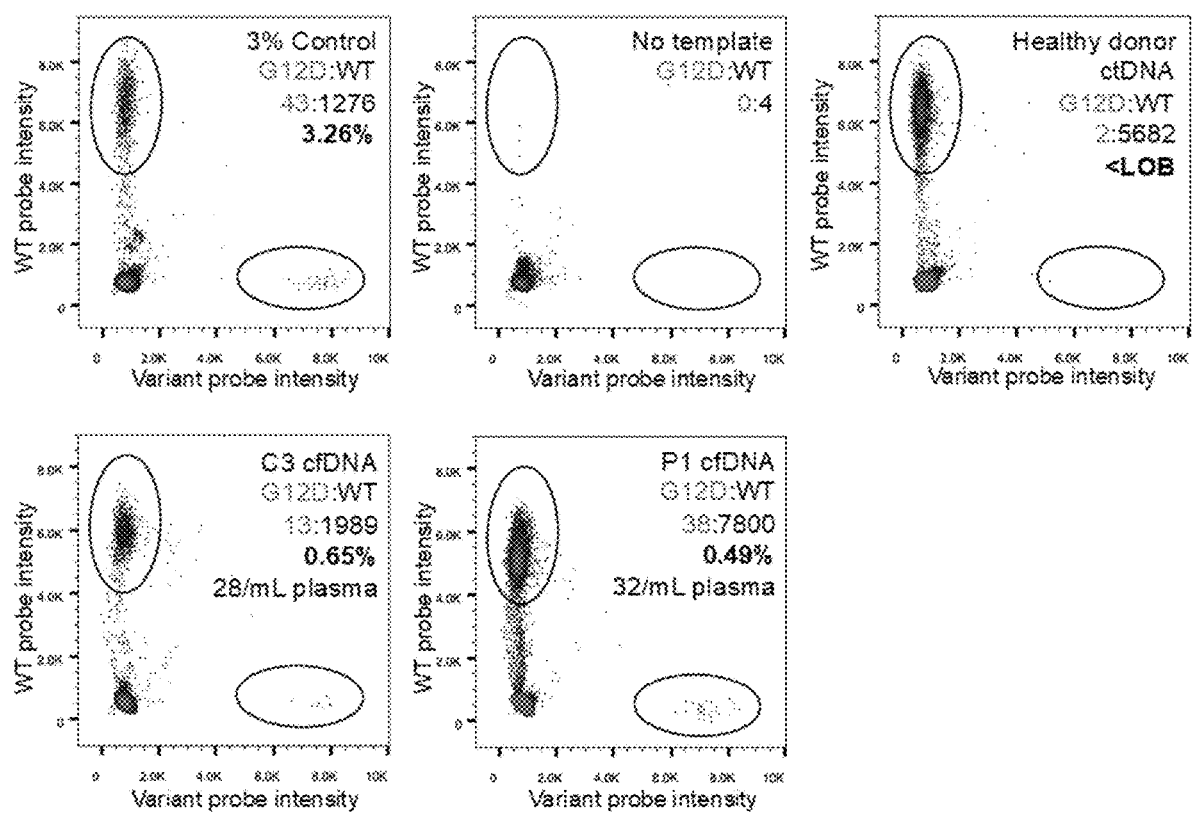
FIG. 7C illustrates data relating to the detection of variant alleles by ddPCR in ccfDNA in accordance with an example embodiment.
Figure 7D:
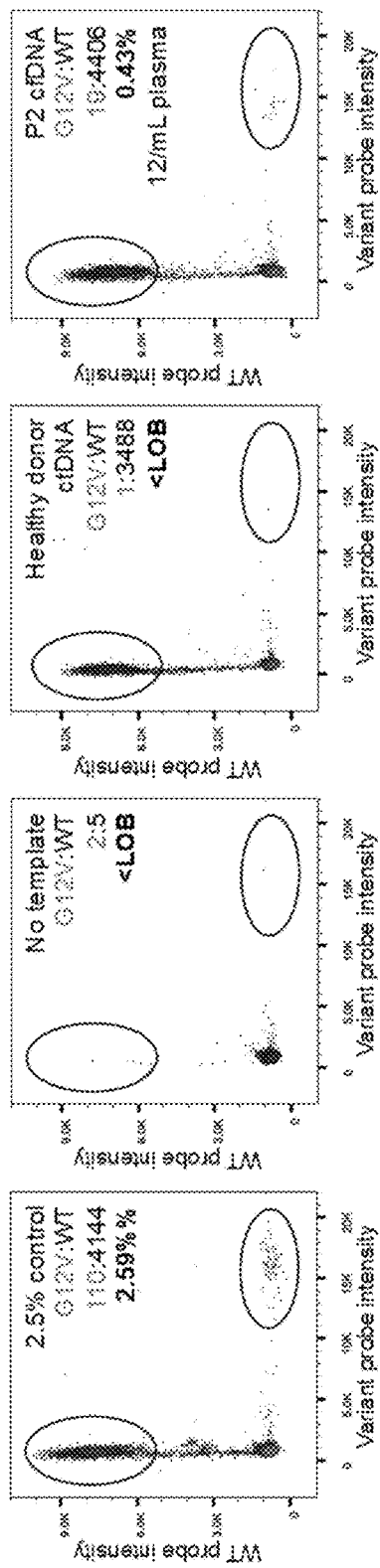
FIG. 7D illustrates data relating to the detection of variant alleles by ddPCR in ccfDNA in accordance with an example embodiment.
Figure 7E:
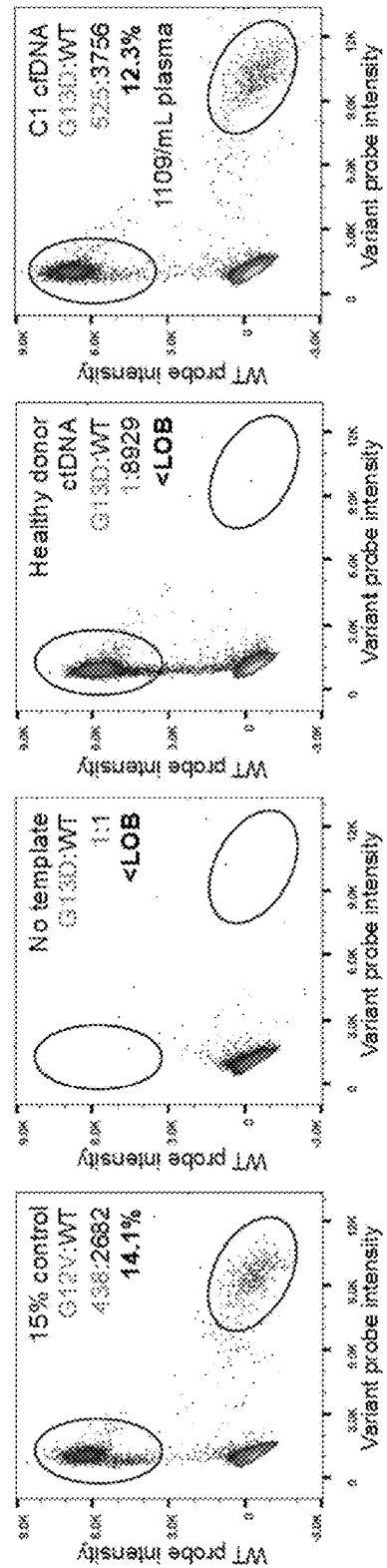
FIG. 7E illustrates data relating to the detection of variant alleles by ddPCR in ccfDNA in accordance with an example embodiment.
Figure 9:
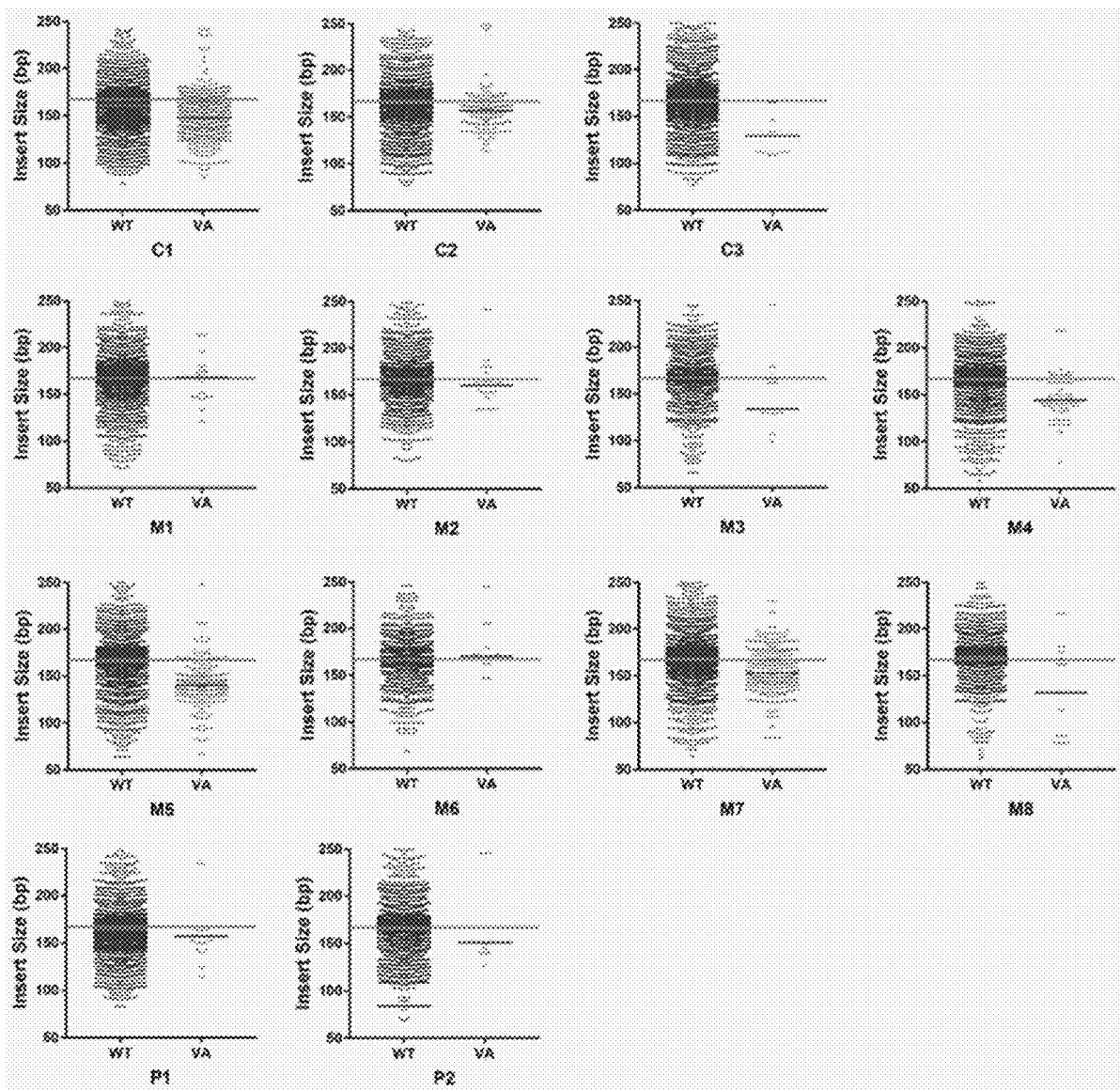
FIG. 9 illustrates data in beeswarm plots for insert sizes <250 bp associated with the wild type (WT) and variant allele (VA) from each patient in accordance with an example embodiment.

In EGFR-mutant lung cancer samples, VAF increases in association with shorter ccfDNA fragments. In 13 patients it was observed that the median insert sizes corresponding to the mononucleosome (<250 bp) associated with the variant alleles present in either BRAF or KRAS were generally shorter than the corresponding wild type alleles (151.8±12.8 vs. 166.9±2.5 bp, respectively; P=0.001; FIG. 6C). Individual beeswarm plots for each patient for both WT and variant are shown in FIG. 9 (insert size <250 bp, mononucleosome) and FIG. 10 (insert size >250 bp, dinucleosome and larger). In order to enrich for variant alleles, an automated agarose gel-based extraction method was optimized and tested for the consistent selection of size-based ccfDNA fractions (FIGS. 11A-B). Subsequently, enrichment capabilities of gel-based ccfDNA fragment size selection were established using pooled ccfDNA from healthy controls spiked with synthetic EGFR T790M fragments (length 130 bp) and BRAF V600E fragments (length 165 bp) at similar VAF. Truncated adapters were added, PCR amplified to produce libraries of spiked and unspiked ccfDNA, and then mixed to yield an eight sample dilution series of unselected spiked ccfDNA libraries with VAFs ranging from 0.01% to 13.1% as measured by ddPCR (FIG. 12A-D). Short and long fractions were then extracted from 1 µg of PCR-amplified truncated ccfDNA libraries to target the EGFR and BRAF spike-in variants, respectively. Full-length libraries were generated from size-selected fractions and VAF was determined by ddPCR (FIG. 12A-D). Isolation of the short fraction increased VAF of the EGFR T790M variant (130 bp) in each dilution (FIG. 11C). There was a strong association between dilution factor and enrichment (Pearson's r=0.92, P=0.009; FIG. 11D) indicating greatest enrichment occurred at the lowest VAF. The EGFR T790M variant was absent in the long fraction (FIG. 11C). The VAF of the BRAF V600E variant (165 bp) was consistently greater than the unselected VAF in both the short and long fractions (FIG. 11E), but the extent of enrichment remained relatively constant across all dilutions (FIG. 11F). As such, the enrichment observed for the 165-bp BRAF V600E variant was likely due to elimination of wildtype BRAF found in the dinucleosomal and larger plasma DNA components. Collectively, these findings characterize electrophoretic mobility of ccfDNA under the prescribed experimental conditions. Specifically, for a given size of ccfDNA the distribution is not fully Gaussian. For a targeted size range, longer rather than shorter fragments outside the desired range are more likely to be present as exemplified by the absence of the EGFR T790M variant (130 bp) in the long fraction and the presence of the BRAF V600E variant (165 bp) in the short fraction. This is further shown in the densitometry plots where a tail of longer fragment sizes is present in the short fraction (FIG. 11A, arrow). These results also support the automated agarose gel-based extraction method for reproducibly and accurately separating subpopulations of the mononucleosomal ccfDNA component after NGS library preparation.

FIG. 9 shows beeswarm plots for insert sizes <250 bp associated with the wild type (WT) and variant allele (VA) from each patient. The solid gray line corresponds to the overall median insert size from all patients of 167 bp. The solid light or dark blue line for WT or VA identifies the corresponding median insert size for that patient. In some instance it is not visible (e.g., M1) as it is behind the gray line. The identifiers under each plot are matched to Table 1 and FIG. 2C. C=colorectal adenocarcinoma; M=melanoma; P=pancreatic ductal adenocarcinoma.

Figure 10:
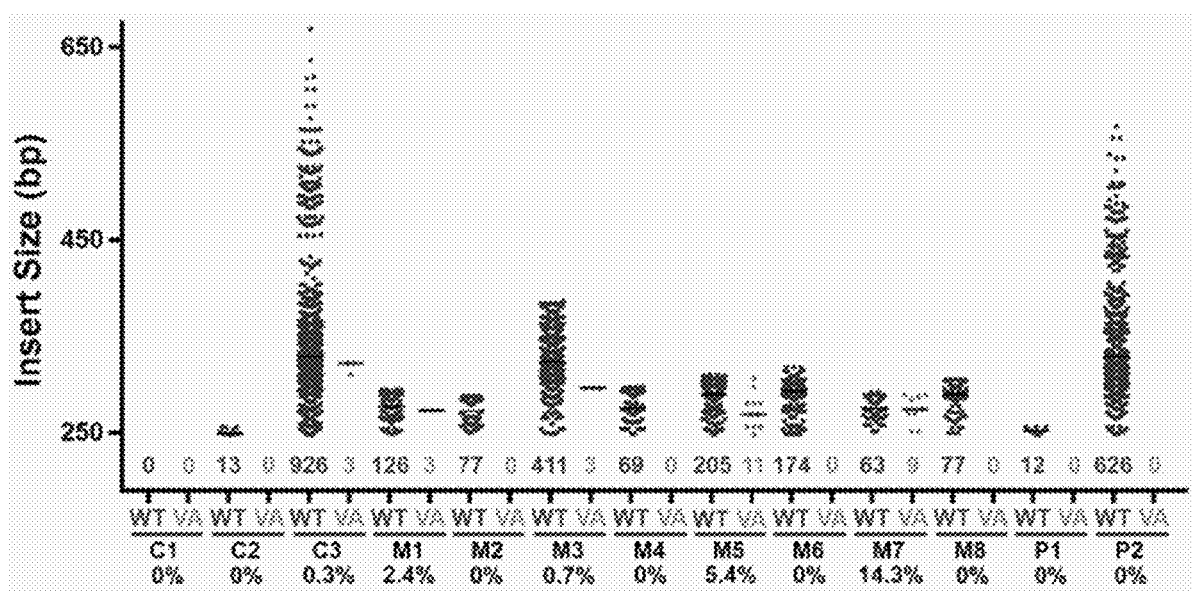
FIG. 10 illustrates data in beeswarm plots for insert sizes >250 bp associated with the wild type (WT) and variant allele (VA) from each patient in accordance with an example embodiment.
Figure 11A:
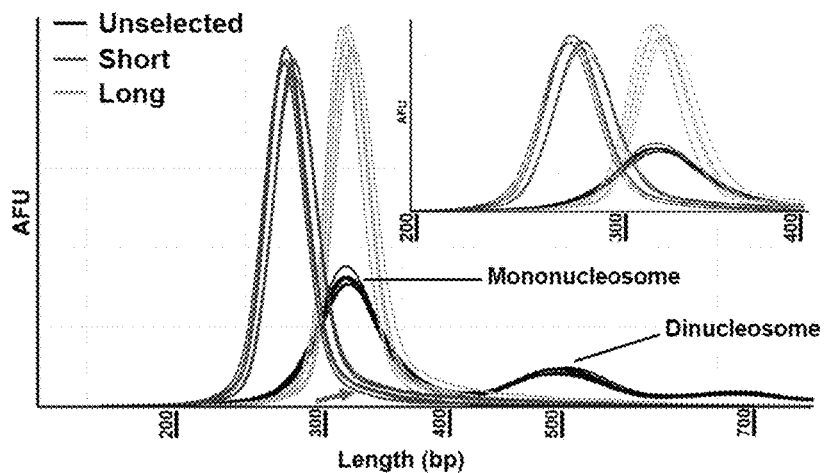
FIG. 11A illustrates data relating to the effect of size selection on VAF in spiked ccfDNA libraries in accordance with an example embodiment.
Figure 11B:
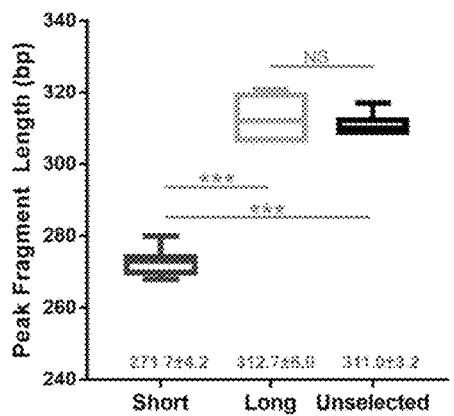
FIG. 11B illustrates data relating to the effect of size selection on VAF in spiked ccfDNA libraries in accordance with an example embodiment.
Figure 11C:
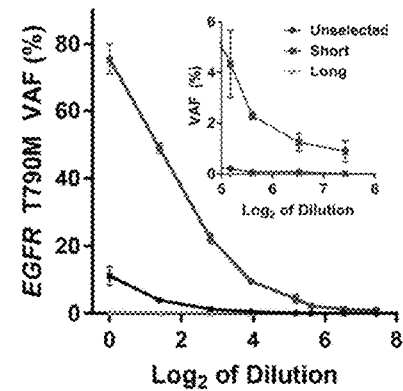
FIG. 11C illustrates data relating to the effect of size selection on VAF in spiked ccfDNA libraries in accordance with an example embodiment.
Figure 11D:
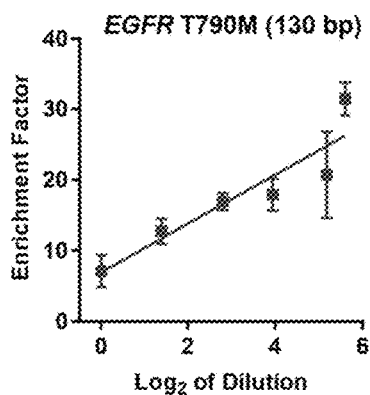
FIG. 11D illustrates data relating to the effect of size selection on VAF in spiked ccfDNA libraries in accordance with an example embodiment.

FIG. 10 shows beeswarm plots for insert sizes >250 bp associated with the wild type (WT) and variant allele (VA) from each patient. Absence of data (e.g., C1) indicates that an allele with an insert size >250 bp was not detected for that patient. The solid black line for WT or VA identifies the median insert size. The dark blue and light blue numbers identify the total number of counts for WT and VA, respectively. The identifiers under each plot are matched to Table 1 and FIG. 2C. The percentages under each identifier indicate VAF using insert sizes >250 bp. C=colorectal adenocarcinoma; M=melanoma; P=pancreatic ductal adenocarcinoma.

Figure 11E:
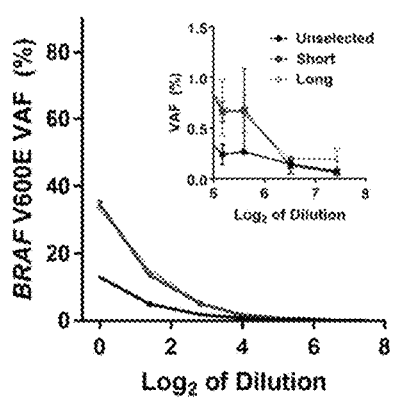
FIG. 11E illustrates data relating to the effect of size selection on VAF in spiked ccfDNA libraries in accordance with an example embodiment.
Figure 11F:
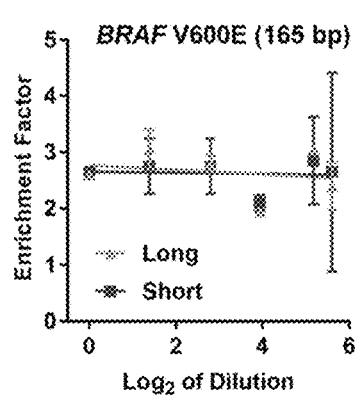
FIG. 11F illustrates data relating to the effect of size selection on VAF in spiked ccfDNA libraries in accordance with an example embodiment.
Figure 12A:
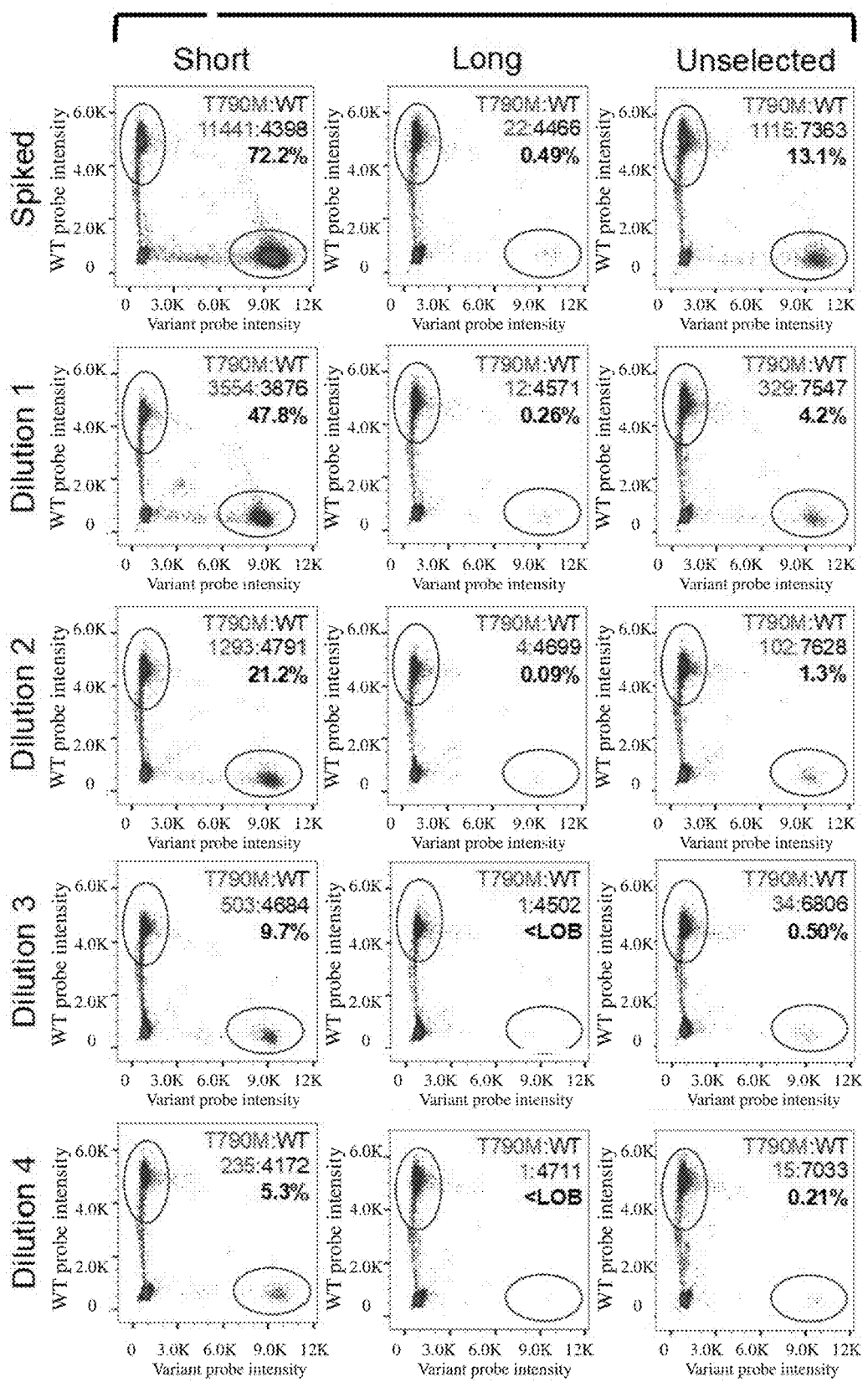
FIG. 12A illustrates data showing VAFs detected by ddPCR of size-selected and unselected synthetically spiked ccfDNA libraries in accordance with an example embodiment.
Figure 12B:
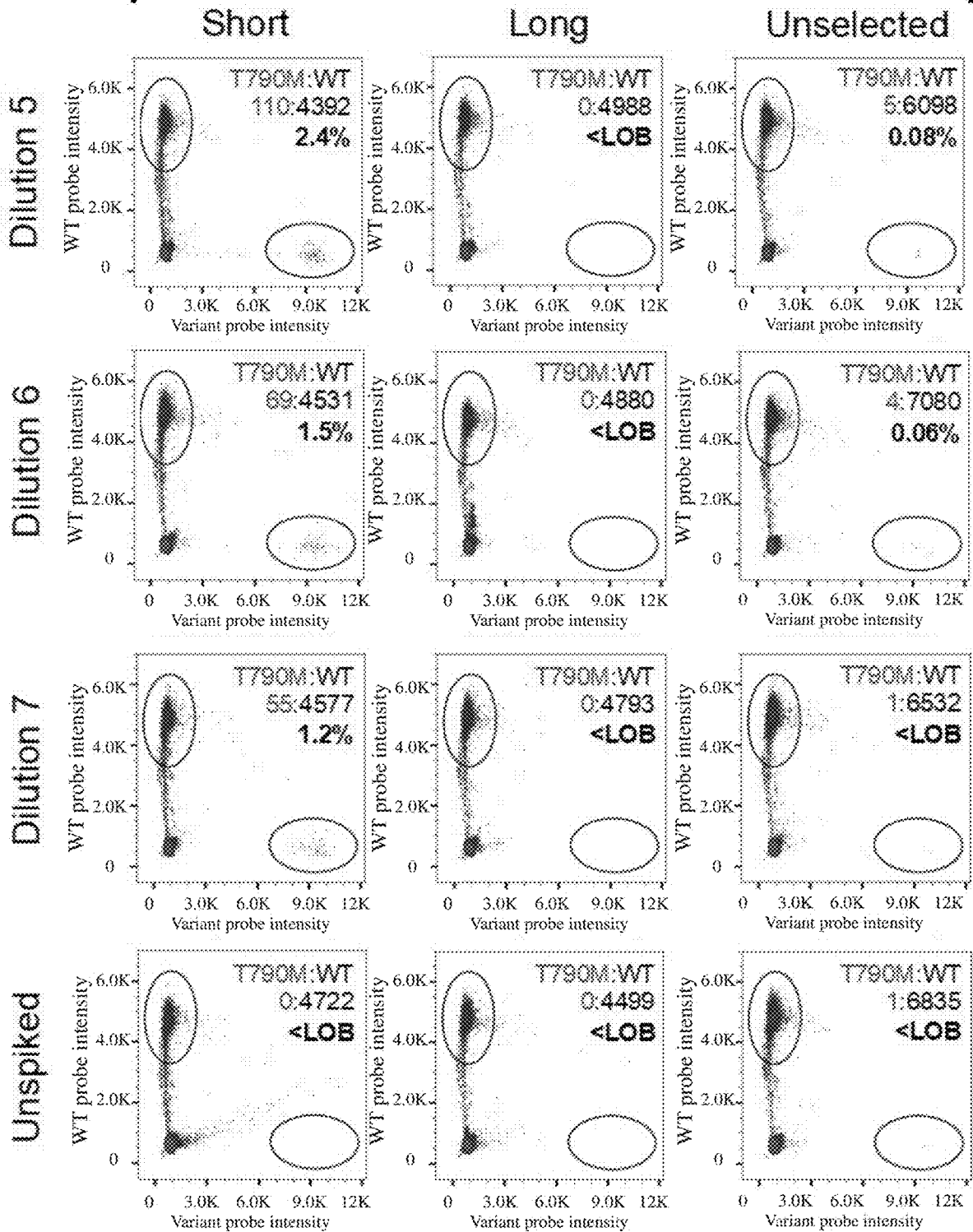
FIG. 12B illustrates data showing VAFs detected by ddPCR of size-selected and unselected synthetically spiked ccfDNA libraries in accordance with an example embodiment.
Figure 12C:
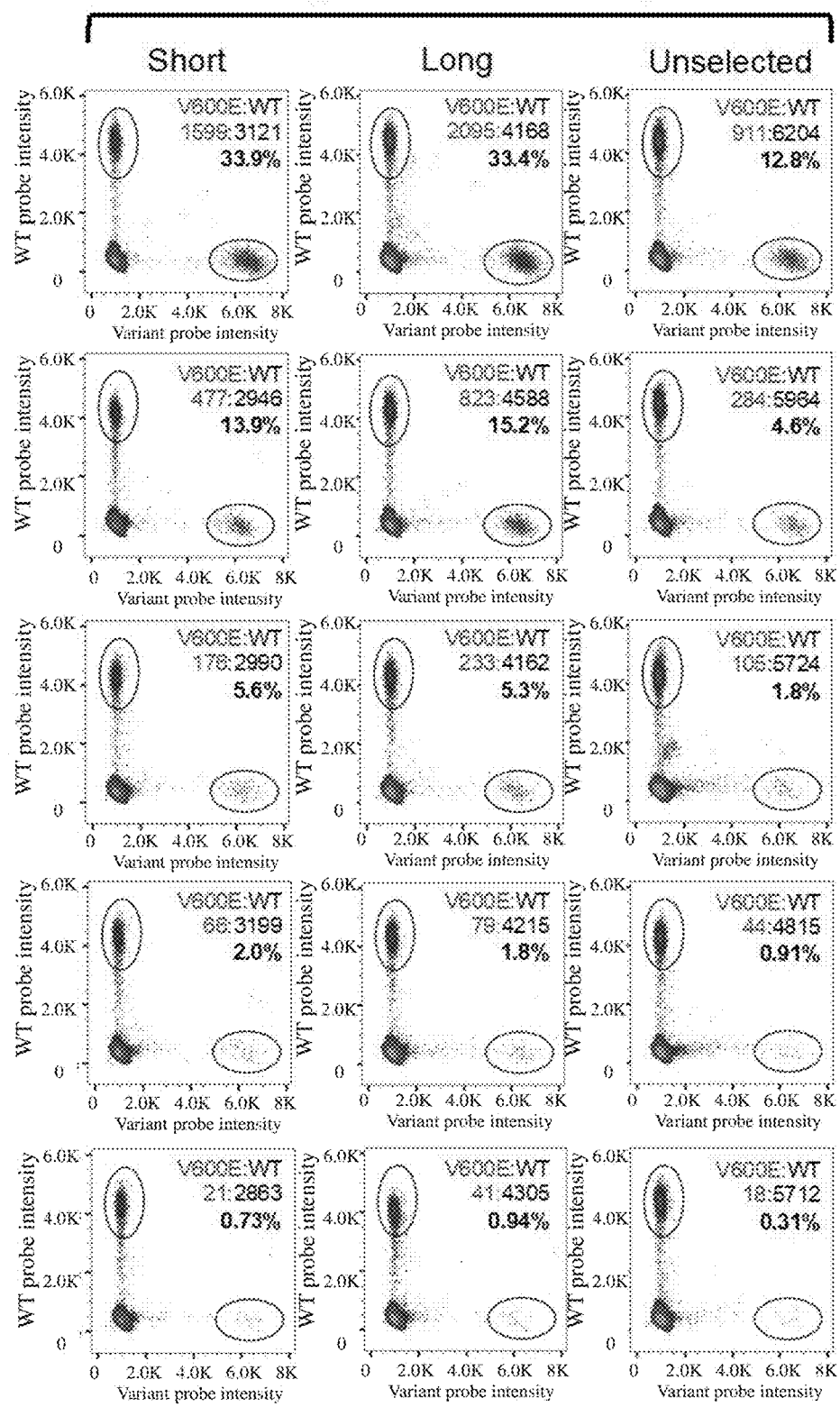
FIG. 12C illustrates data showing VAFs detected by ddPCR of size-selected and unselected synthetically spiked ccfDNA libraries in accordance with an example embodiment.
Figure 12D:
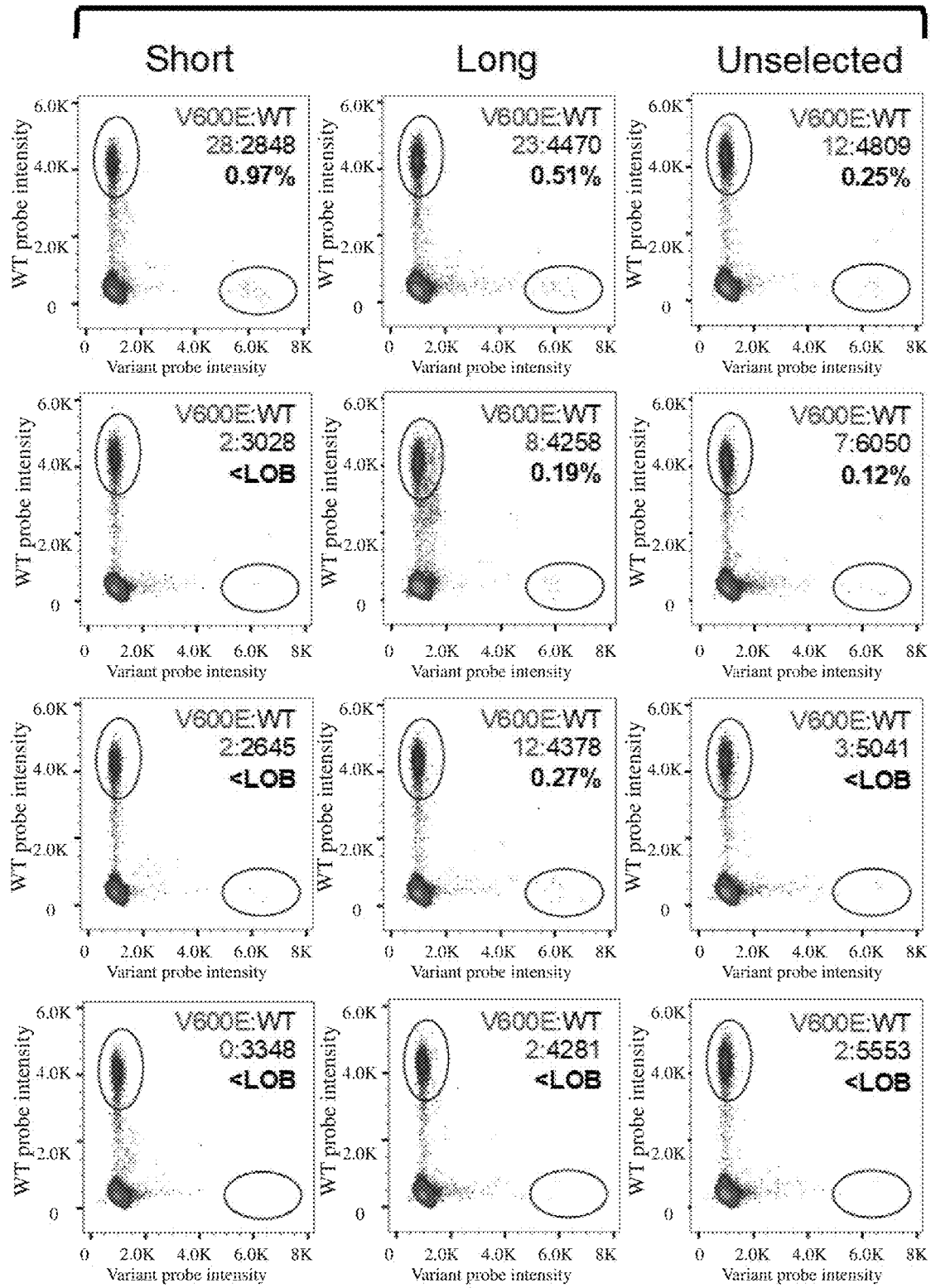
FIG. 12D illustrates data showing VAFs detected by ddPCR of size-selected and unselected synthetically spiked ccfDNA libraries in accordance with an example embodiment.

FIGS. 11A-F show the effect of size selection on VAF in spiked ccfDNA libraries. Isolation of targeted ccfDNA fractions using a high-throughput automated gel-extraction platform. Distribution by densitometry of the short (purple) and long (orange) fractions isolated from healthy control unselected ccfDNA samples (black; N=7) is shown in FIG. 11A. Size includes full-length adapters (~135 bp). Note the evidence of a tail in the short fraction (blue arrow) consistent with longer fragments migrating with a shorter target fragment size. Although the overall distributions overlapped, the peak fragment length of the short fraction was significantly less than the long fraction (FIG. 11B). No significant difference was measured between the peak fragment lengths of the long fraction and the unselected mononucleosome (FIG. 11B). Gray numbers indicate the mean±SD peak fragment length for each sample (FIG. 11B). VAF determined by ddPCR for the EGFR T790M synthetic spike (130 bp) for the short (purple) and long (orange) fractions and the unselected ccfDNA (black) are graphed in FIG. 11C. In the short fraction the T790M allele remained detectable even when it was undetectable in unselected ccfDNA (FIG. 11C, inset), while it was virtually absent from the long fraction regardless of dilution. The enrichment factor in the 'small' fraction was associated with extent of dilution with the greatest amount of enrichment occurring in the most diluted samples (FIG. 11D; data only shown when unselected ccfDNA VAF was above the limit of blank by ddPCR). VAF by ddPCR for the BRAF V600E synthetic spike (165 bp) is shown in FIG. 11E. Overall, there was a general trend towards enrichment in both the short (FIG. 11E, purple) and long (FIG. 11E, orange) fractions. The variant was present throughout the short samples except at the lowest dilutions (FIG. 11E, inset). Extent of enrichment was relatively consistent regardless of dilution (FIG. 11F). In FIGS. 11A-D, error bars indicate standard deviation from independent duplicate experiments. *** P<0.001; NS=not significant; AFU=arbitrary fluorescent unit.

FIGS. 12A-D shows VAFs detected by ddPCR of size-selected and unselected synthetically spiked ccfDNA libraries. Pooled normal ccfDNA was spiked with 130-bp EGFR T790M and 165-bp BRAF V600E synthetic gBlocks® and truncated libraries were prepared from the spiked sample and its unspiked reference pool. After creation of an eight-step dilution series of spiked with unspiked controls, the spiked libraries and unspiked reference were size selected. Full-length libraries were subsequently prepared from unselected samples and short and long gel fractions. VAF for 130-bp EGFR T790M and 165-bp BRAF V600E was detected by ddPCR using 50 ng of full-length library.

Effect of Size Selection on VAF in Spiked ccfDNA Libraries Using an Automated Gel-Extraction Platform.

Distribution by densitometry of the short (purple) and long (orange) fractions isolated from healthy control unselected ccfDNA samples (black; N=7) is shown in (FIG. 11A). Size includes full-length adapters (~135 bp). Note the evidence of a tail in the short fraction (FIG. 11A, arrow) consistent with longer fragments migrating with a shorter target fragment size. Although the overall distributions overlapped, the peak fragment length of the short fraction was significantly less than the long fraction (FIG. 11B). No significant difference was measured between the peak fragment lengths of the long fraction and the unselected mononucleosome (FIG. 11B). Gray numbers indicate the mean±SD peak fragment length for each sample (FIG. 11B). VAF determined by ddPCR for the EGFR T790M synthetic spike (130 bp) for the short (purple) and long (orange) fractions and the unselected ccfDNA (black) are graphed in (FIG. 11C). In the short fraction the T790M allele remained detectable even when it was undetectable in unselected ccfDNA (FIG. 11C, inset), while it was virtually absent from the long fraction regardless of dilution. The enrichment factor in the 'small' fraction was associated with extent of dilution with the greatest amount of enrichment occurring in the most diluted samples (FIG. 11D; data only shown when unselected ccfDNA VAF was above the limit of blank by ddPCR). VAF by ddPCR for the BRAF V600E synthetic spike (165 bp) is shown in (FIG. 11E). Overall, there was a general trend towards enrichment in both the short (FIG. 11E, purple) and long (FIG. 11E, orange) fractions. The variant was present throughout the short samples except at the lowest dilutions (FIG. 11E, inset). Extent of enrichment was relatively consistent regardless of dilution (FIG. 11F). In A-D, error bars indicate standard deviation from independent duplicate experiments. *** P<0.001; NS=not significant; AFU=arbitrary fluorescent unit.

Automated Selection of Shorter ccfDNA Fragments Increased VAF

Figure 13A:
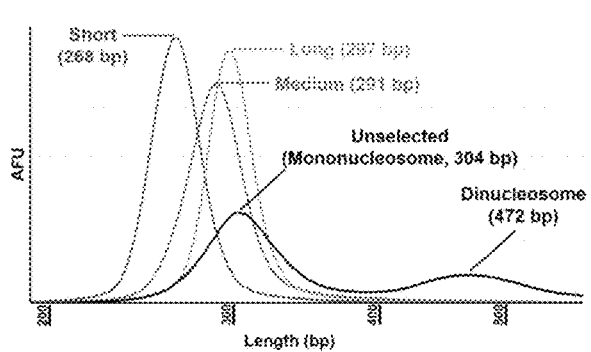
FIG. 13A illustrates data relating to the enrichment of variant alleles in short ccfDNA fractions in accordance with an example embodiment.
Figure 13B:
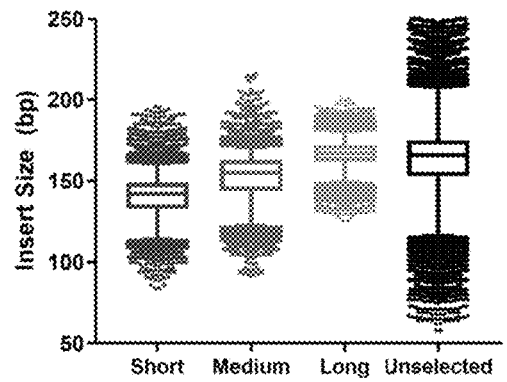
FIG. 13B illustrates data relating to the enrichment of variant alleles in short ccfDNA fractions in accordance with an example embodiment.
Figure 13C:
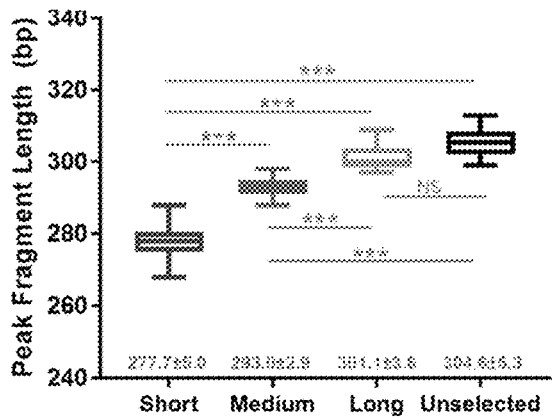
FIG. 13C illustrates data relating to the enrichment of variant alleles in short ccfDNA fractions in accordance with an example embodiment.
Figure 13D:
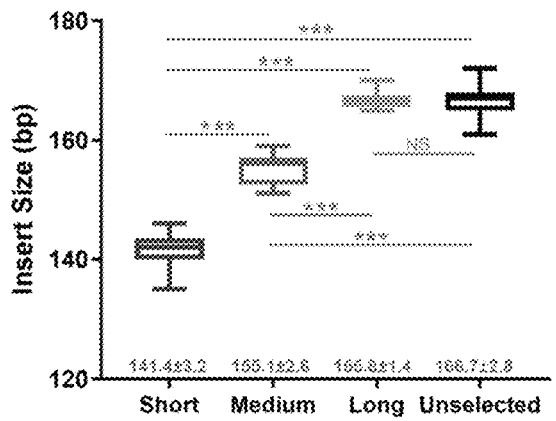
FIG. 13D illustrates data relating to the enrichment of variant alleles in short ccfDNA fractions in accordance with an example embodiment.
Figure 13E:
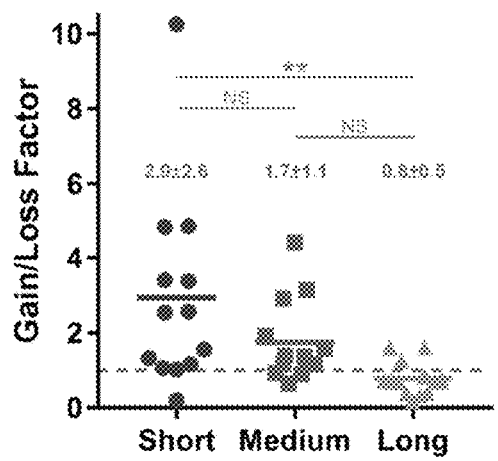
FIG. 13E illustrates data relating to the enrichment of variant alleles in short ccfDNA fractions in accordance with an example embodiment.
Figure 13F:
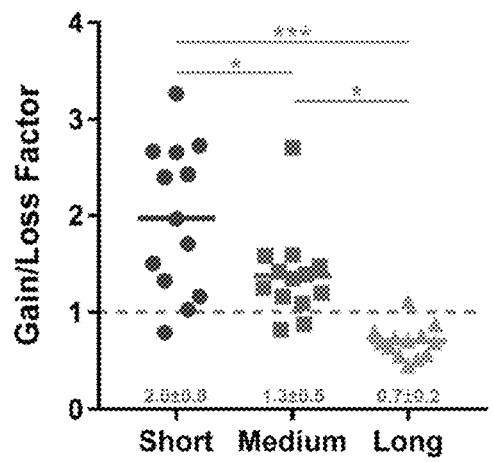
FIG. 13F illustrates data relating to the enrichment of variant alleles in short ccfDNA fractions in accordance with an example embodiment.
Figure 14A:
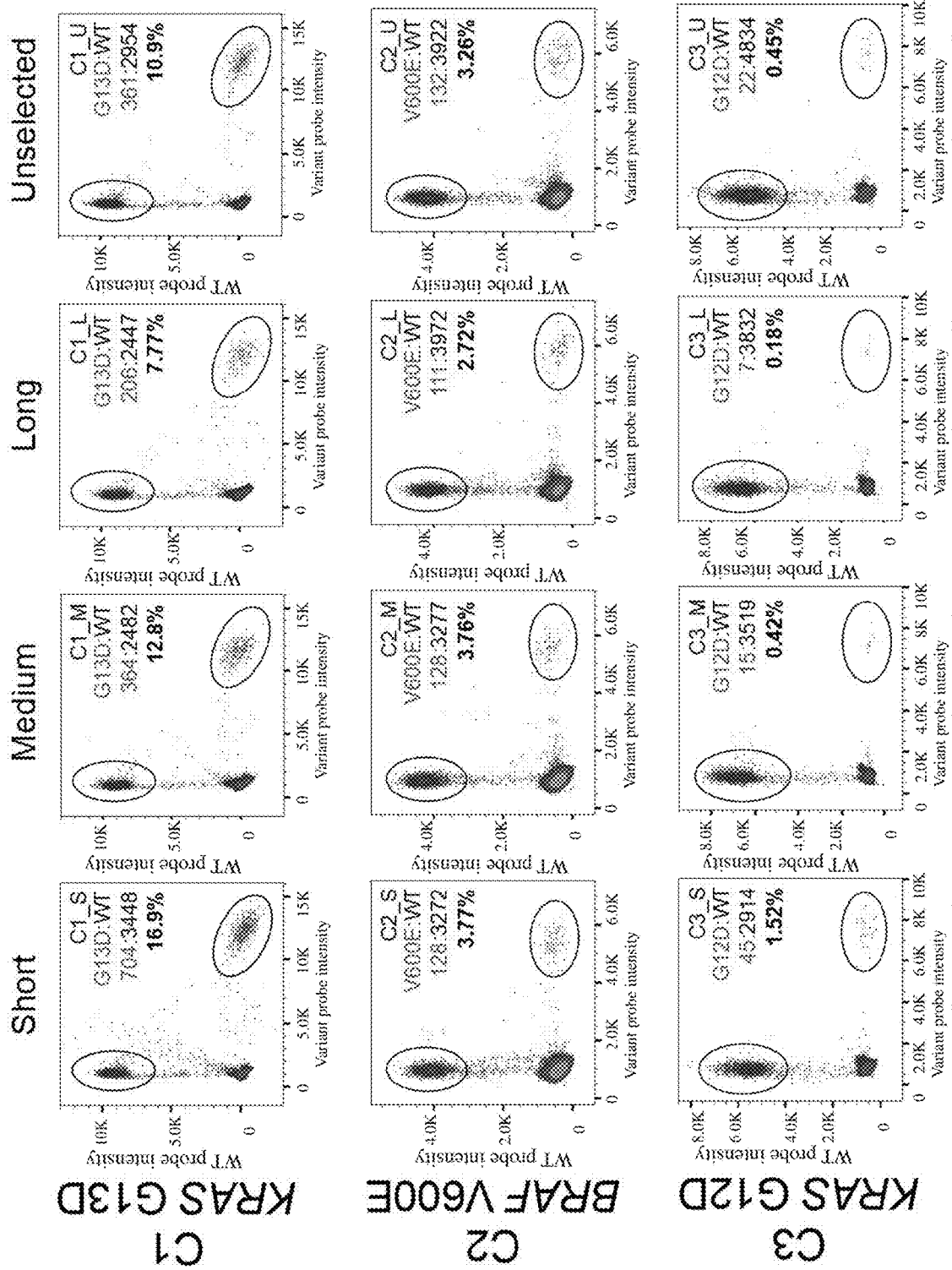
FIG. 14A illustrates data for VAF by ddPCR in size-selected ccfDNA libraries in accordance with an example embodiment.
Figure 14B:
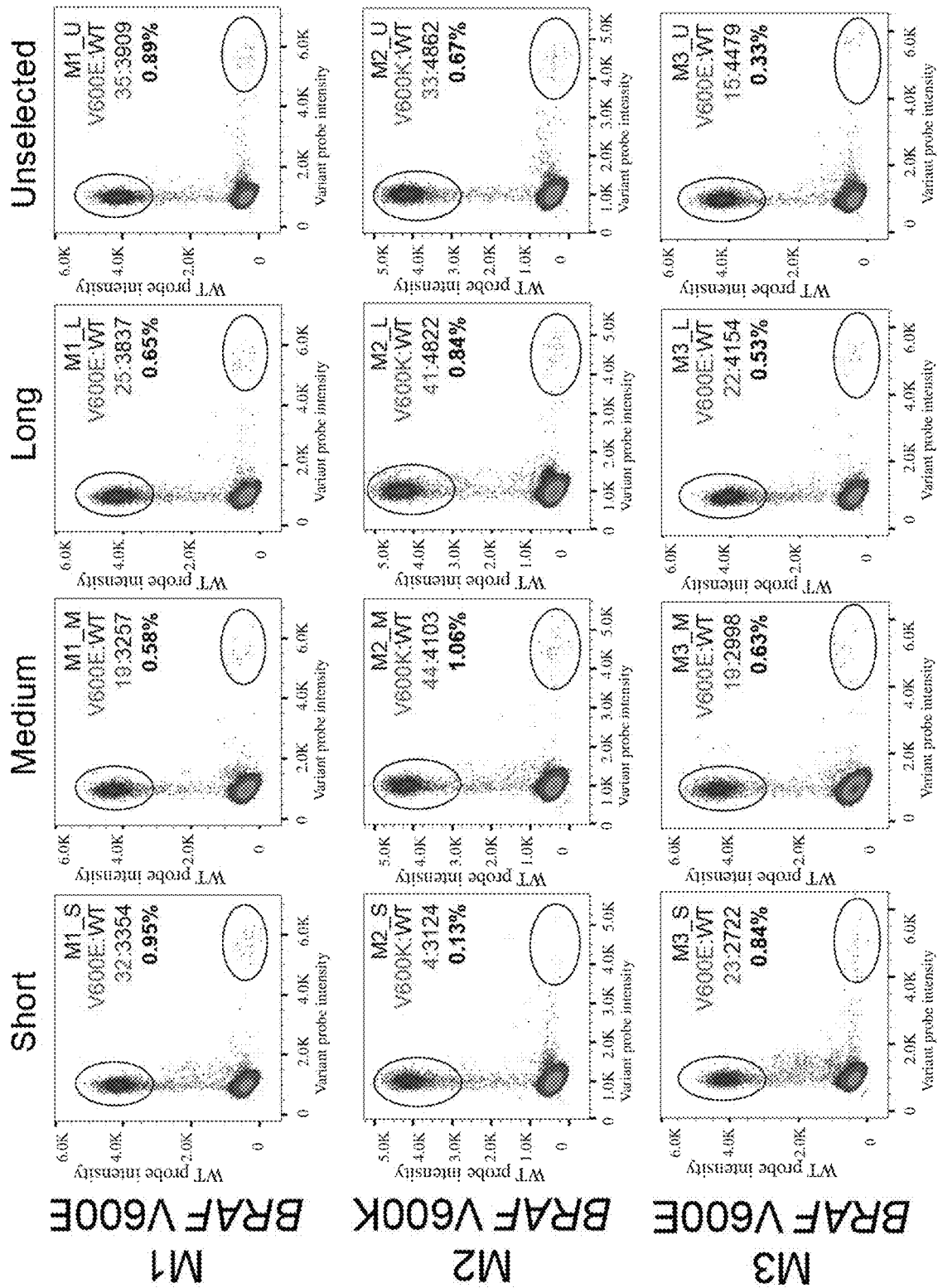
FIG. 14B illustrates data for VAF by ddPCR in size-selected ccfDNA libraries in accordance with an example embodiment.
Figure 14C:
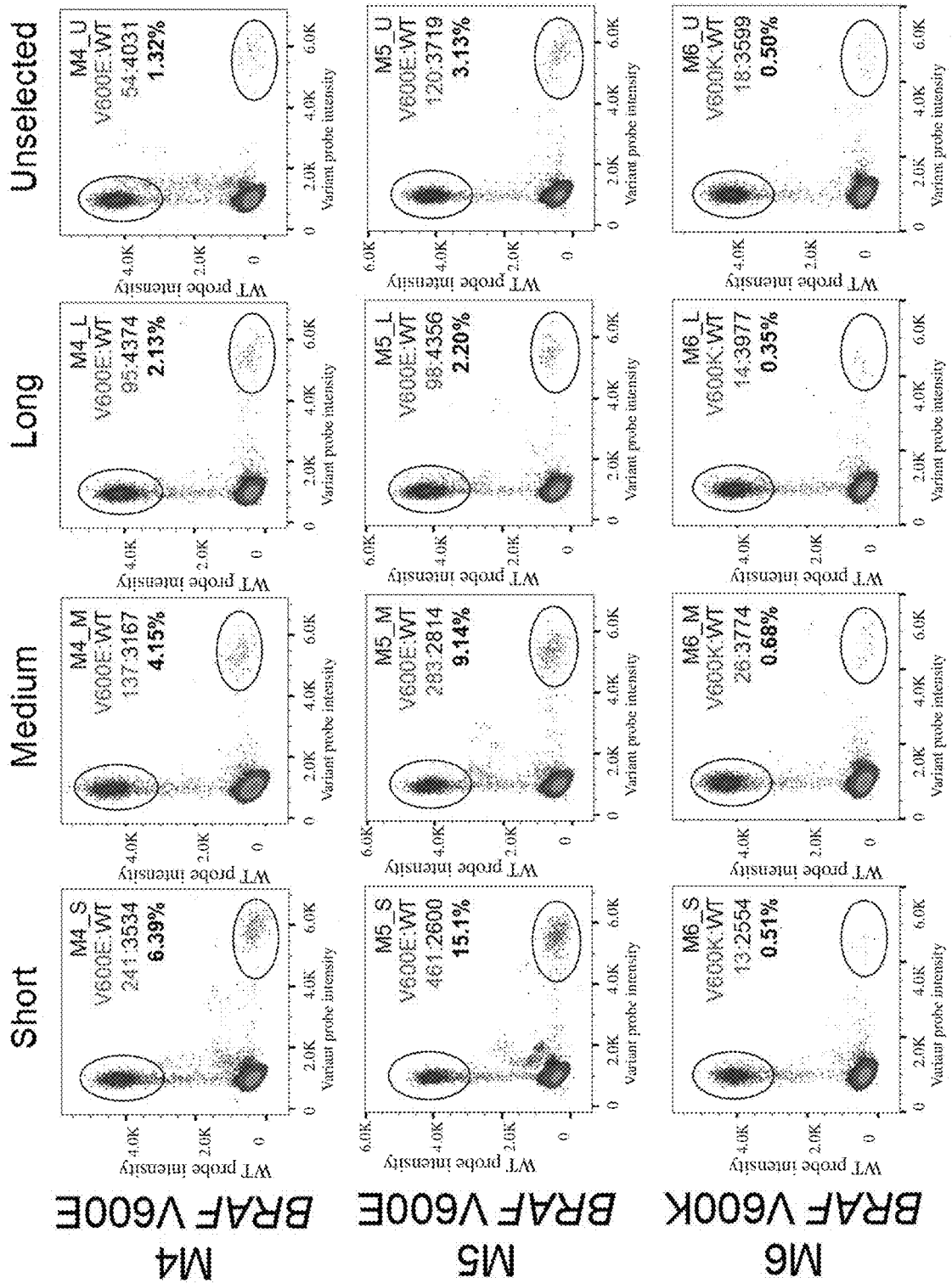
FIG. 14C illustrates data for VAF by ddPCR in size-selected ccfDNA libraries in accordance with an example embodiment.
Figure 14D:
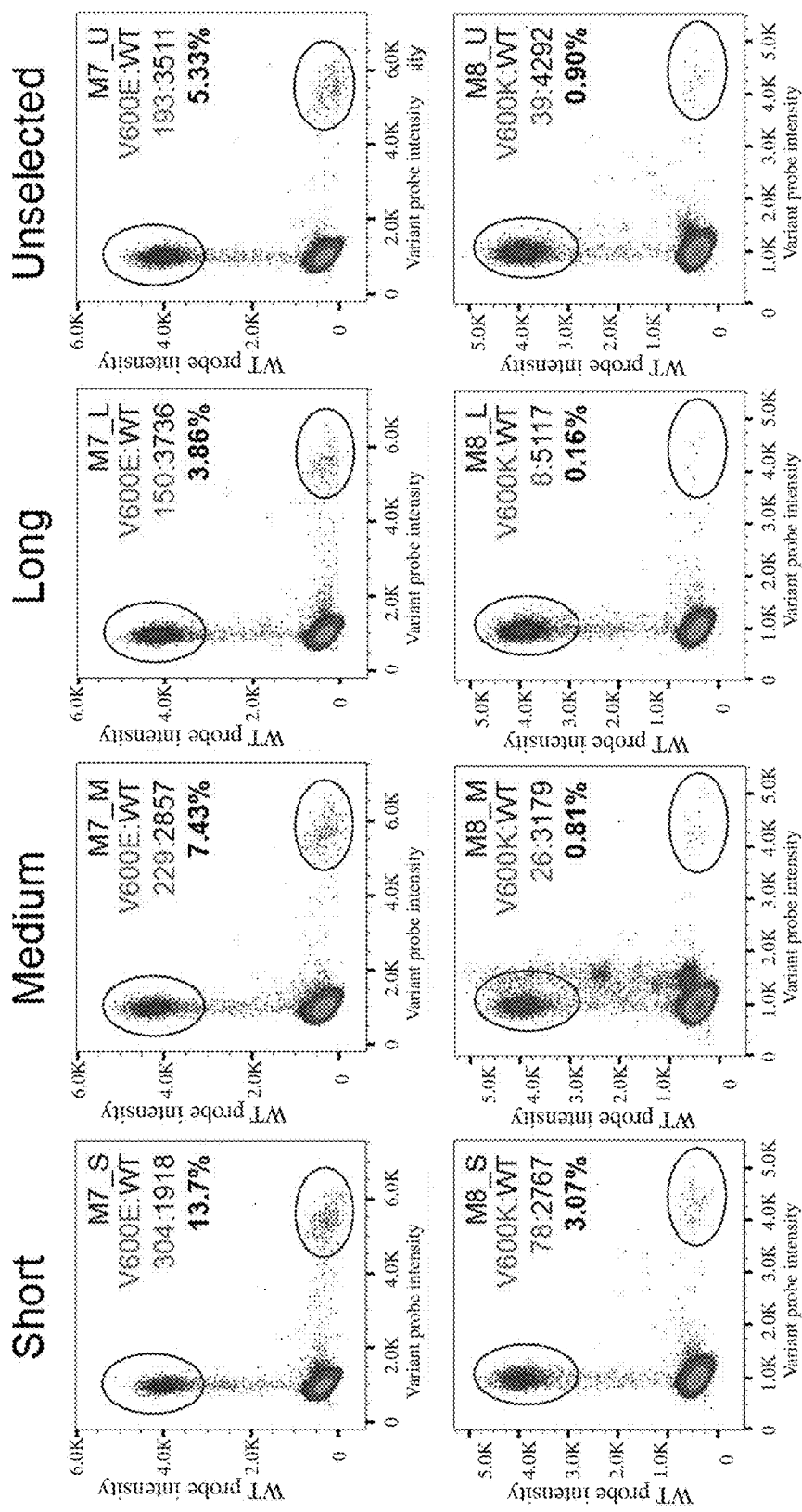
FIG. 14D illustrates data for VAF by ddPCR in size-selected ccfDNA libraries in accordance with an example embodiment.
Figure 14E:
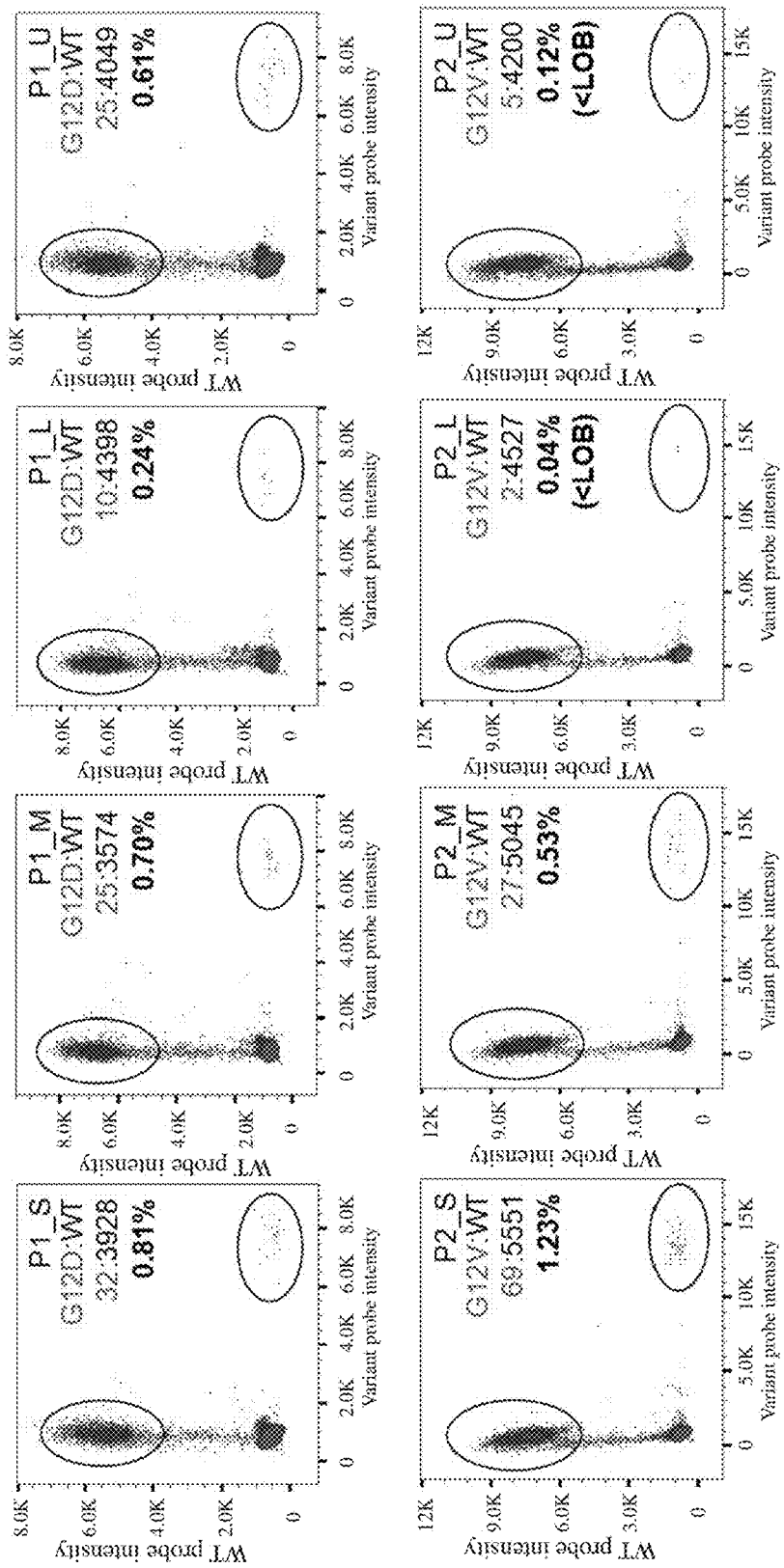
FIG. 14E illustrates data for VAF by ddPCR in size-selected ccfDNA libraries in accordance with an example embodiment.

Size-based fractions were then isolated from the ccfDNA of patients with solid tumors (Table 1) to characterize the effects on VAF as quantified by both ddPCR and NGS. Both short and long fractions were extracted from PCR-amplified truncated ccfDNA libraries (1 µg; FIG. 13A). In a second independent run of PCR-amplified truncated ccfDNA libraries (1 µg), an intermediate fraction (i.e., medium) targeted between the short and long fractions was also isolated (FIG. 13A). The distribution of sequencing-derived insert sizes from all short, medium, and long fractions, and unselected libraries are shown in FIG. 13B, which demonstrates a substantial amount of overlap between fractions. However, there was a statistically significant difference between fractions for both the peak fragment length by densitometry (F(3,48)=99.4, P<0.001; FIG. 13C) and the median insert size by NGS (F(3,48)=283.9, P<0.001; FIG. 13D) indicating distinct subfractions of ccfDNA were isolated from the original mononucleosome distribution of fragment sizes. There was a significant difference in the change of VAF between sub-fractions relative to the unselected library as determined by ddPCR (F(2,36)=5.4, P=0.009; FIG. 13E and FIG. 14) and sequencing (F(2,36)=17.7, P<0.001; FIG. 13F). A significantly larger increase was present in VAF for the short fractions compared to the long fractions by both ddPCR (2.9±2.6 vs. 0.8±0.5 fold-change, respectively; P=0.006) and NGS (2.0±0.8 vs. 0.7±0.2 fold-change, respectively; P<0.001). In the NGS data, there was also an increase in VAF from the short fractions compared to the medium fractions (2.0±0.8 vs. 1.3±0.5 fold-change, respectively; P=0.015) and the medium fractions compared to the long fractions (1.3±0.5 vs. 0.7±0.2 fold-change, respectively; P=0.013). Thus, selection of shorter ccfDNA fragments increased VAF and exclusion of longer ccfDNA fragments did not adversely affect VAF.

FIGS. 13A-E show enrichment of variant alleles in short ccfDNA fractions. In FIG. 13A, representative distributions by densitometry are shown of the isolated fractions (short—purple; medium—green; long—orange) from the original ccfDNA (black) of a single cancer patient. The fragment lengths include full-length adapters (~135 bp). The cumulative distribution of insert sizes at variant locations from all patients for each sub-fraction (FIG. 13B) show a profile consistent with densitometry (FIG. 13A). The peak fragment lengths from each patient by densitometry (FIG. 13C) and the median insert size by sequencing (FIG. 13D) were statistically significantly different between each respective sub-fraction, while observations for the long fraction were similar to the unselected mononucleosome (black). Enrichment for variant alleles was greatest in the short fraction by both ddPCR (FIG. 13E) and sequencing (FIG. 13F) with intermediate enrichment in the medium fraction (FIG. 13F). In the long fraction analyzed by both modalities there was a tendency for reduction in VAF (FIG. 13E and FIG. 13F). Solid bars represent the mean value. In FIG. 13C-E, mean±SD values are shown in gray. * P<0.05;  P≤0.01; * P≤0.001; NS=not significant; AFU=arbitrary fluorescent unit.

FIGS. 14A-E show VAF by ddPCR in size-selected ccfDNA libraries. Full-length libraries were prepared from unselected samples and short, medium, and long fractions. VAF of known variant was determined by ddPCR from 50 ng of library. Primary ddPCR data plots and gated areas generated by the RD Analyst software are shown. Gates for wildtype and variant droplet clusters were set on the unselected sample and applied to patient-matched size selected samples.

The potential source of enrichment was explored using NGS data as each WT or variant allele count was derived from a consensus read representing a unique ccfDNA molecule. WT and variant counts were used to determine the percent difference for each fraction relative to the unselected ccfDNA WT and variant counts was determined to identify effects of size selection on gain/loss of counts. Between ccfDNA subfractions there was a significant difference in WT counts (F(2,36)=42.6, P<0.001; FIG. 15A). The short ccfDNA fraction demonstrated the greatest reduction of WT counts at a mean of 48.2±17.1%. In contrast, WT counts in the long ccfDNA fraction was relatively unchanged at an increase of 1.3±9.1%. For variant counts, there was also a significant difference (F(2,36)=6.9, P=0.003; FIG. 15B) between subfractions largely due to the 28.6±21.4% reduction in variant counts present in the long ccfDNA fraction. The variant counts in the short ccfDNA fraction was relatively unchanged at an increase of 0.3±37.3% indicating loss of few variants during size selection. Of note, we also observed within each subfraction of ccfDNA a tendency for the variant alleles to have shorter insert sizes and a broader distribution compared to WT alleles (FIG. 16). These findings in combination with earlier observations from unselected ccfDNA (FIG. 6C) support a greater proportion of ctDNA at shorter ccfDNA fragment lengths. Thus, isolation of short ccfDNA fragments enriched for ctDNA through reduction of WT alleles without compromising variant allele detection.

FIGS. 15A-B show the percent difference in wild type (WT) and variant counts for each ccfDNA fraction relative to unselected ccfDNA counts. Compared to WT counts in unselected ccfDNA, there was a significant reduction in the short ccfDNA fraction compared to the medium and long ccfDNA fractions (FIG. 15A). For the variant counts (FIG. 15B), there was a significant reduction in the long ccfDNA fraction compared to the medium ccfDNA fraction and a strong trend to have fewer counts than the short ccfDNA fraction. *$P<0.05$, $P<0.01$, *$P<0.001$.

FIG. 16 shows median insert size for the wild type (WT) and variant allele (VA) for each ccfDNA fraction. Within each sub-fraction of the mononucleosome, there was evidence that the VA was shorter and had a broader distribution of insert sizes than the WT allele.

Automated Size Selection of ccfDNA Fragments Generated Larger Family Sizes

Figure 17:
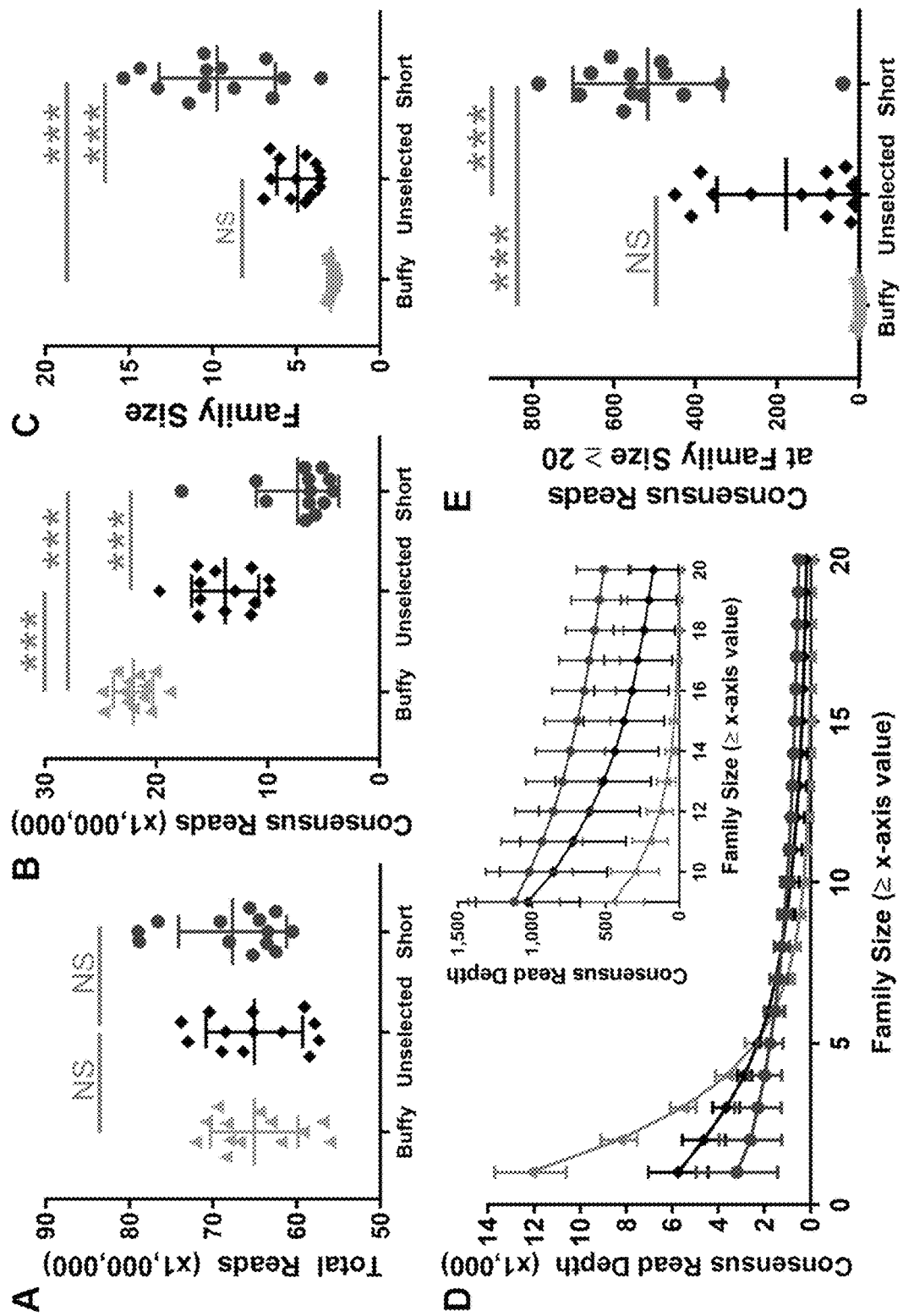
FIG. 17A illustrates data relating to the generation of large family sizes in short ccfDNA in accordance with an example embodiment.
FIG. 17B illustrates data relating to the generation of large family sizes in short ccfDNA in accordance with an example embodiment.
FIG. 17C illustrates data relating to the generation of large family sizes in short ccfDNA in accordance with an example embodiment.
FIG. 17D illustrates data relating to the generation of large family sizes in short ccfDNA in accordance with an example embodiment.
FIG. 17E illustrates data relating to the generation of large family sizes in short ccfDNA in accordance with an example embodiment.
Figure 18:
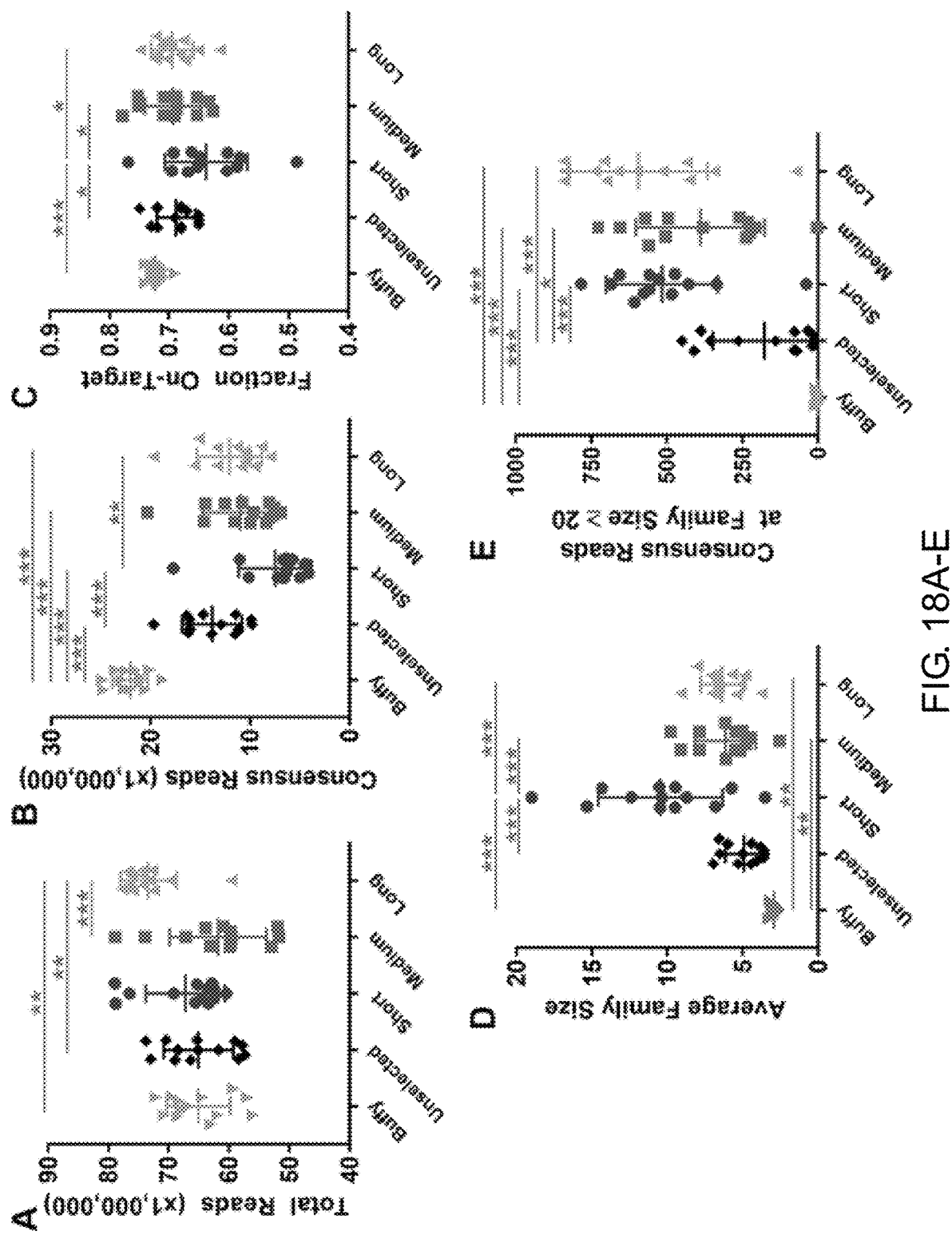
FIG. 18A illustrates data related to the generation of family sizes in buffy coat DNA, unselected ccfDNA, short, medium, and long ccfDNA fractions in accordance with an example embodiment.
FIG. 18B illustrates data related to the generation of family sizes in buffy coat DNA, unselected ccfDNA, short, medium, and long ccfDNA fractions in accordance with an example embodiment.
FIG. 18C illustrates data related to the generation of family sizes in buffy coat DNA, unselected ccfDNA, short, medium, and long ccfDNA fractions in accordance with an example embodiment.
FIG. 18D illustrates data related to the generation of family sizes in buffy coat DNA, unselected ccfDNA, short, medium, and long ccfDNA fractions in accordance with an example embodiment.
FIG. 18E illustrates data related to the generation of family sizes in buffy coat DNA, unselected ccfDNA, short, medium, and long ccfDNA fractions in accordance with an example embodiment.

The effects of a priori physical size selection on read depth and family size was next addressed. For all locations there was a statistically significant difference in total reads amongst all sample types (F(4,60)=6.4, P<0.001), which was solely attributable to a modest increase in the long ccfDNA fraction (FIG. 17A, FIG. 18A). This is an important starting point as the similarity in total reads between different samples indicates the subsequent findings are not due to experimental bias. A statistically significant difference in consensus aligned reads between groups was identified (F(4,60)=38.0, P<0.001). Buffy-coat DNA had the greatest number of consensus aligned reads, while short ccfDNA had the fewest (FIG. 17B, FIG. 18B). The on-target fraction was significantly different between groups (F(4,60)=6.4, P<0.001) largely due to a slight lowering of the on-target fraction in short ccfDNA (FIG. 18C). Average family size was also significantly different between sample types (F(4, 60)=20.1, P<0.001). Average family size was largest in the short ccfDNA fraction and smallest in buffy coat DNA (FIG. 17C). The family sizes for medium and long ccfDNA fractions were significantly larger than buffy coat DNA (FIG. 18D). As such, the reduction in sample complexity through isolation of ccfDNA mononucleosome fractions yielded larger average family sizes for a similar number of total reads even in the context of a reduced on-target fraction in the short ccfDNA fraction. This effect was then evaluated at the known variant locations. Although buffy coat DNA had the largest consensus read depth at family size ≥1, there was a rapid reduction with increasingly larger family sizes (FIG. 17D). Consensus read depth decayed more slowly for unselected ccfDNA and short ccfDNA (FIG. 17D). At family size ≥20, there was a statistically significant difference in consensus read depth between sample types at the variant locations (F(4,60)=24.8, P<0.001; FIG. 18E). The short, medium, and long ccfDNA fractions demonstrated the greatest consensus read depth at family size ≥20 (FIG. 17E; FIG. 18E).

FIGS. 17A-E show the generation of large family sizes in short ccfDNA. Total reads were similar between sheared buffy coat DNA, unselected ccfDNA, and short ccfDNA (FIG. 17A). Consensus read depth (family size ≥1) was greatest in buffy coat DNA, followed by unselected ccfDNA, and then short ccfDNA (FIG. 17B). Average family size was greatest in the short ccfDNA (FIG. 17C). At the specific variant locations for each patient, consensus read depth in buffy coat DNA rapidly decayed, reaching zero by family size ≥20 (FIG. 17D, gray). In contrast, both the unselected ccfDNA (FIG. 17D, black) and the short ccfDNA (FIG. 17D, purple) showed fewer consensus reads at family size ≥1, but maintained a greater read depth at larger family sizes (FIG. 17D, inset). Consensus read depth at family size ≥20 was greatest in short ccfDNA (FIG. 17E). In FIGS. 17A-C and FIG. 17E, solid bars represent the mean value. In FIGS. 17A-E, whiskers correspond to the standard deviation. *** $P \leq 0.001$; NS=not significant.

FIGS. 18A-E show the generation of family sizes in buffy coat DNA, unselected ccfDNA, short, medium and long ccfDNA fractions. Overall, total reads were similar between sample types except for the long ccfDNA fraction where there was a significant increase (FIG. 18A). Consensus read depth (family size ≥1) was greatest in buffy coat DNA and least in the short ccfDNA fraction (FIG. 18B). The on-target fraction was similar across all sample types except for the short ccfDNA fraction where there was a significant decrease (FIG. 18C). Average family size was greatest in the short ccfDNA, while the family sizes in the medium and long fractions were significantly larger than the buffy coat DNA (FIG. 18D). At the specific variant locations for each patient, consensus read depth at family size ≥20 was greatest in the short, medium, and long fraction (FIG. 18E). In FIGS. 18A-E, solid bars represent the mean value and whiskers correspond to the standard deviation. * $P \leq 0.001$;  $P=0.01$; * $P<0.05$; NS=not significant.

Larger Family Sizes Reduced False Positives

Figure 19:
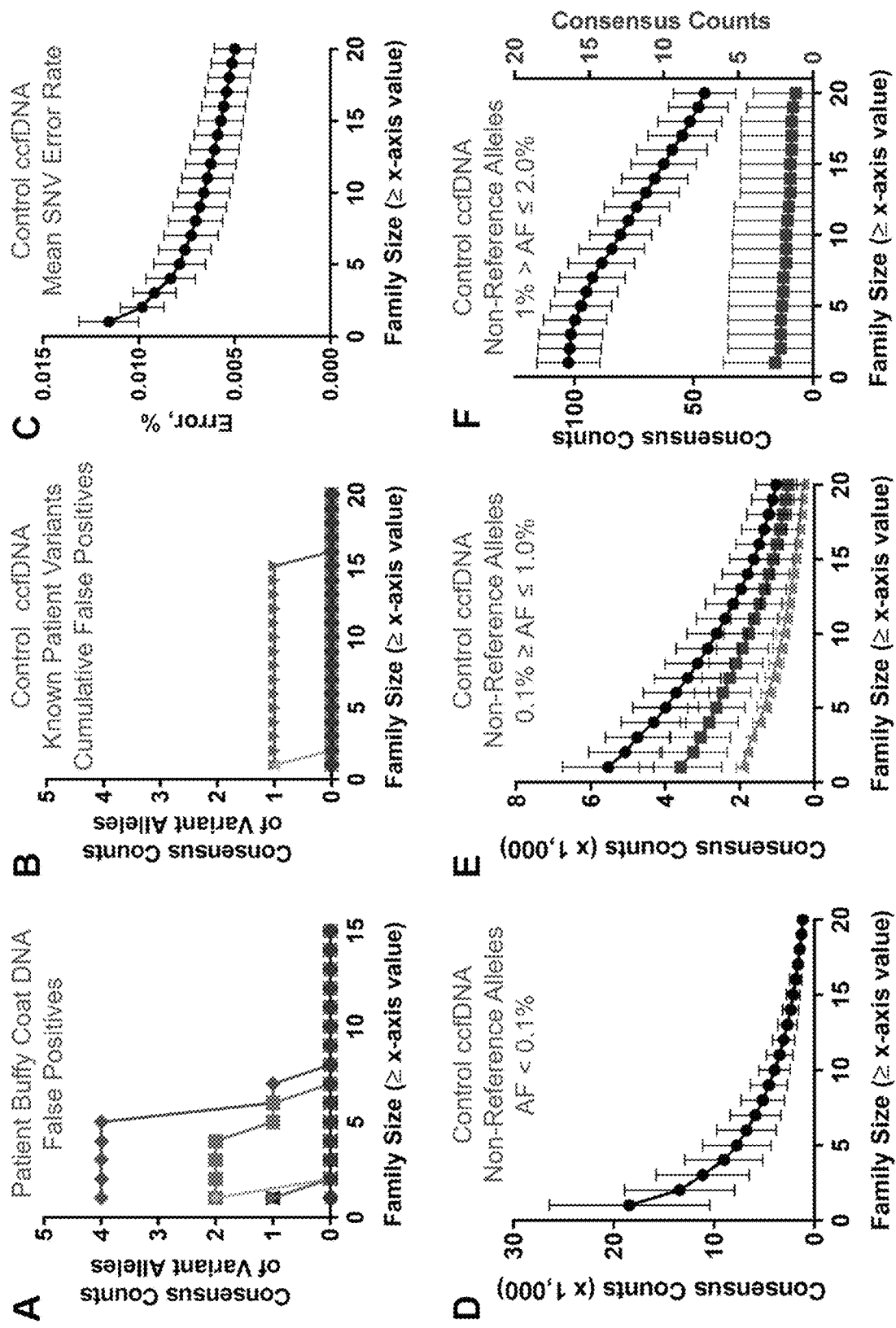
FIG. 19A illustrates data related to the reduction of false positives at larger family sizes in accordance with an example embodiment.
FIG. 19B illustrates data related to the reduction of false positives at larger family sizes in accordance with an example embodiment.
FIG. 19C illustrates data related to the reduction of false positives at larger family sizes in accordance with an example embodiment.
FIG. 19D illustrates data related to the reduction of false positives at larger family sizes in accordance with an example embodiment.
FIG. 19E illustrates data related to the reduction of false positives at larger family sizes in accordance with an example embodiment.
FIG. 19F illustrates data related to the reduction of false positives at larger family sizes in accordance with an example embodiment.

The association between family size and false positives was also addressed. During a targeted search for the corresponding known variant in the buffy coat DNA from each patient, few false positives were identified (FIG. 19A). We then analyzed unselected ccfDNA from 11 healthy controls sequenced under identical conditions. As with the patient samples, the greater of 10 ng or 1 mL plasma equivalent of ccfDNA was used for the initial library input. The mean amount of ccfDNA present in the healthy controls was 11.6±4.7 ng/mL plasma (median: 11.3 ng/mL plasma; range: 3.8-15.3 ng/mL plasma). While there was a trend for a larger amount of ccfDNA per mL plasma in patients, the difference was not statistically significantly greater than the controls most likely due to the large variation in the patient data and sample size associated with each cohort (20.1±14.5 vs. 11.6±4.7 ng/mL plasma, respectively; P=0.07). Similarly, few false positives were found for the known patient variants in healthy control ccfDNA (FIG. 19B). In both patient buffy coat DNA and control ccfDNA the allele frequency for known variants was <0.01% suggesting that constrained searches of known variants may be associated with a low error rate. Of note, we also observed that family size in the control unselected ccfDNA was significantly larger than patient unselected ccfDNA (8.4±2.7 vs. 4.9±1.2, respectively; P<0.001), which could not be explained by differences in total reads or on-target fractions (FIGS. 10A-D). This latter finding supports the supposition that reduction in sample complexity through size selection generates larger family sizes as patient-derived ccfDNA is expected to be more complex than control ccfDNA due to contributions from tumor cells, higher concentration of ccfDNA present in plasma, or both.

FIG. 19A-F show the reduction of false positives at larger family sizes. Corresponding variants present in patient ccfDNA were queried in matched buffy coat DNA (FIG. 19A). False positives were few and incrementally decreased with larger family sizes (FIG. 19A). FIG. 19B shows the cumulative number of false positives from all healthy control ccfDNA and all five targeted patient variants is shown. Overall, only two false positives were identified. In (FIG. 19C), the mean error rate across the entire capture panel (128 genes, 128 kb) decreased with increasingly larger family sizes. Total consensus aligned counts for non-reference alleles with AF<0.1% (D), 0.1%≥AF≤1.0% (E), and 1.0%>AF≤2.0% (FIG. 19F) are shown (black circles). In (FIG. 19E) and (FIG. 19F), non-reference alleles are sub-categorized as "unique" (blue squares) or "shared" (gray triangles). In (FIG. 19F), "shared" non-reference alleles are not shown as they are similar to the total count. In (FIG. 19F), the "unique" non-reference allele count is plotted on a second y-axis. In (FIGS. 19C-F), whiskers correspond to the standard deviation.

Figure 20:
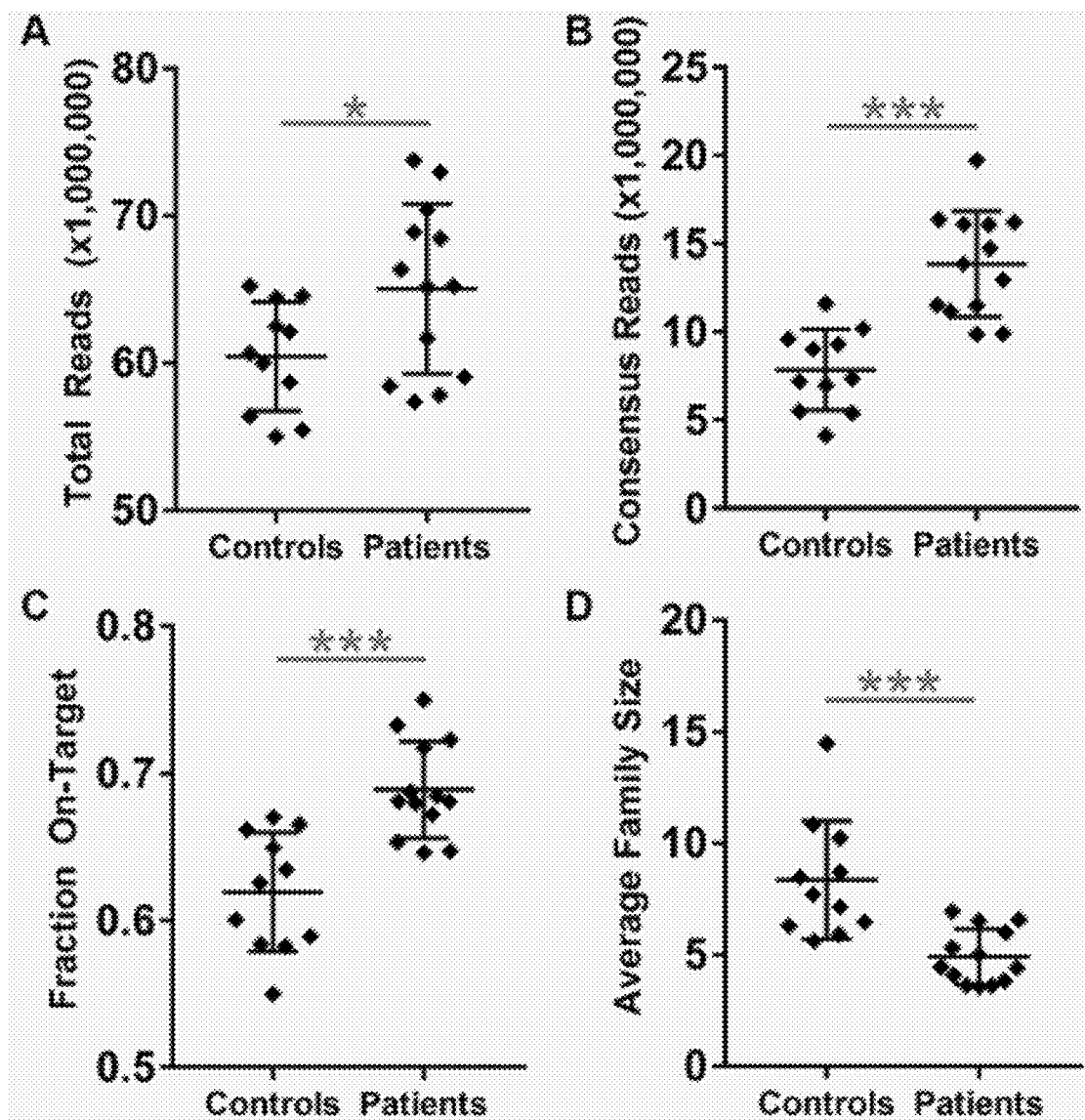
FIG. 20A illustrates data showing comparisons of coverage, on-target fraction, and family size between unselected ccfDNA from healthy controls and patients in accordance with an example embodiment.
FIG. 20B illustrates data showing comparisons of coverage, on-target fraction, and family size between unselected ccfDNA from healthy controls and patients in accordance with an example embodiment.
FIG. 20C illustrates data showing comparisons of coverage, on-target fraction, and family size between unselected ccfDNA from healthy controls and patients in accordance with an example embodiment.
FIG. 20D illustrates data showing comparisons of coverage, on-target fraction, and family size between unselected ccfDNA from healthy controls and patients in accordance with an example embodiment.

FIGS. 20A-D show comparison of coverage, on-target fraction, and family size between unselected ccfDNA from healthy controls and patients. Although total reads (FIG. 20A), consensus read depth (FIG. 20B), and on-target fraction (FIG. 20C) were significantly higher in the patient cohort, the average family size was largest in the controls (FIG. 20D). In FIGS. 20A-D, solid bars represent the mean value and whiskers correspond to the standard deviation.

The aligned base error rate in the control ccfDNA was evaluated to study occurrence of false positives during untargeted searches using the 128 gene (128 kb) panel. Globally, at family size ≥1 the mean error rate was 0.011±0.002% and there was a reduction in error with incrementally larger family sizes (FIG. 19C). At family size ≥20 the mean error rate was significantly reduced by 57.0±7.7% (P<0.001). Although the global mean error rate provides an overall metric for quality of sequencing, the principal source of false positives during NGS detection of very low frequency variants are due to local errors associated with stochastic noise or position-specific common errors. Locally, non-reference allele counts in control ccfDNA similarly reduced with incrementally larger family sizes (FIG. 19D-F). At a non-reference allele frequency ≥0.1% the data was parsed into "unique" and "shared" locations. A shared location was defined as the presence of a non-reference allele in at least three control ccfDNA samples, thus unique locations were representative of stochastic noise. The majority of non-reference alleles detected at a frequency ≥0.1% and ≤1.0% were due to unique rather than shared locations (FIG. 19E). Within this frequency range there was a significant reduction of 81.6±7.3% (P<0.001) in unique non-reference allele counts between family size ≥1 and family size ≥20. Non-reference alleles detected at a frequency >1% and ≤2.0% were relatively few and largely due to shared locations (FIG. 19F). However, it is notable that on average there were ~2 non-reference unique variants in the control ccfDNA with a frequency >1% and ≤2.0% present even at large family sizes (FIG. 19F). Combined, these findings indicate stochastic sequencing noise and/or PCR errors may confound identification of true variant alleles during untargeted searches. Regardless, the control data provides compelling evidence that generation of large family sizes improves in silico error reduction.

VAF Remained Constant in Shorter ccfDNA Fractions at Larger Family Sizes

Figure 21:
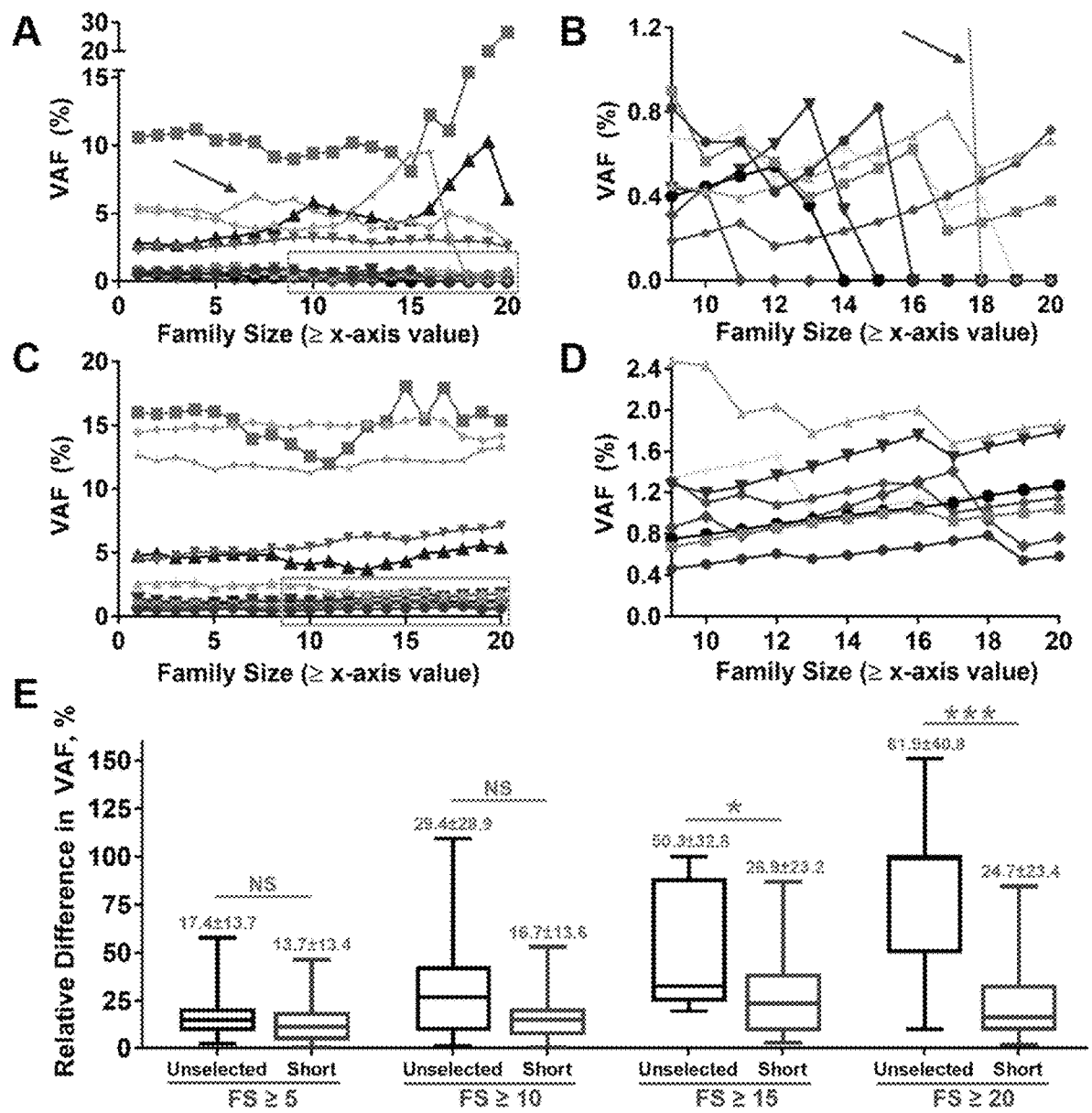
FIG. 21A illustrates data showing the effects of family size on VAF in accordance with an example embodiment.
FIG. 21B illustrates data showing the effects of family size on VAF in accordance with an example embodiment.
FIG. 21C illustrates data showing the effects of family size on VAF in accordance with an example embodiment.
FIG. 21D illustrates data showing the effects of family size on VAF in accordance with an example embodiment.
FIG. 21E illustrates data showing the effects of family size on VAF in accordance with an example embodiment.

The effects of family size on VAF was investigated since larger family sizes were associated with a reduced consensus read depth. In the unselected ccfDNA, VAF remained relatively constant up to family size ≥10; however, VAF subsequently became inconsistent at larger family sizes (FIGS. 21A-B). In ~46% of patients (6 of 13) the variant allele was lost before family size ≥20 (FIG. 21B). In contrast, the VAF in the short ccfDNA fraction was consistent up to a family size ≥20 without loss of variant detection in any patient (FIGS. 21C and 21D). The absolute value of relative percent change in VAF was similar for unselected ccfDNA and short ccfDNA at family sizes ≥5 and ≥10 (FIG. 21E). The relative percent change was significantly larger in the unselected ccfDNA compared to the short ccfDNA fraction at a family size ≥15 and a family size ≥20 (FIG. 21E). As such, VAF remained more consistent at larger family sizes in the short ccfDNA fraction than in the unselected ccfDNA regardless of initial VAF magnitude. The medium and long ccfDNA fractions exhibited similar improvement in VAF consistency at larger family sizes relative to the unselected ccfDNA (FIGS. 22A-C and FIGS. 23A-C, respectively), which further supports the strengths of reducing sample complexity to improve sensitivity even though each fraction was associated with loss of variant detection in at least one patient by family size ≥20. Thus, the continued detection of low frequency variants at large family sizes in the short ccfDNA fraction may have been supported by the combined effects of increased consensus read depth and variant enrichment for the total number of reads used in this study.

FIGS. 21A-E show the effects of family size on VAF. Overall, VAF was relatively stable up to a family size ≥10 in unselected ccfDNA (FIG. 21A). However, at larger family sizes VAF became less stable and included complete loss of variants in some samples (FIG. 21B, magnification of area in blue box shown in FIG. 21A). Of note, complete loss of the variant allele occurred in one sample with an initial VAF >5% (FIG. 21A and FIG. 21B, black arrow). In contrast, VAF remained relatively stable up to family size ≥20 in the short ccfDNA fraction (FIG. 21C, magnification of area in the box shown in FIG. 21D). Note the apparent increase of VAF in the short ccfDNA fraction at lower allele frequencies (FIG. 21D) compared to the unselected ccfDNA (FIG. 21B). The relative percent difference in VAF was similar in unselected and short ccfDNA at family size (FS) ≥5 and FS ≥10 (FIG. 21E). However, the relative percent difference was statistically significantly lower in the short ccfDNA fraction at FS ≥15 and FS ≥20 (FIG. 21E). * P<0.05; *** P≤0.001; NS=not significant.

Figure 22:
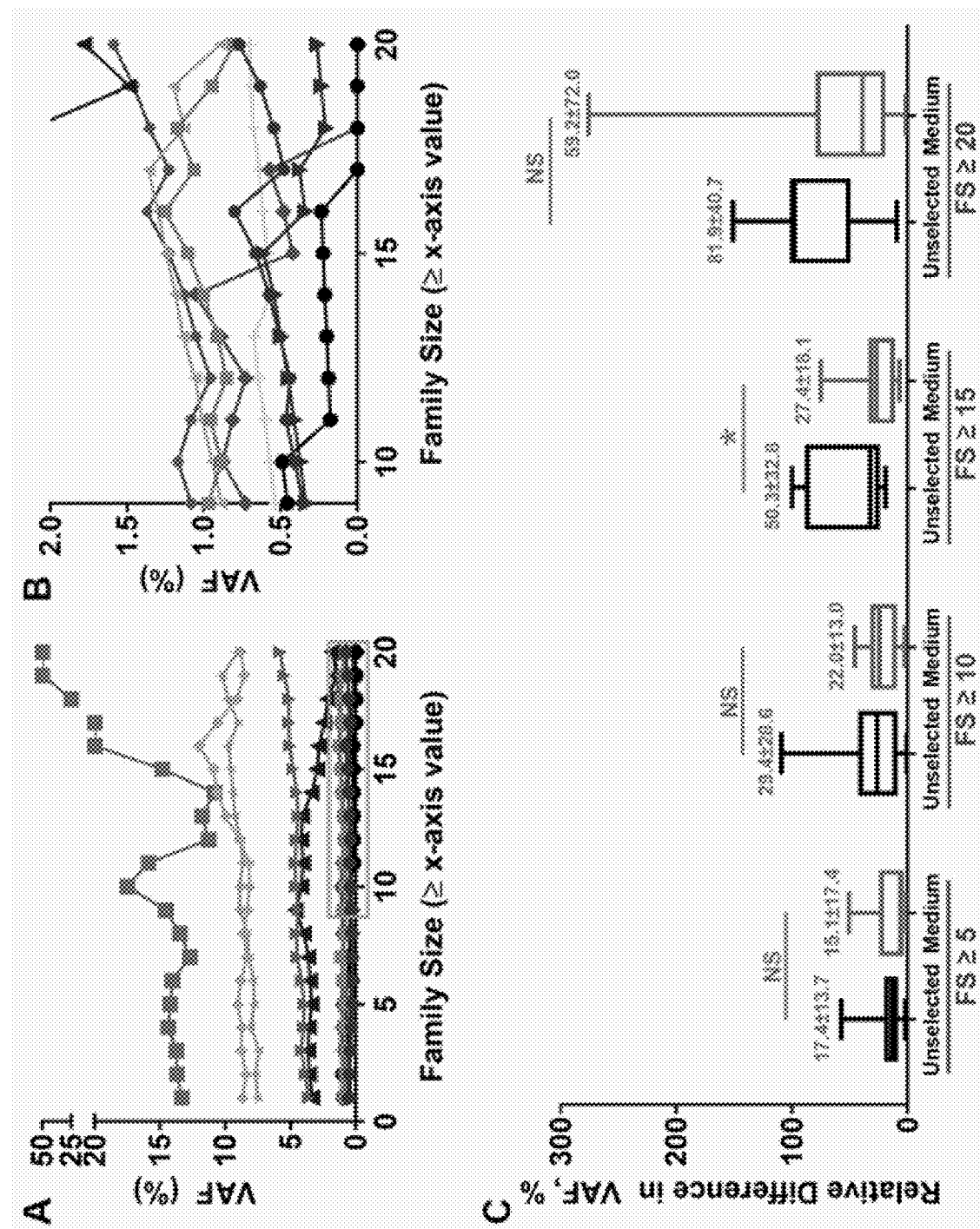
FIG. 22A illustrates data showing the effects of family size on VAF in the medium ccfDNA fraction in accordance with an example embodiment.
FIG. 22B illustrates data showing the effects of family size on VAF in the medium ccfDNA fraction in accordance with an example embodiment.
FIG. 22C illustrates data showing the effects of family size on VAF in the medium ccfDNA fraction in accordance with an example embodiment.

FIGS. 22A-C show the effects of family size on VAF in the medium ccfDNA fraction. Overall, VAF was relatively stable up to a family size ≥15 in the medium fraction of ccfDNA (FIG. 22A). However, at larger family sizes VAF became less stable and included complete loss of variants in some samples (FIG. 22B, magnification of area in the box shown in FIG. 22A). The relative percent difference in VAF was similar in unselected and medium ccfDNA at family size (FS) ≥5 and FS ≥10, but was significantly larger in unselected ccfDNA at FS ≥15 (FIG. 22C). At FS ≥20, there was a trend for a larger difference of VAF in the unselected ccfDNA, but it was not statistically significant. * P<0.05; NS=not significant.

Figure 23:
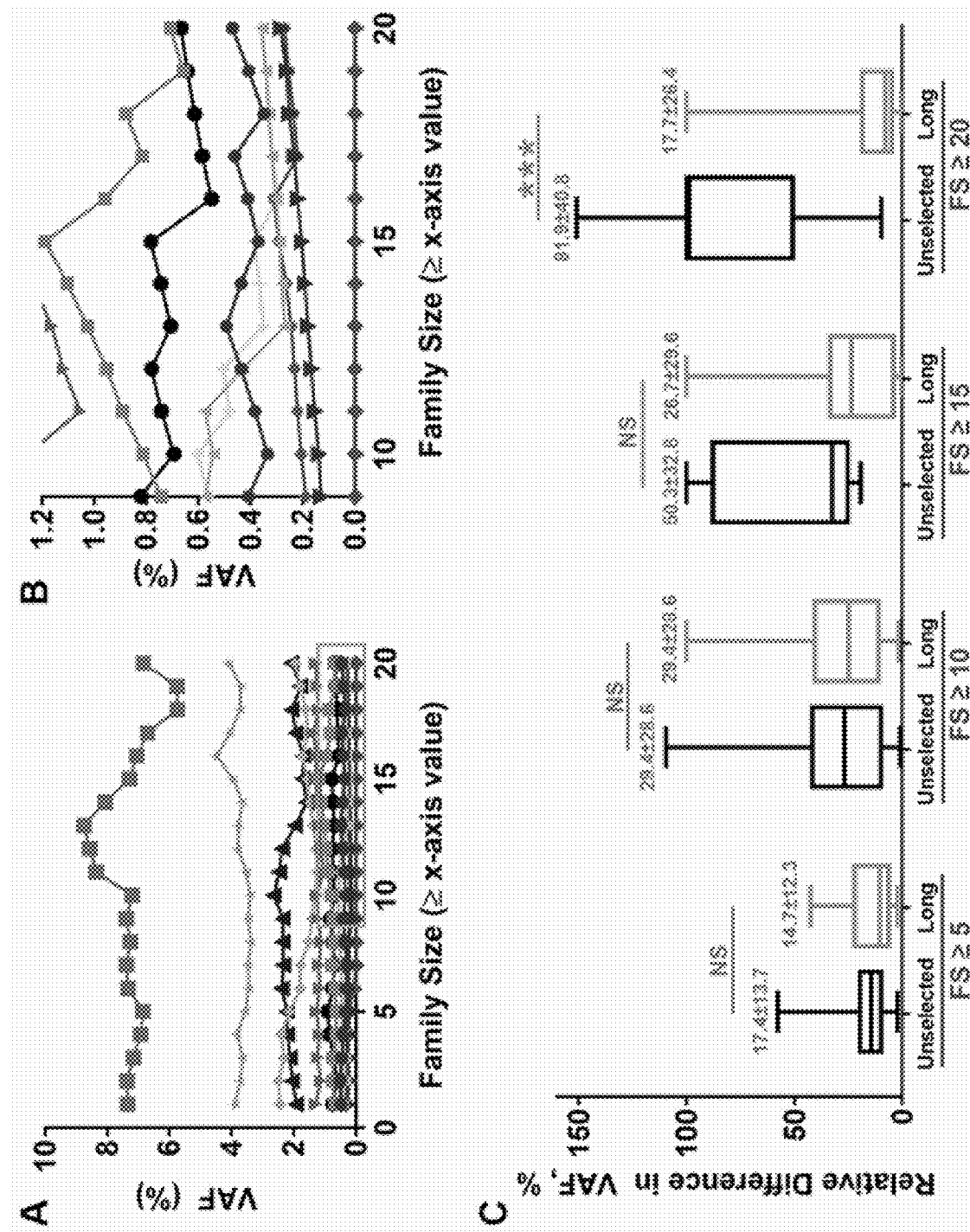
FIG. 23A illustrates data showing the effects of family size on VAF in the long ccfDNA fraction in accordance with an example embodiment.
FIG. 23B illustrates data showing the effects of family size on VAF in the long ccfDNA fraction in accordance with an example embodiment.
FIG. 23C illustrates data showing the effects of family size on VAF in the long ccfDNA fraction in accordance with an example embodiment.

FIGS. 23A-C show the effects of family size on VAF in the long ccfDNA fraction. Overall, VAF was relatively stable in the long ccfDNA fraction (FIG. 23A) even at large family sizes and lowest VAFs (FIG. 23B, magnification of area in the box shown in FIG. 23A). Of note, in one sample the variant allele was lost at FS ≥6. The relative percent difference in VAF was similar in unselected and long ccfDNA at family size (FS) ≥5, FS ≥10, and FS ≥15, but was significantly larger in unselected ccfDNA at FS ≥20 (FIG. 23C). *** P≤0.001; NS=not significant.

Methods

Patient Samples and DNA Isolation

Healthy adult volunteers and cancer patients with a BRAF or KRAS solid tumor variant associated with a primary melanoma, pancreatic ductal adenocarcinoma, or colorectal adenocarcinoma were recruited for enrollment. Blood samples were collected in BCT tubes (Streck, La Vista, Nebr.) and processed for buffy coat and plasma extraction within 24 hours. The buffy coat and plasma were separated from whole blood by centrifugation at 1,900 g×10 minutes at 4° C. and aspirated to new tubes. Plasma was then centrifuged at 16,000 g×10 minutes at 4° C. to remove any cellular debris. The plasma supernatant and the buffy coat were stored at −80° C. until further use. Buffy coat DNA (i.e., white blood cell DNA) was isolated from the buffy coat using the QIAamp DNA Mini Kit (Qiagen, Germantown, Md.) and eluted in a final volume of 100 µL 10 mM Tris-Cl and 0.5 mM EDTA (pH 9.0). 100 ng of buffy coat DNA was then sheared using a focused-ultrasonicator (S220, Covaris, Woburn, Mass.) with a targeted size of 175 bp. ccfDNA was isolated from 8 mL of plasma using the QIAamp Circulating Nucleic Acid Kit (Qiagen) and eluted in a final volume of 50 µL 10 mM Tris (pH 8.0) and 0.1 mM EDTA. ccfDNA was not sheared.

NGS Library Preparation, Sequencing, and Bioinformatics

Libraries for buffy coat DNA (100 ng) and ccfDNA (10 ng or the quantity equivalent to ccfDNA from 1 mL of plasma, whichever was greater) were prepared using the Kapa Biosystems Hyper Prep Kit for end repair, A-tailing, and ligation of truncated custom IDT adapters that contained an eight base-pair random barcode (i.e., unique molecular identifier) in the index 2 position of a standard Illumina adapter. The Kapa HiFi 2× master mix with truncated-length adapter primer was used for initial library amplification followed by the use of full-length indexing primers during subsequent PCR amplification steps.

Full-length buffy coat DNA and ccfDNA libraries were enriched for regions of interest using a custom designed IDT Xgen capture probe set (Integrated DNA Technologies) containing full exonic or hotspot coverage of 128 genes (128 kb). Paired-end sequencing (2×125 bp) of libraries was performed on an Illumina HiSeq 2500. Reads in FASTQ files were aligned to the GRCh37 reference genome and those with the same unclipped alignment start position were grouped into families based on >0.875 molecular barcode similarity. Read sequence was extracted from each family and consensus called on each base position. Those with >0.66 concordance were assigned the predominant base, otherwise, an N. See the consensus aligned workflow in FIG. 24. Fragment length was derived from paired-end alignment information according to SAM format. Identification of wild type vs. variant allele was determined by a 100% match to an 11 bp string within aligned consensus sequences at the location corresponding to each known variant. Additionally, aligned base error rates and occurrence of localized false positive variants were calculated using our open source EstimateErrorRates and MpileupParser applications. The USeq EstimateErrorRates application calculates base level error rates observed in quality alignments (≥MQ20) from normal germline sequencing datasets. It parses a Samtools mpileup alignment stack for regions of 7 adjacent bases with adequate read depth (≥100 Q20 bases), no observed indels, and no indication of heterozygous or homozygous SNVs (allele frequencies ≤0.1). Good quality (≥Q20), non-reference, center base observations in each passing region are tabulated. These are used to calculate error rates for each base as well as the total error observed from quality alignments and quality bases. The USeq MpileupParser works in a similar fashion by parsing a Samtools mpileup alignment stack covering bases in a bed file of the 128 kb capture panel coverage with 25 base pair padding. Only quality alignments (≥MQ20) and quality bases (≥Q20) are counted. Locations with evidence of a heterozygous or homozygous allele (AF >0.1) are ignored. It outputs a bed file of each passing base with its observed non-reference allele frequencies. At FS ≥1, allele frequencies were binned (<0.1%, 0.1% to 1.0%, and 1% to 2.0%) and then tracked for presence/absence at subsequent family sizes.

Figure 24:
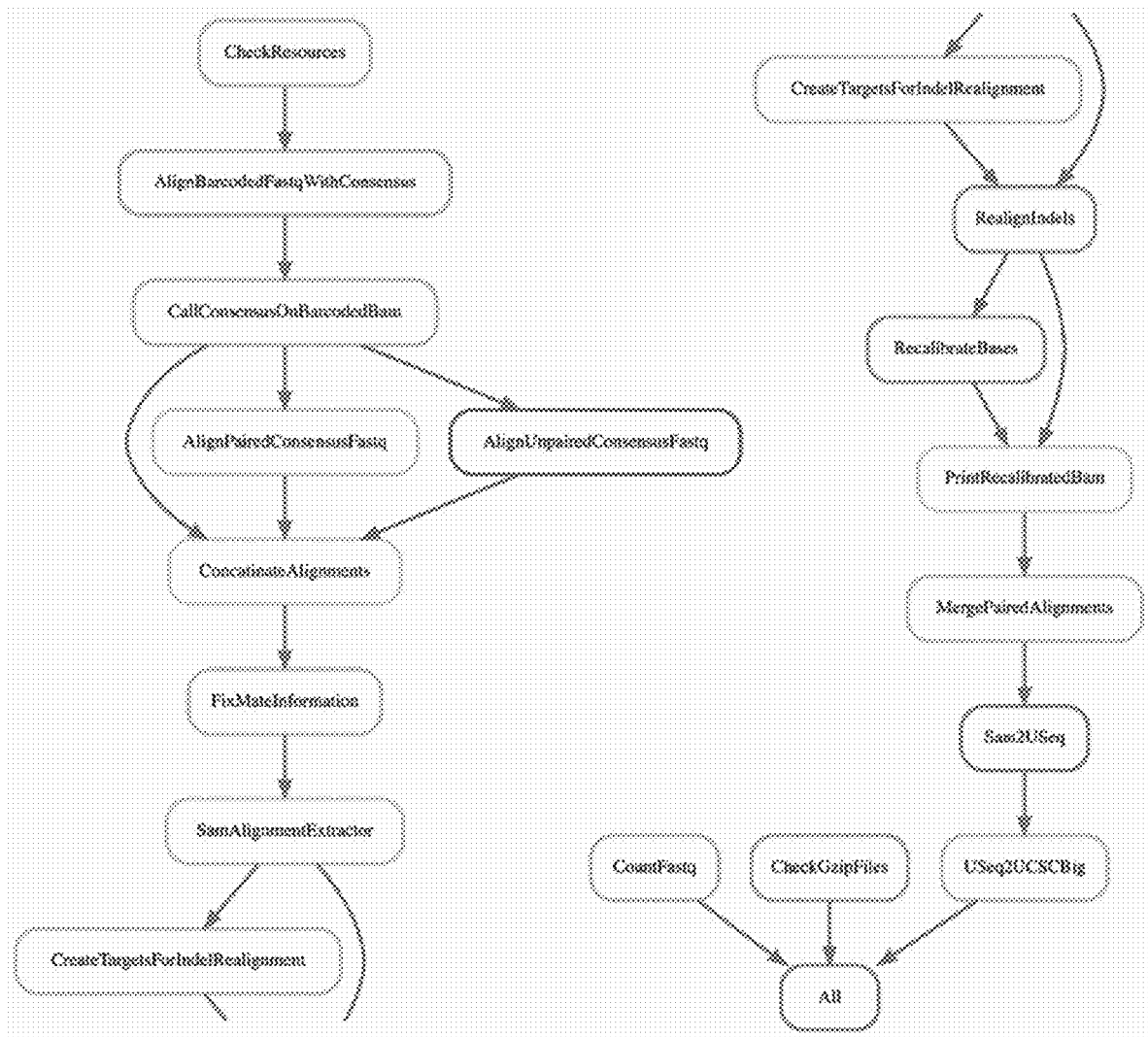
FIG. 24 illustrates an example consensus alignment workflow in accordance with an example embodiment.

FIG. 24 shows an example of a consensus alignment workflow. A Snakemake workflow was constructed to convert fastq sequencing datasets with unique molecular identifiers to processed alignments. This involved 18 steps as represented in this directed acyclic graph. In brief, alignments are generated with bwa. Those with the same unclipped start position are grouped by UMI and collapsed to a single error corrected consensus sequence with USeq tools. These are aligned, merged, and passed through GATK's best practice INDEL realignment and base score recalibration process. Throughout, various quality control files are generated including a unique observation read coverage data track.

Fragment Size Selection

Selection of fractions from truncated ccfDNA libraries was done with an automated liquid handler (NIMBUS Select, Hamilton, Reno, Nev.) that incorporated Ranger Technology (Coastal Genomics, Burnaby, BC) for the monitoring and real-time manipulation of electrophoretic mobilities through a 3.0% agarose matrix in a 12-channel cassette. Prior to use on human samples, extraction parameters were optimized with a four-rung ladder constructed from lambda phage using Hot Start Taq DNA polymerase (Roche, New York, N.Y.) and the following primer pairs to generate specific lengths of lambda DNA:

278 bp:

[SEQ ID NO: 01]
5'-GATGCGATGTTATCGGTGCG-3'
and

[SEQ ID NO: 02]
5'-CACAGGTGAGCCGTGTAGTT-3'

268 bp:

[SEQ ID NO: 03]
5'-TGGAACCCACCGAGTGAAAG-3'
and

[SEQ ID NO: 04]
5'-CAATGCAGCAGCAGTCATCC-3'

-continued

```
233 bp:
                                    [SEQ ID NO: 05]
5'-CGGCACGATCTCGTCAAAAC-3'
and

[SEQ ID NO: 06]
5'-GCCTTGAACTGAAATGCCCG-3'

223 bp:
                                    [SEQ ID NO: 07]
5'-GGAAGCTGCATGATGCGATG-3'
and

[SEQ ID NO: 08]
5'-CTGGTGCGTTTCGTTGGAAG-3'
```

Ladder lengths were constructed to guide targeting of desired ccfDNA fragment lengths after the addition of the truncated adapters (~103 bp; FIG. 6A). The short fraction was optimized to extract a ccfDNA fraction that included both the 223 and 233 bands and no portion of the 268 band, while the long fraction was optimized to include both the 268 and 278 bands, but not the 233 band. After optimization, PCR-amplified truncated ccfDNA libraries (1 μg; FIG. 6A) were loaded into the cassette (Coastal Genomics) and short and long fractions were collected from a single run. A second run using intermediate parameters to collect a medium fraction between the short and long fractions from PCR-amplified truncated ccfDNA libraries (1 μg) was also performed. Collected fractions were mixed with QG buffer (Qiagen; 1.4 volumes to 1 volume of sample) and loaded onto a QIAquick spin column from the QIAquick PCR Purification Kit (Qiagen). The remaining manufacturer's instructions for the kit were then followed and ccfDNA library fractions were eluted in 30 μL of EB buffer (Qiagen). From the eluate, 20 μL was used with full-length indexing primers during PCR amplification in preparation for sequencing (FIG. 6A). Densitometry (TapeStation 2200, Agilent Technologies) was used to characterize ccfDNA fragment distribution from unselected and size-selected ccfDNA full-length libraries at a loading concentration 5 ng/μL.

Droplet Digital PCR

Droplet digital PCR (ddPCR) assays were performed on the RainDrop Plus™ Digital PCR System (Bio-Rad). For detection of EGFR T790M and KRAS G13D published assays were used. For additional assays, primer pairs were designed with a target amplicon size <100 bp to accommodate amplification from cell-free DNA samples. Dual-color (FAM/TET) hydrolysis probes containing locked nucleic acid (LNA) nucleotides, 3' terminal and/or internal quenchers (Iowa Black/ZEN) were designed to distinguish wildtype from mutant alleles. All primers and probes were sourced from Integrated DNA Technologies. Reactions were set up in a final volume of 25 μL using TaqMan Genotyping Master Mix (Life Technologies). Primers were added to a final concentration of 500 nM, probes to final concentrations of 100 nM (BRAT) or 200 nM (all other assays). Up to 10.5 μL of template DNA was tested containing 50 ng of amplified sequencing libraries or varying amounts of cell-free DNA (range: 7-46 ng). False positive noise and limit of blank (LOB) of all assays was determined from a collection of wild-type-only samples and no-template controls (FIG. 25A-C). Data were analyzed using RD Analyst software.

FIGS. 25A-C show false positive droplet events in control samples. For each ddPCR assay false positive droplet events were measured in a collection of controls (FIG. 25A). Samples tested in each assay included full-length libraries (n≥11), plasma cell-free DNA (n≥9), buffy coat DNA (n≤3) and no template controls (n≤3). A Poisson model was applied to fit the observed false positive distribution (dashed line). The mean of the Poisson distribution (λ) was determined and the limit of blank (LOB) for each assay was calculated from the 95% confidence interval of the Poisson distribution as well as from the 95% limit of the empirical distribution. False positive variant allele frequency (VAF) was determined for each control experiment, excluding no template controls (FIG. 25B). Median VAF, interquartile range and 95 percentile (error bars) of false positive VAFs for each assay are indicated. Data are summarized in table format (FIG. 25C).

Size Selection of Synthetically Spiked ccfDNA

Synthetic DNA gBlocks® including 130 bp of genomic EGFR sequence spanning the c.2369C>T (p.T790M) point mutation and 165 bp of genomic BRAF sequence spanning the c.1799T>A (p.V600E) mutation were purchased from Integrated DNA Technologies. gBlocks® were reconstituted in TE buffer, serially diluted and quantified by ddPCR to determine absolute copy number. Sufficient 130 bp EGFR T790M and 165 bp BRAF V600E gBlocks® were spiked into a sample of pooled cell-free DNA collected from healthy donors to yield a target VAF of ~10% for both alleles. 10 ng of spiked cell-free DNA and 50 ng of the corresponding unspiked pooled ccfDNA were used for NGS truncated library preparation as described above. The presence of synthetic mutations in the spiked library were verified by ddPCR (EGFR T790M 11.4% VAF; BRAF V600E 12.1%). Truncated-length libraries of spiked and unspiked samples were subsequently mixed to generate an eight-step serial dilution series. Two independent dilution series were produced. 1 μg of each dilution and unspiked control libraries were size-selected for isolation of short and long fractions as described above. Full-length libraries were produced from extracted fractions and unselected samples and analyzed for EGFR T790M and BRAF V600E VAF by ddPCR.

Statistics

For paired samples, the paired t-test was applied. The independent t-test was used for comparison of two independent samples and Levene's test for inequality determined equal or unequal variance. For multiple samples, one-way analysis of variance (ANOVA) was applied followed by a Tukey post-hoc test for comparisons between pairs of samples. Pearson's correlation coefficient (r) evaluated associations between samples. Boxplots show the median value and the $25^{th}$ and $75^{th}$ quartiles. Whiskers on boxplots identify the $5^{th}$ and the $95^{th}$ percentiles. For comparison of VAF between different family sizes, the absolute value of relative percent change was calculated to weight all changes in VAF similarly. For comparison of WT and variant counts between ddPCR and NGS, the percent change relative to ddPCR was calculated to normalize the data to account for differences in counts between samples. All statistical analysis was performed in SPSS (Version 24, IBM). Statistical significance was defined as $P<0.05$.

The invention claimed is:

1. A method of increasing detection of low-abundant fragments of cell-free DNA (ccfDNA) in a biological sample from a subject, comprising:
 isolating an initial fraction of ccfDNA fragments from a biological sample;
 ligating a unique molecular identifier (UMI) to each of the ccfDNA fragments in the initial fraction;
 amplifying the plurality of ccfDNA fragments to generate a ccfDNA library;
 isolating a short fraction of ccfDNA fragments from the ccfDNA library, where the ccfDNA fragments in the short fraction are limited to a size of less than or equal to 160 base pairs (bp);
 amplifying the ccfDNA fragments in the short fraction; and
sequencing the ccfDNA fragments in the short fraction to generate sequenced ccfDNA fragments.

2. The method of claim 1, wherein the ccfDNA fragments in the short fraction are limited to a size of less than or equal to 155 bp.

3. The method of claim 1, wherein the ccfDNA fragments in the short fraction are limited to a size of less than or equal to 150 bp.

4. The method of claim 1, wherein isolating the short fraction of ccfDNA fragments from the ccfDNA library comprises:
 migrating ccfDNA fragments from the ccfDNA library through an electrophoretic gel;
 selecting a target portion of the electrophoretic gel corresponding to the short fraction based on ccfDNA fragment size; and
 extracting the target portion of the electrophoretic gel to isolate the short fraction of ccfDNA fragments.

5. The method of claim 4, wherein the electrophoretic gel is a polyacrylamide gel.

6. The method of claim 4, wherein the electrophoretic gel is an agarose gel.

7. The method of claim 4, wherein migrating ccfDNA fragments, selecting the target portion, and extracting the target portion are performed by an automated electrophoresis gel system.

8. The method of claim 1, wherein isolating the short fraction of ccfDNA fragments from the ccfDNA library comprises:
 separating ccfDNA fragments from the ccfDNA library by liquid chromatography into fractions according to ccfDNA fragment size;
 selecting a target fraction corresponding to the short fraction based on ccfDNA fragment size; and
 extracting the target fraction to isolate the short fraction of ccfDNA fragments.

9. The method of claim 1, further comprising:
 grouping the sequenced ccfDNA fragments according to each UMI; and
 building a consensus sequence for each UMI group of sequenced ccfDNA fragments.

10. The method of claim 9, further comprising:
 comparing at least one consensus sequence against a sequence library of target sequences associated with genetic conditions; and
 matching the at least one consensus sequence to a target sequence in the sequence library.

11. The method of claim 10, wherein the genetic condition is a medical condition and the method further comprises:
 determining the medical condition associated with the matched target sequence;
 diagnosing the medical condition in the subject; and
 performing an appropriate medical treatment on the subject to treat the medical condition.

12. The method of claim 11, wherein the medical condition is a solid tumor and the consensus sequence is for circulating tumor-derived DNA (ctDNA).

13. The method of claim 12, wherein the appropriate medical treatment is tumor-specific treatment.

14. The method of claim 10, wherein the genetic condition is a genetic phenotype.

15. The method of claim 14, wherein the subject is a pregnant mother and the genetic phenotype is a fetal genetic phenotype.

16. The method of claim 1, wherein the UMI comprises a member selected from the group consisting of an external adapter, an internal adapter, and a combination thereof.

* * * * *